US005871907A

United States Patent [19]
Winter et al.

[11] Patent Number: 5,871,907
[45] Date of Patent: *Feb. 16, 1999

[54] METHODS FOR PRODUCING MEMBERS OF SPECIFIC BINDING PAIRS

[75] Inventors: Gregory Paul Winter; Kevin Stuart Johnson; Andrew David Griffiths; Andrew John Hammond Smith, all of Cambridge, United Kingdom

[73] Assignees: Medical Research Council, London; Cambridge Antibody Technology Limited, Melbourn, both of England

[*] Notice: The term of this patent shall not extend beyond the expiration date of Pat. No. 5,858,657.

[21] Appl. No.: 150,002

[22] PCT Filed: May 15, 1992

[86] PCT No.: PCT/GB92/00883

§ 371 Date: Mar. 31, 1994

§ 102(e) Date: Mar. 31, 1994

[87] PCT Pub. No.: WO92/20791

PCT Pub. Date: Nov. 26, 1992

[30] Foreign Application Priority Data

May 15, 1991 [GB] United Kingdom ............. 9110549
Mar. 24, 1992 [GB] United Kingdom ............. 9206318

[51] Int. Cl.$^6$ ................. C12Q 1/68; C12P 21/02; C12N 15/70
[52] U.S. Cl. ................. 435/6; 435/69.1; 435/91.1; 435/172.3; 435/235.1; 435/320.1
[58] Field of Search ............. 435/320.1, 235.1, 435/172.3, 6, 7.1, 7.2, 91.1, 257.33, 69.1

[56] References Cited

U.S. PATENT DOCUMENTS

| 4,190,495 | 2/1980 | Curtiss, III | 435/172.3 |
| 4,816,397 | 3/1989 | Boss et al. | 435/69.6 |
| 4,946,778 | 8/1990 | Ladner et al. | 435/69.6 |
| 5,223,409 | 6/1993 | Ladner et al. | 435/69.7 |

FOREIGN PATENT DOCUMENTS

| B-27617/88 | 7/1989 | Australia | C12P 21/00 |
| 0 324 162 A1 | 12/1988 | European Pat. Off. | C12N 15/00 |
| WO 88/06630 | 9/1988 | WIPO | C12P 21/00 |
| WO 88/09344 | 12/1988 | WIPO | C07K 13/00 |
| WO 90/02809 | 3/1990 | WIPO | C12P 21/00 |
| WO 90/05144 | 5/1990 | WIPO | C07K 13/00 |
| WO 90/14424 | 11/1990 | WIPO | C12N 15/00 |
| WO 90/14430 | 11/1990 | WIPO | C12P 19/34 |
| WO 90/14443 | 11/1990 | WIPO | C12Q 1/70 |
| WO 91/10737 | 7/1991 | WIPO | C12N 15/13 |
| WO 91/17271 | 11/1991 | WIPO | C12Q 1/70 |
| WO 92/06204 | 4/1992 | WIPO | C12N 15/64 |
| WO 92/09690 | 6/1992 | WIPO | C12N 15/00 |
| WO 92/18619 | 10/1992 | WIPO | C12N 7/01 |

OTHER PUBLICATIONS

Sambrook et al., *Molecular Cloning: A Laboratory Manual*, $2^{nd}$ ed., p. 175 CSH Laboratory Press, 1989, Cold Spring Harbor, NY.
Better et al., *Science*, vol. 240, 1988, pp. 1041–1043.
Skerra et al., *Science*, vol. 240, 1988, pp. 1038–1041.
Präve et al., *Fundamentals of Biotechnology*, 1987 VCH, Weinheim, Germany, pp. 307–308.
Abremski et al., *Cell*, vol. 32, 1983, pp. 1301–1311.
Siest et al., *Clin. Chem.*, vol. 39, 1993, pp. 1573–1589.
Lane et al., *Curr. Opin. Immunol.*, vol. 5, 1993, pp. 268–271 Available to Examiner Only as an Abstract. Applicants' Assistance in Obtaining Full Reference is Requested.
Bass et al., *Proteins, Structure, Function and Genetics* 8:309–314 (1990).
de la Cruz et al., *J. Biol. Chem.* 263(9):4318–4322 (1988).
Huse et al., *Science* 246:1275–1281 (1989).
Kang et al., *Proc. Natl. Acad. Sci. USA* 88:4363–4366 (1991).
McCafferty et al., *Nature* 348:552–554 (1990).
Milstein, F.R.S., *Proc. R. Soc. London* B 239: 1–16 (1990).
Parmley and Smith, *Gene* 73:305–318 (1988).
Short et al., *Nucleic Acids Research* 16(15):7583–7600 (1988).
Smith, *Science* 228:1315–1317 (1985).
Tsunetsugu–Yokota et al., *Gene* 99:261–265 (1991).
Winter and Milstein, *Nature* 349:293–299 (1999).

*Primary Examiner*—James Ketter
*Attorney, Agent, or Firm*—Marshall, O'Toole, Gerstein, Murray & Borun

[57] ABSTRACT

The invention provides methods and kits for producing specific binding pairs (sbp) members. Populations of polypeptide chain components of sbp members are combined to form libraries of sbps displayed by secreted replicable genetic display packages (rgdp). At least one of the polypeptide chains is expressed as a fusion with a component of an rgdp which thereby displays that polypeptide chain at the surface of rgdp. At least one population of polypeptide chains is expressed from nucleic acid which is capable of being packaged using a component of an rgdp, whereby the genetic material of rgdps produced encodes a polypeptide chain. The methods enable production of libraries of multimeric sbp members from a very large number of possible combinations. In one embodiment of the invention a method employs "chain shuffling" in the production of sbp members of desired specificity for a counterpart sbp member. Selection procedures are also described.

31 Claims, 21 Drawing Sheets

Polycombinatorial libraries
Potential library size = $10^{12}$

Polycombinatorial libraries
Potential library size = $10^{12}$

Fig.4.

| | | |
|---|---|---|
| Light chain-gIII-Plasmid | + | Soluble Heavy chain phage |
| Light chain-gIII-Plasmid | + | Soluble Heavy chain phagemid |
| Light chain-gIII-Phagemid | + | Soluble Heavy chain phage |
| Light chain-gIII-Phagemid | + | Soluble Heavy chain plasmid |
| Light chain-gIII-Phage | + | Soluble Heavy chain phagemid |
| Light chain-gIII-Phage | + | Soluble Heavy chain plasmid |
| Soluble Light chain-Plasmid | + | Heavy chain-gIII phage |
| Soluble Light chain-Plasmid | + | Heavy chain-gIII phagemid |
| Soluble Light chain-Phage | + | Heavy chain-gIII phagemid |
| Soluble Light chain-Phage | + | Heavy chain-gIII plasmid |
| Soluble Light chain-Phagemid | + | Heavy chain-gIII plasmid |
| Soluble Light chain-Phagemid | + | Heavy chain-gIII phage |

Soluble combinatorial libraries

Potential library size = $2 \times 10^{13}$ loxP: ATAACTTCGTATA ATGTATGC TATACGAAGTTAT

Fig.7(i).

```
aagcttGCATGCAAATTCTATTTCAAGGAGACAGTCATAATGAAATACCTATTGCCTACGGCAGCCGCTGGATTGTTATT
ACCTGCTGCCAACCAGCGATGGCCCAGTCAGTCAGTGCAGTAGCTTAGTGCAGCCTGCAGCCTGAGGGTCCCGGA
AACTTCCTGTGCAGCCCTCTGGATTCACTTCAGTAGCTTTGGAATGCACTGGGTTGTCAGGCTCAGGAGAAGGGGCTG
GAGTGGGTCGCATATATTAGTAGTGGCAGTAGTACCATCTACTATGCAGACACAGTGAAGGGCGATTCACCATCTCCAG
AGACAATCCAAGAACACCCTGTTCCTGCAAATGACCAGTCAAGT.TGAGGACACGGCCATGTATTACTGTGCAAGAG
ATTACGGGGCTTATTGGGCCAAGGaCcacGTCACCGTTCTCCTCAGCCTCCACCAAGGGCCCATCGTCTTCCCCTG
GCACCCTCCTCCAAGAGCACCTCTGGGGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTCCTACAGTCCTCAGGACTCTACTCC
TCAGCAGCGTGTGACTGTGCCCTCCAGCAGCTTGGGCACCCAGACCTACATCTGCAACGTGAATCACAAGCCCAGCAAC
ACCAAGGTCGACAAGAAAGTTGACACAAAATCTTCATAATCCGGGAGCTTGCATGCAAATTCTATTTCAAGGAGACA
GTCATAATGAAATACCTATTGCCTACGGCAGCCGCTGGATTGTTATTACCTGCTGCCAACCAGCCGATGGCCGACATCga
gctcACCCAGTCTCCAGCAATCATGTCTGCATCTCAGGGACCACATGCAGAAGGTCACCATGACCTGCAGTGCCAGTCAAGTGTAA
GgTACATGaACTGGTtCCaACAGAAGTCAGGCACCTCCCCCAAAAGATGGATTTATGACACATCCAAACTGtCTTCTGGA
GTCCCTGCTCGCTTCAGTGGCAGTGGGTCTGGGACCTCTTACTCTCTCACAATCAGCAGCATGGAGGCTGAAGATGCTGC
CACTTATTACTGCCAGCAGTGGAGTAGTAATCCACTCACGTTCGGTGCTGGGACCAAGCTGgagATCAAACGGACTGTGG
CTGCACCATCTGTCTTCATCTTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGTAACTCCCAGAGAGTGTCAC
AGAGCAGGACAGCAAGGACACAGCACCTACAGCCTCAGCAGCCTGACGCTGAGCAAGCAGACTACGAGAAACACAAAG
TCTACGCCTGCGAAGTCACCCATCAGGGCCTGAGTCGCCCGTCAGTGTTTCCTGTGTGAAATTGTTATCCGCTCACAATCTAGTAAGGA
TCCAGCTCgaattcGTAATCATGGTCATAGCTGTTTCCTGTGTGAAATTGTTATCCGCTCACAATTCCACACAACATACG
AGCCGGAAGCATAAAGTGTAAAGCCTGGGGTGCCTAATGAGTGAGCTAACTCACATTAATTGCGTTGCGCTCACTGCCCG
CTTTCCAGTCGGGAAACCTGTCGTGCCAGCTGCATTAATGAATCGGCCAACGCGCGGGGAGAGGCGGTTTGCGTATTGGG
CGCTCTTCCGCTTCCTCGCTCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCCCCGTTCAGCCCGACCGCTGCGCCTTATCC
GGTAACTATCGTCTTGAGTCCAACCCGGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGGCTACACTAGAAGGACAGTATTTGGTA
TCTGCGCTCTGCTGAAGCCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAGGATCTCAAGAAGATCCTTTGATCTTTTCTACGGG
GTCTGACGCTCAGTGGAACGAAAACTCACGTTAAGGGATTTTGGTCATGAGATTATCAAAAAGGATCTTCACCTAGATCC
TTTTAAATTAAAAATGAAGTTTTAAATCAATCTAAAGTATATATGAGTAAACTTGGTCTGACAGTTACCAATGCTTAATC
```

Fig.7(ii).

```
AGTGAGGCACCTATCTCAGGATCTGTCTATTGTTCATCCATAGTTGCCTGACTCCCGTCGTGTAGATAACTACGAT
ACGGGAGGGCTTACCATCTGCCCCAGTGCTGCAATGATACCCGAGACCCAGCTCACCGGCTCCAGATTTATCAGCAA
TAAACCAGCCAGCCGGAAGGGCGAGCCAGGCAGAAGTGGTCTCTGCAACTTTATCCGCCTCCATCCAGTCTATTAATTGTTGC
CGGGAAGCTAGAGTAAGTAGTTCGCCAGTCAGTTAATAGTTTGCGCAACGTTGTTGCCATTGCCATTGTCTACAGGCATCGTGTGTCACG
CTCGTCGTTTGGTATGCTTCATTCAGCTGCGTTCCCAAGATCAAGGGAGTACATGATCCCCATGTGTGCAAAA
AAGCGGGTTAGCTCCTTCGGTCCTCCGATCGTTGTCAGAAGTAAGTTGGCCCAGTGTTATCATCATGGTTATGGCAGCA
CTGACATAATTCTCTACTGTCATGCCATCCGTAAGATCGTTTCTGTGACTGGTGAGTACTCAACCAAGTCATTCTGAGA
ATAGTGTATGCGGCGACCGAGTTGCTCTGCGGGCGAAACTCTTACCAGGATCTTACCGCTGTGGGTGAGCAAAACAGGAAGGCAAAATGC
TGCTCATCATTGAAAACGTTCTTGCGGGCGAAACTCTTACCAGGATCTTACCGCTGTGGGTGAGCAAAACAGGAAGGCAAAATGC
ACTCGTGCACCCAACTGATCTTCAGCATCTTTACTTTCACCAGCGTTCTGGGTGAGCAAAACAGGAAGGCAAAATGC
CGCAAAAAGGAATAAGGGACACGATACATATTTGAATGTATTTAGAAATAAACAAATAGGCGTTCCGCGCACATTTCCC
AGGGTTATTGTCTCATGAGCGGATCGTCTAAGAACCTGTGAAAACCATTATTATCATGACACATGCAGCTTCCCGAGACGTATCACGAGGCCTT
CGAAAAGTGCCACCTGCGTTTCCGTGATGAGCGTCAAGAACCGTGAAACCATTATCATGACACATGCAGCTTCCCGAGACGTCACAGCTTGTCTGTAAG
TCGTCTCCGGGCGGTTTCCGTGATGAGCGTCAAGAACCGTGAAACCATTATCATGACACATGCAGCTTCCCGAGACGTCACAGCTTGTCTGTAAG
CGGATGCCGGAGCAGACAAGCCGTCAGCGGCGTGTTGGGAAGGGTGTGGGCTGGCTAACTATGGGCA
TCAGAGCAGATTGTACTGAGAGTGCAGCTGCAACTGTTGGGAAGGGTGTGAAATACCGCACAGATGCGTAAGGAGAGAAAATACCGCATCAG
GCGGCCATTCGCCATTCAGCCTGCAAGGCGGATTAAGTTGGGTAACGCCAGGTTTTCCAGTCAAGGAGCGGTGTAACGCCAGGGTAACGCCAGT
AAGGGGGATGCTGCAAGGCGATTAAGTTGGGTAACGCCAGGTTTTCCAGTCAAGGACGAGCGTTGTAAAACGACGGCCAGT
GCC
```

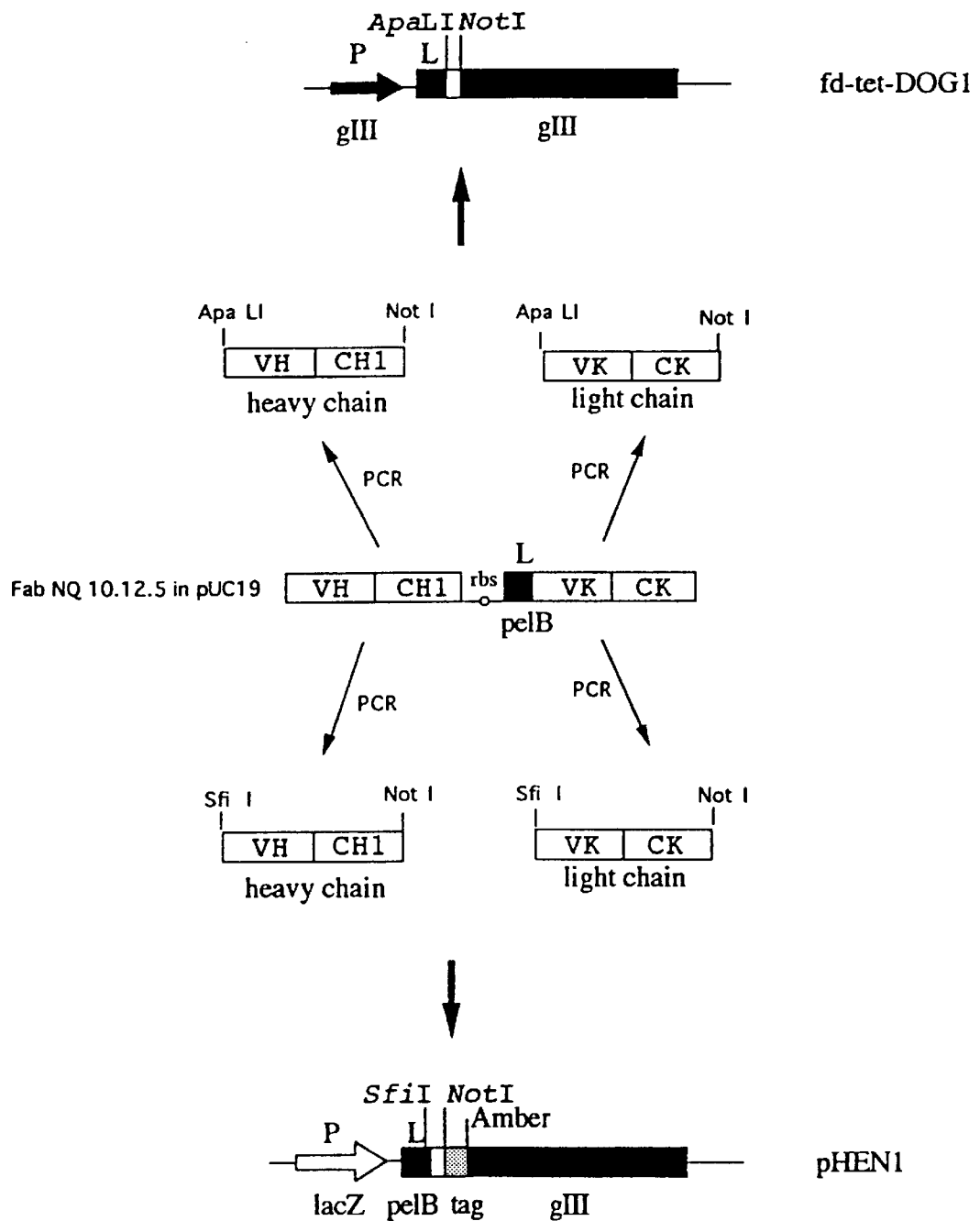

Fig. 9.

```
                                                                              pel B Leader
                        M  K  Y  L  L  P  T  A  A  A  G  L  L  L  L  A  A  Q  P  A  M  A  Q
GCATGCAAATTCTATTTCAAGGAGACAGTCATAATGAAATACCTATTGCCTACGGCAGCCGCTGGATTGTTATTACTCGCGGCCCAGCCGGCCATGGCCCAG
Sph I             RBS                                                                       Sfi I myc Tag
  V  Q  L  Q  V  D  L  E  I  K  R  A  A  A  E  Q  K  L  I  S  E  E  D  L  N  *  *
GTGCAGCTGCAGGTCGACCTCGAGATCAAACGGGCCGCAGAACAAAAACTCATCTCAGAAGAGGATCTGAATTAATAAGAATTC
    Pst I/Sal I/Xho I        Not I                                            Eco RI
```

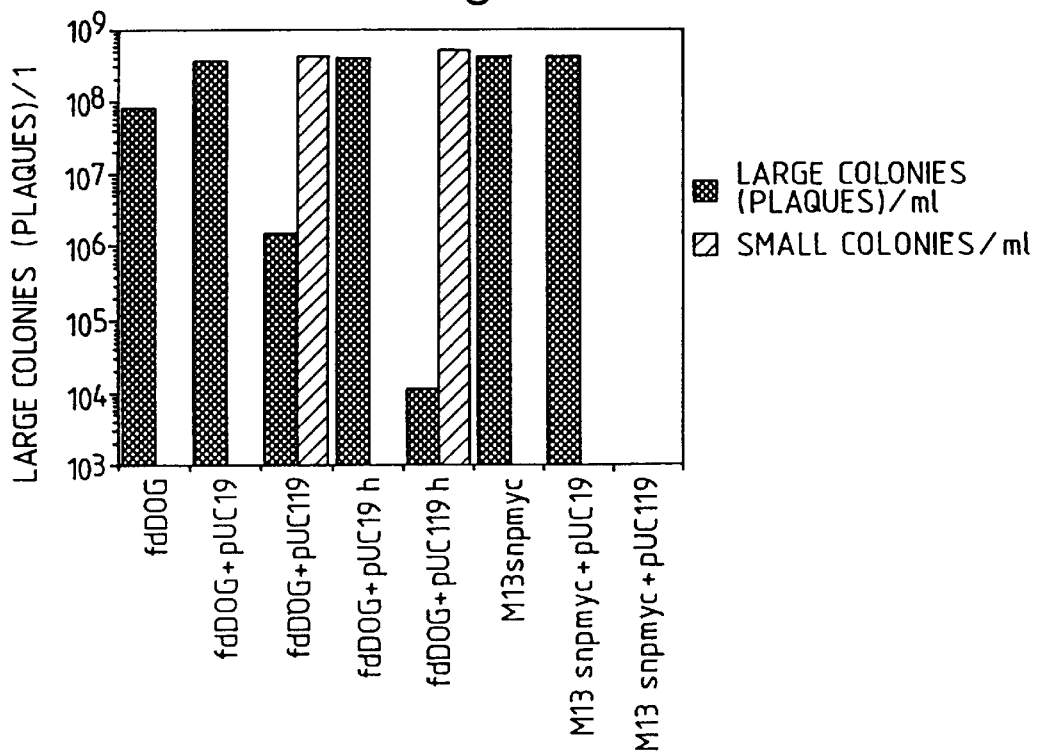
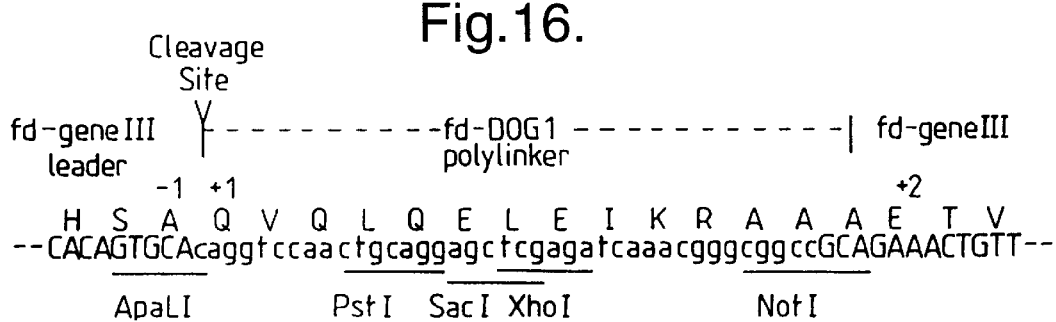

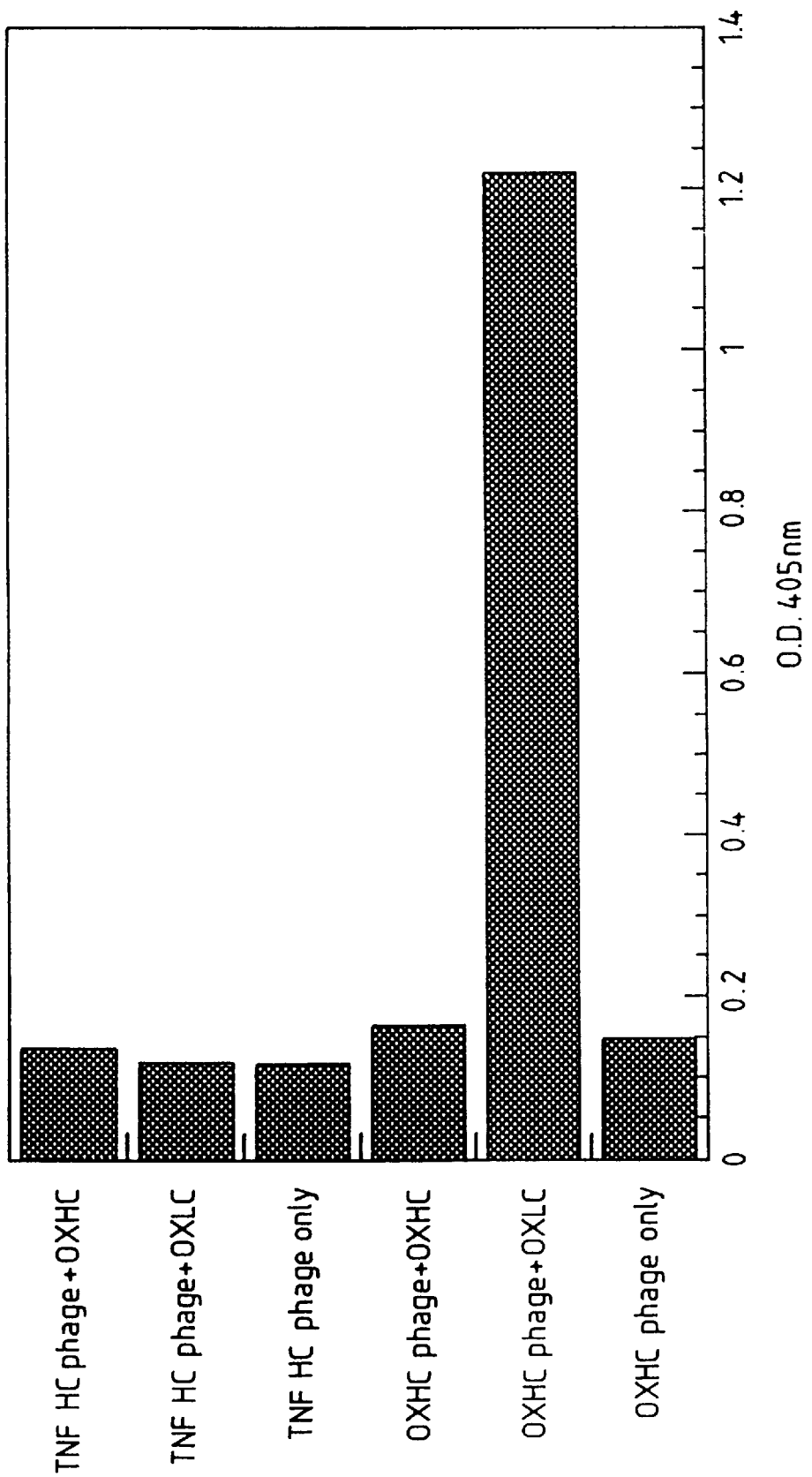

Fig. 13(ii).
Combining CDR-grafted heavy chains with selected light chains
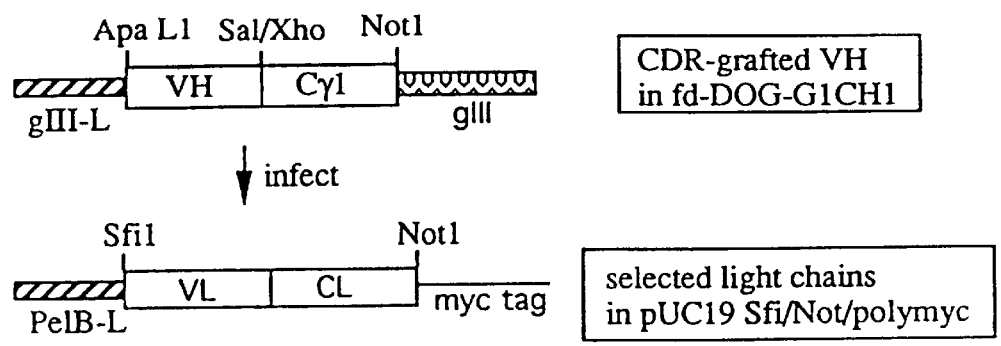
↓ Select for antigen binders
Cloning for soluble Fab expression
↓ PCR heavy chains
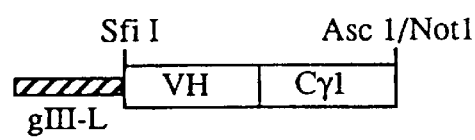
↓ clone into pUC19 to replace F58 heavy chain
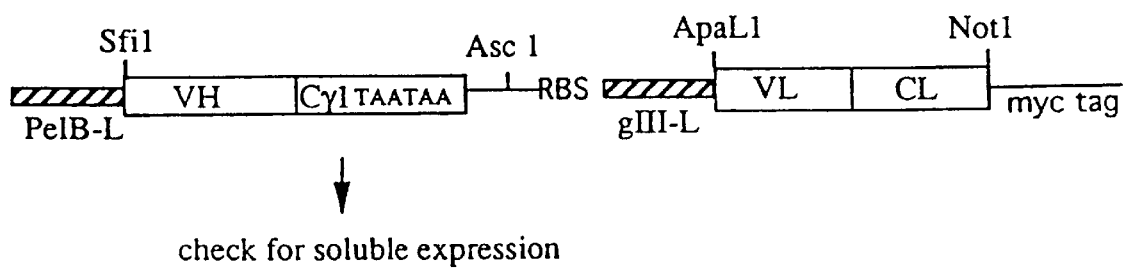
↓
check for soluble expression

Fig.15(i).
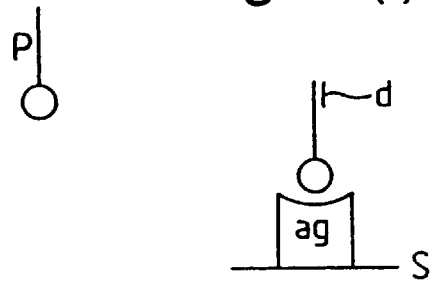
Fig.15(ii).
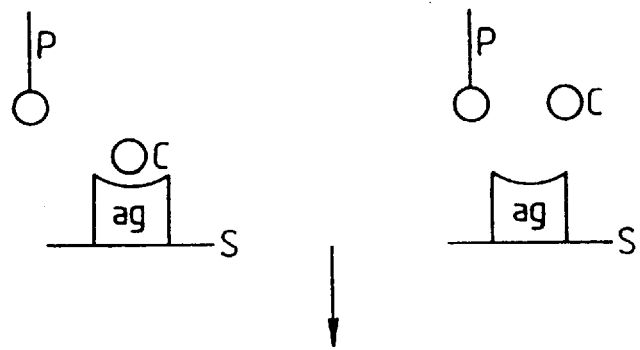

```
·········· PelB leader ——————|-------- pHEN1 polylinker -----
                           -1 +1
             L  L  A  A  Q  P  A  M  A  Q  V  Q  L  Q  V  D  L  E  I  K  R
       --TTACTCGCGGCCCAGccggccatggcccaggtgcagctgcaggtcgacctcgagatcaaacgg
                  ―――――    ―――――          ―――         ―――     ―――
                   SfiI     NcoI           PstI        SalI     XhoI -------|------- c-myc tag --------|   |--- fd-gene III ----

A  A  A  E  Q  K  L  I  S  E  E  D  L  N  G  A  A (E) T  V  E
        gcggccGCAGAACAAAAACTCATCTCAGAAGAGGATCTGAATGGGGCCGCATAGACTGTTGAA--
        ―――――                                                amber
         NotI
```

Fig.19.
Fab
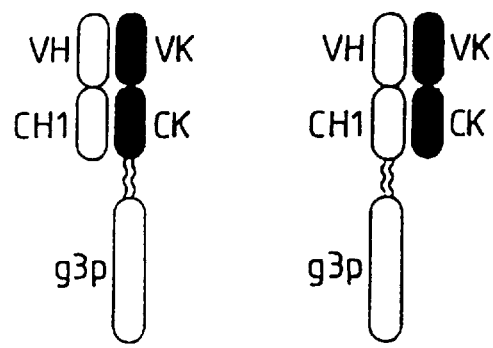
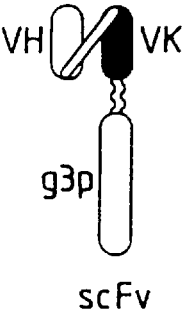
scFv

METHODS FOR PRODUCING MEMBERS OF SPECIFIC BINDING PAIRS

The present invention relates to methods for producing members of specific binding pairs. The present invention also relates to the biological binding molecules produced by these methods.

Owing to their high specificity for a given antigen, the advent of monoclonal antibodies (Kohler, G. and Milstein C; 1975 Nature 256: 495) represented a significant technical break-through with important consequences both scientifically and commercially.

Monoclonal antibodies are traditionally made by establishing an immortal mammalian cell line which is derived from a single immunoglobulin producing cell secreting one form of a biologically functional antibody molecule with a particular specificity. Because the antibody-secreting mammalian cell line is immortal, the characteristics of the antibody are reproducible from batch to batch. The key properties of monoclonal antibodies are their specificity for a particular antigen and the reproducibility with which they can be manufactured.

Structurally, the simplest antibody (IgG) comprises four polypeptide chains, two heavy (H) chains and two light (L) chains inter-connected by disulphide bonds (see FIG. 14). The light chains exist in two distinct forms called kappa (K) and lambda ( ). Each chain has a constant region (C) and a variable region (V). Each chain is organized into a series of domains. The light chains have two domains, corresponding to the C region and the other to the V region. The heavy chains have four domains, one corresponding to the V region and three domains (1,2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognising the antigen and providing an antigen binding site (ABS). In even more detail, each V region is made up from three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation and selection.

It has been shown that the function of binding antigens can be performed by fragments of a whole antibody. Example binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward, E. S. et al., Nature 341, 544–546 (1989) which consists of a VH domain; (v) isolated CDR regions; and (vi) F(ab')$_2$ fragments, a bivalent fragment comprising two Fab fragments linked by a disulphide bridge at the hinge region.

Although the two domains of the Fv fragment are coded for by separate genes, it has proved possible to make a synthetic linker that enables them to be made as a single protein chain (known as single chain Fv (scFv); Bird, R. E. et al., Science 242, 423–426 (1988) Huston, J. S. et al., Proc. Natl. Acad. Sci., USA 85, 5879–5883 (1988)) by recombinant methods. These scFv fragments were assembled from genes from monoclonals that had been previously isolated.

Whilst monoclonal antibodies, their fragments and derivatives have been enormously advantageous, there are nevertheless a number of limitations associated with them.

Firstly, the therapeutic applications of monoclonal antibodies produced by human immortal cell lines holds great promise for the treatment of a wide range of diseases (Clinical Applications of Monoclonal Antibodies. Edited by E. S. Lennox. British Medical Bulletin 1984. Publishers Churchill Livingstone). Unfortunately, immortal antibody-producing human cell lines are very difficult to establish and they give low yields of antibody (approximately 1 µg/ml). In contrast, equivalent rodent cell lines yield high amounts of antibody (approximately 100 µg/ml). However, the repeated administration of these foreign rodent proteins to humans can lead to harmful hypersensitivity reactions. In the main therefore, these rodent-derived monoclonal antibodies have limited therapeutic use.

Secondly, a key aspect in the isolation of monoclonal antibodies is how many different clones of antibody producing cells with different specificities, can be practically established and sampled compared to how many theoretically need to be sampled in order to isolate a cell producing antibody with the desired specificity characteristics (Milstein, C., Royal Soc. Croonian Lecture, Proc. R. Soc. London B. 239; 1–16, (1990)). For example, the number of different specificities expressed at any one time by lymphocytes of the murine immune system is thought to be approximately $10^7$ and this is only a small proportion of the potential repertoire of specificities. However, during the isolation of a typical antibody producing cell with a desired specificity, the investigator is only able to sample $10^3$ to $10^4$ individual specificities. The problem is worse in the human, where one has approximately $10^{12}$ lymphocyte specificities, with the limitation on sampling of $10^3$ or $10^4$ remaining.

This problem has been alleviated to some extent in laboratory animals by the use of immunisation regimes. Thus, where one wants to produce monoclonal antibodies having a specificity against a particular epitope, an animal is immunised with an immunogen expressing that epitope. The animal will then mount an immune response against the immunogen and there will be a proliferation of lymphocytes which have specificity against the epitope. Owing to this proliferation of lymphocytes with the desired specificity, it becomes easier to detect them in the sampling procedure. However, this approach is not successful in all cases, as a suitable immunogen may not be available. Furthermore, where one wants to produce human monoclonal antibodies (eg for therapeutic administration as previously discussed), such an approach is not practically, or ethically, feasible.

In the last few years, these problems have in part, been addressed by the application of recombinant DNA methods to the isolation and production of e.g. antibodies and fragments of antibodies with antigen binding ability, in bacteria such as *E. coli*.

This simple substitution of immortalised cells with bacterial cells as the 'factory', considerably simplifies procedures for preparing large amounts of binding molecules. Furthermore, a recombinant production system allows scope for producing tailor-made antibodies and fragments thereof. For example, it is possible to produce chimaeric molecules with new combinations of binding and effector functions, humanised antibodies (e.g. murine variable regions combined with human constant domains or murine-antibody CDRs grafted onto a human FR) and novel antigen-binding molecules. Furthermore, the use of polymerase chain reaction (PCR) amplification (Saiki, R. K., et al., Science 239, 487–491 (1988)) to isolate antibody producing sequences from cells (e.g. hybridomas and B cells) has great potential for speeding up the timescale under which specificities can be isolated. Amplified VH and VL genes are cloned directly into vectors for expression in bacteria or mammalian cells (Orlandi, R., et al., 1989, Proc. Natl. Acad. Sci., USA 86, 3833–3837; Ward, E. S., et al., 1989 supra; Larrick, J. W., et al., 1989, Biochem. Biophys. Res. Commun. 160, 1250–1255; Sastry, L. et al., 1989, Proc. Natl. Acad. Sci., USA., 86, 5728–5732). Soluble antibody fragments secreted from bacteria are then screened for binding activities.

However, like the production system based upon immortalised cells, the recombinant production system still suffers from the selection problems previously discussed and therefore relies on animal immunization to increase the proportion of cells with desired specificity. Furthermore, some of these techniques can exacerbate the screening problems. For example, large separate H and L chain libraries have been produced from immunized mice and combined together in a random combinatorial manner prior to screening (Huse, W. D. et al., 1989, Science 246, 1275–1281, WO90/14443; WO90/14424 and WO90/14430). Crucially however, the information held within each cell, namely the original pairing of one L chain with one H chain, is lost. This loses some of the advantage gained by using immunization protocols in the animal. Currently, only libraries derived from single VH domains (dabs; Ward, E. S., et al., 1989, supra.) do not suffer this drawback. However, because not all antibody VH domains are capable of binding antigen, more have to be screened. In addition, the problem of directly screening many different specificities in prokaryotes remains to be solved.

Thus, there is a need for a screening system which ameliorates or overcomes one or more of the above or other problems. The ideal system would allow the sampling of very large numbers of specificities (eg $10^6$ and higher), rapid sorting at each cloning round, and rapid transfer of the genetic material coding for the binding molecule from one stage of the production process, to the next stage.

The most attractive candidates for this type of screening, would be prokaryotic organisms (because they grow quickly, are relatively simple to manipulate and because large numbers of clones can be created) which express and display at their surface a functional binding domain eg. an antibody, receptor, enzyme etc. In the UK patent GB 2137631B methods for the co-expression in a single host cell of the variable H and L chain genes of immunoglobulins were disclosed. However, the protein was expressed intracellularly and was insoluble. Further, the protein required extensive processing to generate antibody fragments with binding activity and this generated material with only a fraction of the binding activity expected for antibody fragments at this concentration. It has already been shown that antibody fragments can be secreted through bacterial membranes with the appropriate signal peptide (Skerra, A. and Pluckthun, A. 1988 Science 240 1038–1040; Better, M et al 1988, Science 240 1041–1043) with a consequent increase in the binding activity of antibody fragments. These methods require screening of individual clones for binding activity in the same way as do mouse monoclonal antibodies.

It has not been shown however, how a functional binding domain eg an antibody, antibody fragment, receptor, enzyme etc can be held on the bacterial surface in a configuration which allows sampling of say its antigen binding properties and selection for clones with desirable properties. In large part, this is because the bacterial surface is a complex structure, and in the gram-negative organisms there is an outer wall which further complicates the position. Further, it has not been shown that e.g., an antibody domain will fold correctly when expressed as a fusion with a surface protein of bacteria or bacteriophage.

Bacteriophage are attractive prokaryote related organisms for this type of screening. In general, their surface is a relatively simple structure, they can be grown easily in large numbers, they are amenable to the practical handling involved in many potential mass screening programmes, and they carry genetic information for their own synthesis within a small, simple package. The difficulty has been to practically solve the problem of how to use bacteriophages in this manner. A Genex Corporation patent application number WO88/06630 has proposed that the bacteriophage lambda would be a suitable vehicle for the expression of antibody molecules, but they do not provide a teaching which enables the general idea to be carried out. For example WO88/06630 does not demonstrate that any sequences: (a) have been expressed as a fusion with gene V; (b) have been expressed on the surface of lambda; and (c) have been expressed so that the protein retains biological activity. Furthermore there is no teaching on how to screen for suitable fusions. Also, since the lambda virions are assembled within the cell, the fusion protein would be expressed intracellularly and would be predicted to be inactive. Bass et al., in December 1990 describe deleting part of gene III of the filamentous bacteriophage M13 and inserting the coding sequence for human growth hormone (hGH) into the N-terminal site of the gene. The growth hormone displayed by M13 was shown to be functional. (Bass, S., et al. Proteins, Structure, Function and Genetics (1990) 8: 309–314). A functional copy of gene III was always present in addition, when this fusion was expressed. A Protein Engineering Corporation patent application WO90/02809 proposes the insertion of the coding sequence for bovine pancreatic trypsin inhibitor (BPTI) into gene VIII of M13. However, the proposal was not shown to be operative. For example, there is no demonstration of the expression of BPTI sequences as fusions with protein VIII and display on the surface of M13. Furthermore this document teaches that when a fusion is made with gene III, it is necessary to use a second synthetic copy of gene III, so that some unaltered gene III protein will be present. The embodiments of the present application do not do this. In embodiments where phagemid is rescued with M13K07 gene III deletion phage, there is no unaltered gene III present.

WO90/02809 also teaches that phagemids that do not contain the full genome of M13 and require rescue by coinfection with helper phage are not suitable for these purposes because coinfection could lead to recombination.

In all embodiments where the present applicants have used phagemids, they have used a helper phage and the only sequences derived from filamentous bacteriophage in the phagemids are the origin of replication and gene III sequences.

WO90/02809 also teaches that their process needed information such as nucleotide sequence of the starting molecule and its three-dimensioned structure. The use of a pre-existing repertoire of binding molecules to select for a binding member, such as is disclosed herein, for example using an immunoglobulin gene repertoire of animals, was not disclosed. Further, they do not discuss favouring variegation of their binding molecules in natural blocks of variation such as CDRs of immunoglobulins, in order to favour generation of improved molecules and prevent unfavourable variations. WO90/02809 also specifically excluded the application of their process to the production of scFv molecules.

In each of the above discussed patents (WO88/06630 and WO90/02809), the protein proposed for display is a single polypeptide chain. There is no disclosure of a method for the display of a dimeric molecule by expression of one monomer as a fusion with a capsid protein and the other protein in a free form.

Another disclosure published in May 1991 describes the insertion into gene VIII of M13, the coding sequences for one of the two chains of the Fab portion of an antibody with co-expression of the other from a plasmid. The two chains were demonstrated as being expressed as a functional Fab fragment on the surface of the phage (Kang A. S. et al., (1991) Proc. Natl. Acad. Sci, USA, 88 p4363–4366). No disclosure was made of the site of insertion into gene VIII and the assay for pAb binding activity by ELISA used a reagent specific for antibody L chain rather than for phage. A further disclosure published in March 1991 describes the insertion of a fragment of the AIDS virus protein gag into the N-terminal portion of gene III of the bacteriophage fd. The expression of the gag protein fragment was detected by immunological methods, but it was not shown whether or not the protein was expressed in a functional form (Tsunetsugu-Yokota Y et al. (1991) Gene 99 p261–265).

The problem of how to use bacteriophages in this way is in fact a difficult one. The protein must be inserted into the phage in such a way that the integrity of the phage coat is not undermined, and the protein itself should be functional retaining its biological activity with respect to antigen binding. Thus, where the protein of choice is an antibody, it should fold efficiently and correctly and be presented for antigen binding. Solving the problem for antibody molecules and fragments would also provide a general method for any biomolecule which is a member of a specific binding pair e.g. receptor molecules and enzymes.

Surprisingly, the applicants have been able to construct a bacteriophage that expresses and displays at its surface a large biologically functional binding molecule (e.g., antibody fragments, and enzymes and receptors) and which remains intact and infectious. This is described in WO 92/01047, the disclosure of which is herein incorporated by reference. Readers of the present document are urged to consult WO 92/01047 for detailed explanation of many of the procedures used in the experiments described herein. The applicants have called the structure which comprises a virus particle and a binding molecule displayed at the viral surface a 'package'. Where the binding molecule is an antibody, an antibody derivative or fragment, or a domain that is homologous to an immunoglobulin domain, the applicants call the package a 'phage antibody' (pAb). However, except where the context demands otherwise, where the term phage antibody is used generally, it should also be interpreted as referring to any package comprising a virus particle and a biologically functional binding molecule displayed at the viral surface.

pAbs have a range of applications in selecting antibody genes encoding antigen binding activities. For example, pAbs could be used for the cloning and rescue of hybridomas (Orlandi, R., et al (1989) PNAS 86 p3833–3837), and in the screening of large combinatorial libraries (such as found in Huse, W. D. et al., 1989, Science 246, 1275–1281). In particular, rounds of selection using pAbs may help in rescuing the higher affinity antibodies from the latter libraries. It may be preferable to screen small libraries derived from antigen-selected cells (Casali, P., et al., (1986) Science 234 p476–479) to rescue the original VH/VL pairs comprising the Fv region of an antibody. The use of pAbs may also allow the construction of entirely synthetic antibodies. Furthermore, antibodies may be made which have some synthetic sequences e.g. CDRs, and some naturally derived sequences. For example, V-gene repertoires could be made in vitro by combining unrearranged V genes, with D and J segments. Libraries of pAbs could then be selected by binding to antigen, hypermutated in vitro in the antigen-binding loops or V domain framework regions, and subjected to further rounds of selection and mutagenesis.

As previously discussed, separate H and L chain libraries lose the original pairing between the chains. It is difficult to make and screen a large enough library for a particularly advantageous combination of H and L chains.

For example, in a mouse there are approximately $10^7$ possible H chains and $10^7$ possible L chains. Therefore, there are $10^{14}$ possible combinations of H and L chains, and to test for anything like this number of combinations one would have to create and screen a library of about $10^{14}$ clones.

The present invention provides approaches which ameliorate this problem.

In one approach as large a library as is practically possible is created which expresses as many of the $10^{14}$ potential combinations as possible. However, by virtue of the expression of the H and L chains on the surface of the phage, it is reasonably practicable to select the desired combination, from all the generated combinations by affinity techniques (see later for description of selection formats).

In an approach (called a poly combinatorial approach by the present applicants), a large library is created from two smaller libraries for selection of the desired combination. The approach involves the creation of: (i) a first library of say $10^7$ e.g. H chains which are displayed on a bacteriophage (as a fusion with the protein encoded by gene III) which is resistant to e.g. tetracycline; and (ii) a second library of say $10^7$ e.g. L chains in which the coding sequences for these light chains are within a plasmid vector and are expressed in the periplasmic space of a host bacterium. The first library is then used to infect the bacteria containing the second library to provide $10^{14}$ combinations of H and L chains on the surface of the resulting phage in the bacterial supernatant.

The advantage of this approach is that two separate libraries of eg $10^7$ are created in order to produce $10^{14}$ combinations. Creating a $10^7$ library is a practical possibility.

The $10^{14}$ combinations are then subjected to selection (see later for description of selection formats) as disclosed by the present application. This selection will then produce a population of phages displaying a particular combination of H and L chains having the desired specificity. The phages selected however, will only contain DNA encoding one partner of the paired H and L chains. The sample eluate containing the population is then divided into two portions. A first portion is grown on e.g. tetracycline plates to select those bacteriophage containing DNA encoding H chains which are involved in the desired antigen binding. A second portion is grown on e.g. ampicillin plates to select those bacteriophage containing phagemid DNA encoding L chains which are involved in the desired antigen binding. A set of colonies from individually isolated clones e.g. from the tetracycline plates are then used to infect specific colonies e.g. from the ampicillin plates. This results in bacteriophage expressing specific combinations of H and L chains which can then be assayed for antigen binding.

In another approach (called a hierarchical dual combinational approach or chain shuffling by the present applicants), an individual colony from either the H or L chain clone selected by growth on the antibiotic plates, is used to infect a complete library of clones encoding the other chain (H or L). Selection is as described above. This favours isolation of the most favourable combination.

Phagemids have been mentioned above. The applicants have realised and demonstrated that in many cases phagemids will be preferred to phage for cloning antibodies because it is easier to use them to generate more comprehensive libraries of the immune repertoire. This is because the phagemid DNA is approximately 100 times more efficient than bacteriophage DNA in transforming bacteria (see example 19 of WO 92/01047). Also, the use of phagemids gives the ability to vary the number of gene III binding molecule fusion proteins displayed on the surface of the bacteriophage (see example 17 of WO 92/01047). For example, in a system comprising a bacterial cell containing a phagemid encoding a gene III fusion protein and infected with a helper phage, induction of expression of the gene III fusion protein to different extents, will determine the number of gene III fusion proteins present in the space defined between the inner and outer bacterial membranes following superinfection. This will determine the ratio of gene III fusion protein to native gene III protein displayed by the assembled phage.

Expressing a single fusion protein per virion may aid selection of antibody specificities on the basis of affinity by avoiding the 'avidity' effect where a phage expressing two copies of a low affinity antibody would have the same apparent affinity as a phage expressing one copy of a higher affinity antibody. In some cases however, it will be important to display all the gene III molecules derived by superinfection of cells containing phagemids to have fusions (e.g. for selecting low affinity binding molecules or improving sensitivity on ELISA). One way to do this is to superinfect with a bacteriophage which contains a defective gene III. The applicants have therefore developed and used a phage which is deleted in gene III, described in WO 92/01047.

The demonstration that a functional antigen-binding domain can be displayed on the surface of phage, has implications beyond the construction of novel antibodies. For example, if other protein domains can be displayed at the surface of a phage, phage vectors could be used to clone and select genes by the binding properties of the displayed protein. Furthermore, variants of proteins, including epitope libraries built into the surface of the protein, could be made and readily selected for binding activities. In effect, other protein architectures might serve as "nouvelle" antibodies.

The technique provides the possibility of building antibodies from first principles, taking advantage of the structural framework on which the antigen binding loops fold. In general, these loops have a limited number of conformations which generate a variety of binding sites by alternative loop combinations and by diverse side chains. Recent successes in modelling antigen binding sites augurs well for de novo design. In any case, a high resolution structure of the antigen is needed. However, the approach is attractive for making e.g. catalytic antibodies, particularly for small substrates. Here side chains or binding sites for prosthetic groups might be introduced, not only to bind selectively to the transition state of the substrate, but also to participate directly in bond making and breaking. The only question is whether the antibody architecture, specialised for binding, is the best starting point for building catalysts. Genuine enzyme architectures, such as the triose phosphate isomerase (TIM) barrel, might be more suitable. Like antibodies, TIM enzymes also have a framework structure (a barrel of β-strands and α-helices) and loops to bind substrate. Many enzymes with a diversity of catalytic properties are based on this architecture and the loops might be manipulated independently on the frameworks for design of new catalytic and binding properties. The phage selection system as provided by the present disclosure can be used to select for antigen binding activities and the CDR loops thus selected, used on either an antibody framework or a TIM barrel framework. Loops placed on a e.g. a TIM barrel framework could be further modified by mutagenesis and subjected to further selection. Thus, there is no need to select for high affinity binding activities in a single step. The strategy of the immune system, in which low affinity evolves to high affinity seems more realistic and can be mimicked using this invention.

One class of molecules that could be useful in this type of application are receptors. For example, a specific receptor could be displayed on the surface of the phage such that it would bind its ligand. The receptor could then be modified by, for example, in vitro mutagenesis and variants having higher binding affinity for the ligand selected. The selection may be carried out according to one or more of the formats described below.

Alternatively, the phage-receptor could be used as the basis of a rapid screening system for the binding of ligands, altered ligands, or potential drug candidates. The advantages of this system namely of simple cloning, convenient expression, standard reagents and easy handling makes the drug screening application particularly attractive. In the context of this discussion, receptor means a molecule that binds a specific, or group of specific, ligand(s). The natural receptor could be expressed on the surface of a population of cells, or it could be the extracellular domain of such a molecule (whether such a form exists naturally or not), or a soluble molecule performing a natural binding function in the plasma, or within a cell or organ.

Another possibility, is the display of an enzyme molecule or active site of an enzyme molecule on the surface of a phage (see examples 11,12,30,31,32 and 36 of WO 92/01047). Once the phage enzyme is expressed, it can be selected by affinity chromatography, for instance on columns derivatized with transition state analogues. If an enzyme with a different or modified specificity is desired, it may be possible to mutate an enzyme displayed as a fusion on bacteriophage and then select on a column derivatised with an analogue selected to have a higher affinity for an enzyme with the desired modified specificity.

Although throughout this application, the applicants discuss the possibility of screening for higher affinity variants of pAbs, they recognise that in some applications, for example low affinity chromatography (Ohlson, S. et al Anal. Biochem. 169, p204–208 (1988)), it may be desirable to isolate lower affinity variants.

pAbs also allow the selection of antibodies for improved stability. It has been noted for many antibodies, that yield and stability are improved when the antibodies are expressed at 30° C. rather than 37° C. If pAbs are displayed at 37° C., only those which are stable will be available for affinity selection. When antibodies are to be used in vivo for therapeutic or diagnostic purposes, increased stability would extend the half-life of antibodies in circulation.

Although stability is important for all antibodies and antibody domains selected using phage, it is particularly important for the selection of Fv fragments which are formed by the non-covalent association of VH and VL fragments. Fv fragments have a tendency to dissociate and have a much reduced half-life in circulation compared to whole antibodies. Fv fragments are displayed on the surface of phage, by the association of one chain expressed as a gene III protein fusion with the complementary chain expressed as a soluble fragment. If pairs of chains have a high tendency to dissociate, they will be much less likely to be selected as pAbs. Therefore, the population will be enriched for pairs which do associate stably. Although dissociation is less of a problem with Fab fragments, selection would also occur for Fab fragments which associate stably. pAbs allow selection for stability to protease attack, only those pAbs that are not cleaved by proteases will be capable of binding their ligand and therefore populations of phage will be enriched for those displaying stable antibody domains.

The technique of displaying binding molecules on the phage surface can also be used as a primary cloning system. For example, a cDNA library can be constructed and inserted into the bacteriophage and this phage library screened for the ability to bind a ligand. The ligand/binding molecule combination could include any pair of molecules with an ability to specifically bind to one another e.g. receptor/ligand, enzyme/substrate (or analogue), nucleic acid binding protein/nucleic acid etc. If one member of the complementary pair is available, this may be a preferred way of isolating a clone for the other member of the pair.

It will often be necessary to increase the diversity of a population of genes cloned for the display of their proteins on phage or to mutate an individual nucleotide sequence. Although in vitro or in vivo mutagenesis techniques could be used for either purpose, a particularly suitable method would be to use mutator strains. A mutator strain is a strain which contains a genetic defect which causes DNA replicated within it to be mutated with respect to its parent DNA. Hence if a population of genes as gene III fusions is introduced into these strains it will be further diversified and can then be transferred to a non-mutator strain, if desired, for display and selection.

Targeted Gene Transfer

A useful and novel set of applications makes use of the binding protein on the phage to target the phage genome to a particular cell or group of cells. For example, a pAb specific for a cell surface molecule could be used to bind to the target cell via the surface molecule. The phage could then be internalised, either through the action of the receptor itself or as the result of another event (e.g. an electrical discharge such as in the technique of electroporation). The phage genome would then be expressed if the relevant control signals (for transcription and translation and possibly replication) were present. This would be particularly useful if the phage genome contained a sequence whose expression was desired in the target cell (along with the appropriate expression control sequences). A useful sequence might confer antibiotic resistance to the recipient cell or label the cell by the expression of its product (e.g. if the sequence expressed a detectable gene product such as a luciferase, see White, M, et al, Techniques 2(4), p194–201 (1990)), or confer a particular property on the target cell (e.g. if the target cell was a tumour cell and the new sequence directed the expression of a tumour suppressing gene), or express an antisense construct designed to turn off a gene or set of genes in the target cell, or a gene or gene product designed to be toxic to the target cell.

Alternatively, the sequence whose expression is desired in the target cell can be encoded on a phagemid. The phagemid DNA may then be incorporated into a phage displaying an antibody specific for a cell surface receptor. For example, incorporation may be by superinfection of bacteria containing the phagemid, with a helper phage whose genome encodes the antibody fragment specific for the target cell. The package is then used to direct the phagemid to the target cell.

This technique of "targeted gene transfer" has a number of uses in research and also in therapy and diagnostics. For example, gene therapy often aims to target the replacement gene to a specific cell type that is deficient in its activity. Targetting pAbs provide a means of achieving this.

In diagnostics, phage specific for particular bacteria or groups of bacteria have been used to target marker genes, e.g. luciferase, to the bacterial host (sec, for example, Ulitzer, S., and Kuhn, J., EPA 85303913.9). If the host range of the phage is appropriate, only those bacteria that are being tested for, will be infected by the phage, express the luciferase gene and be detected by the light they emit. This system has been used to detect the presence of Salmonella. One major problem with this approach is the initial isolation of a bacteriophage with the correct host range and then the cloning of a luciferase gene cassette into that phage, such that it is functional. The pAb system allows the luciferase cassette to be cloned into a well characterised system (filamentous phage) and allows simple selection of an appropriate host range, by modifying the antibody (or other binding molecule) specificity that the pAb encodes.

The present applicants have also been able to develop novel selection systems and assay formats which depend on the unique properties of these replicable genetic display packages e.g. pAbs.

TERMINOLOGY

Much of the terminology discussed in this section has been mentioned in the text where appropriate.

Specific Binding Pair (sbp)

This describes a pair of molecules (each being a member of a specific binding pair) which are naturally derived or synthetically produced. One of the pair of molecules, has an area on its surface, or a cavity which specifically binds to, and is therefore defined as complementary with a particular spatial and polar organisation of the other molecule, so that the pair have the property of binding specifically to each other. Examples of types of specific binding pairs are antigen-antibody, biotin-avidin, hormone-hormone receptor, receptor-ligand, enzyme-substrate, lgG-protein A.

Multimeric Member

This describes a first polypeptide which will associate with at least a second polypeptide, when the polypeptides are expressed in free form and/or on the surface of a substrate. The substrate may be provided by a bacteriophage. Where there are two associated polypeptides, the associated polypeptide complex is a dimer, where there are three, a trimer etc. The dimer, trimer, multimer etc. or the multimeric member may comprise a member of a specific binding pair.

Example multimeric members are heavy domains based on an immunoglobulin molecule, light domains based on an immunoglobulin molecule, T-cell receptor subunits.

Replicable Genetic Display Package (Rgdp)

This describes a biological particle which has genetic information providing the particle with the ability to replicate. The particle can display on its surface at least part of a polypeptide. The polypeptide can be encoded by genetic information native to the particle and/or artificially placed into the particle or an ancestor of it. The displayed polypeptide may be any member of a specific binding pair e.g. heavy or light chain domains based on an immunoglobulin molecule, an enzyme or a receptor etc.

The particle may be a virus e.g. a bacteriophage such as fd or M13.

Package

This describes a replicable genetic display package in which the particle is displaying a member of a specific binding pair at its surface. The package may be a bacteriophage which displays an antigen binding domain at its surface. This type of package has been called a phage antibody (pAb).

Antibody

This describes an immunoglobulin whether natural or partly or wholly synthetically produced. The term also covers any protein having a binding domain which is homologous to an immunoglobulin binding domain. These proteins can be derived from natural sources, or partly or wholly synthetically produced.

Example antibodies are the immunoglobulin isotypes and the Fab, $F(ab^1)_2$, scFv, Fv, dAb, Fd fragments.

Immunoglobulin Superfamily

This describes a family of polypeptides, the members of which have at least one domain with a structure related to that of the variable or constant domain of immunoglobulin molecules. The domain contains two β-sheets and usually a conserved disulphide bond (see A. F. Williams and A. N. Barclay 1988 Ann. Rev Immunol. 6 381–405).

Example members of an immunoglobulin superfamily are CD4, platelet derived growth factor receptor (PDGFR), intercellular adhesion molecule. (ICAM). Except where the context otherwise dictates, reference to immunoglobulins and immunoglobulin homologs in this application includes members of the immunoglobulin superfamily and homologs thereof.

Homologs

This term indicates polypeptides having the same or conserved residues at a corresponding position in their primary, secondary or tertiary structure. The term also extends to two or more nucleotide sequences encoding the homologous polypeptides.

Examples of homologous peptides are the immunoglobulin isotypes.

Functional

In relation to a sbp member displayed on the surface of a rgdp, functionally means that the sbp member is presented in a folded form in which its specific binding domain for its complementary sbp member is the same or closely analogous to its native configuration, whereby it exhibits similar specificity with respect to the complementary sbp member. In this respect, it differs from the peptides of Smith et al, supra, which do not have a definite folded configuration and can assume a variety of configurations determined by the complementary members with which they may be contacted.

Genetically Diverse Population

In connection with sbp members or polypeptide components thereof, this is referring not only to diversity that can exist in the natural population of cells or organisms, but also diversity that can be created by artificial mutation in vitro or in vivo.

Mutation in vitro may for example, involve random mutagenesis using oligonucleotides having random mutations of the sequence desired to be varied. In vivo mutagenesis may for example, use mutator strains of host microorganisms to harbour the DNA (see Example 38 of WO 92/01047). The word "population" itself may be used to denote a plurality of e.g. polypeptide chains, which are not genetically diverse i.e. they are all the same.

Domain

A domain is a part of a protein that is folded within itself and independently of other parts of the same protein and independently of a complementary binding member.

Folded Unit

This is a specific combination of an a-helix and/or β-strand and/or β-turn structure. Domains and folded units contain structures that bring together amino acids that are not adjacent in the primary structure.

Free Form

This describes the state of a polypeptide which is not displayed by a replicable genetic display package.

Conditionally Defective

This describes a gene which does not express a particular polypeptide under one set of conditions, but expresses it under another set of conditions. An example, is a gene containing an amber mutation expressed in non-suppressing or suppressing hosts respectively.

Alternatively, a gene may express a protein which is defective under one set of conditions, but not under another set. An example is a gene with a temperature sensitive mutation.

Suppressible Translational Stop Codon

This describes a codon which allows the translation of nucleotide sequences downstream of the codon under one set of conditions, but under another set of conditions translation ends at the codon. Example of suppressible translational stop codons are the amber, ochre and opal codons.

Mutator Strain

This is a host cell which has a genetic defect which causes DNA replicated within it to be mutated with respect to its parent DNA. Example mutator strains are NR9046mutD5 and NR9046 mut T1 (see Example 38).

Helper Phage

This is a phage which is used to infect cells containing a defective phage genome and which functions to complement the defect. The defective phage genome can be a phagemid or a phage with some function encoding gene sequences removed. Examples of helper phages are M13KO7, M13K07 gene III no. 3; and phage displaying or encoding a binding molecule fused to a capsid protein.

Vector

This is a DNA molecule, capable of replication in a host organism, into which a gene is inserted to construct a recombinant DNA molecule.

Phage Vector

This is a vector derived by modification of a phage genome, containing an origin of replication for a bacteriophage, but not one for a plasmid.

Phagemid Vector

This is a vector derived by modification of a plasmid genome, containing an origin of replication for a bacteriophage as well as the plasmid origin of replication.

Secreted

This describes a rgdp or molecule that associates with the member of a sbp displayed on the rgdp, in which the sbp member and/or the molecule, have been folded and the package assembled externally to the cellular cytosol.

Repertoire of Rearranged Immunoglobulin Genes

A collection of naturally occurring nucleotides eg DNA sequences which encoded expressed immunoglobulin genes in an animal. The sequences are generated by the in vivo rearrangement of e.g., V, D and J segments for H chains and e.g., the V and J segments for L chains. Alternatively the sequences may be generated from a cell line immunised in vitro and in which the rearrangement in response to immunisation occurs intracellularly. The word "repertoire" is used to indicate genetic diversity.

Library

A collection of nucleotide e.g., DNA, sequences within clones; or a genetically diverse collection of polypeptides, or specific binding pair members, or polypeptides or sbp members displayed on rgdps capable of selection or screening to provide an individual polypeptide or sbp members or a mixed population of polypeptides or sbp members.

Repertoire of Artificially Rearranged Immunoglobulin Genes

A collection of nucleotide e.g., DNA, sequences derived wholly or partly from a source other than the rearranged immunoglobulin sequences from an animal. This may include for example, DNA sequences encoding VH domains by combining unrearranged V segments with D and J segments and DNA sequences encoding VL domains by combining V and J segments.

Part or all of the DNA sequences may be derived by oligonucleotide synthesis.

Secretory Leader Peptide

This is a sequence of amino acids joined to the N-terminal end of a polypeptide and which directs movement of the polypeptide out of the cytosol.

Eluant

This is a solution used to breakdown the linkage between two molecules. The linkage can be a non-covalent or covalent bond(s). The two molecules can be members of a sbp.

Derivative

This is a substance which derived from a polypeptide which is encoded by the DNA within a selected rgdp. The derivative polypeptide may differ from the encoded polypeptide by the addition, deletion, substitution or insertion of amino acids, or by the linkage of other molecules to the encoded polypeptide. These changes may be made at the nucleotide or protein level. For example the encoded polypeptide may be a Fab fragment which is then linked to an Fc tail from another source. Alternatively markers such as enzymes, flouresceins etc. may be linked to eg Fab, scFv fragments.

According to one aspect of the invention, there is provided a method of producing multimeric specific binding pair (sbp) members, which method comprises expressing from a vector in recombinant host organism cells a population of a first polypeptide chain of a specific binding pair member fused to a component of a secreted replicable genetic display package (rgdp) which thereby displays said polypeptide chains at the surface of rgdps, and combining said population with a population of a second polypeptide chain of said specific binding pair member by causing or allowing first and second polypeptide chains to come together to form a library of said multimeric specific binding pair members displayed by rgdps, said population of second polypeptide chains not being expressed from the same vector as said population of first polypeptide chains, at least one of said populations being genetically diverse and expressed from nucleic acid that is capable of being packaged using said rgdp component, whereby the genetic material of each said rgdp encodes a polypeptide chain of a said genetically diverse population.

The first and second polypeptide chains may be expressed in the same host organism cell, or not expressed in the same host organism cells. In the latter case the population of second polypeptide chains may comprise a repertoire of polypeptides purified from a human or animal source.

In a prefered method each said polypeptide chain is expressed from nucleic acid which is capable of being packaged as a rgdp using said component fusion product.

The method may comprise introducing vectors capable of expressing a population of said first polypeptide chains into host organisms which express a population of said second polypeptide chains in free form, or introducing vectors capable of expressing a population of said second polypeptide chains in free form into host organisms which express a population of said first polypeptide chains.

On the other hand each said second polypeptide chains may be each expressed as a fusion with a component of a rgdp which thereby displays said second polypeptide chains at the surface of rgdps. In other words, both first and second chains may be displayed on rgdps by fusion to, for example, a capsid problem. In a method where soluble chains are combined with fusions of polypeptide chains and rgdp component the following steps may be included:

(a) forming an extracellular mixture of a population of soluble second polypeptide chains and rgdps displaying a population of first polypeptide chains; and (b) causing or allowing first and second polypeptide chains to come together to form the library of said multimeric specific binding pair members.

The extracellular mixture may be partially denatured before being renatured to cause or allow said first and second polypeptide chains to come together to form said library. The population of second polypeptide chains may comprise a repertoire of polypeptides purified from a human or animal source.

The populations of said polypeptide chains may be derived from:

(i) the repertoire of rearranged immunoglobulin genes of an animal immunised with complementary sbp member;

(ii) the repertoire of rearranged immunoglobulin genes of an animal not immunised with complementary sbp member;

(iii) a repertoire of an artificially rearranged immunoglobulin gene or genes;

(iv) a repertoire of an immunoglobulin homolog gene or genes; or (v) a repertoire of sequences derived from a germ-line immunoglobulin gene or genes;

(vi) a repertoire of an immunoglobulin gene or genes artificially mutated by the introduction of one or more point mutations.

(vii) a mixture of any of (i), (ii), (iii), (iv), (v) and (vi).

When a phage is used as rgdp it may be selected from the class I phages fd, M13, f1, If1, lke, ZJ/Z, Ff and the class II phages Xf, Pf1 and Pf3.

Following combination, rgdps may be selected or screened to provide an individual sbp member or a mixed population of said sbp members associated in their respective rgdps with nucleic acid encoding a polypeptide chain thereof. The restricted population of at least one type of polypeptide chain provided in this way may then be used in a further dual combinatorial method in selection of an individual, or a restricted population of complementary chain.

Nucleic acid taken from a restricted rgdp population encoding said first polypeptide chains may be introduced into a recombinant vector into which nucleic acid from a genetically diverse repertoire of nucleic acid encoding said second polypeptide chains is also introduced, or the nucleic acid taken from a restricted rgdp population encoding said second polypeptide chains may be introduced into a recombinant vector into which nucleic acid from a genetically diverse repertoire of nucleic acid encoding said first polypeptide chains is also introduced.

The recombinant vector may be produced by intracellular recombination between two vectors and this may be promoted by inclusion in the vectors of sequences at which site-specific recombination will occur, such as loxP sequences obtainable from coliphage P1. Site-specific recombination may then be catalysed by Cre-recombinase, also obtainable from coliphage P1.

The Cre-recombinase used may be expressible under the control of a regulatable promoter.

Production of a recombinant vector may be used to produce nucleic acid encoding a single chain Fv region derivative of an immunoglobulin resulting from recombination between first and second vectors.

It may be desirable for the vector comprising nucleic acid encoding the first polypeptide chain to be a phage or phagemid while the vector comprising nucleic acid encoding the second polypeptide chain being a plasmid; or the vector comprising nucleic acid encoding the first polypeptide chain to be a plasmid while the vector comprising nucleic acid encoding the second polypeptide chain is a phage or phagemid. Then, the intracellular recombination may take place in a bacterial host which replicates plasmids preferentially over phages or phagemids, or which replicates phages or phagemids preferentially over plasmids. It may be advantageous to use a system wherein the preferential replication of one type of vector over the other is conditional.

This is discussed later with reference to PolA strain of *E. coli* or of another grain-negative bacterium.

The invention envisages also a method of producing multimeric specific binding pair (sbp) members, which method comprises (i) causing or allowing intracellular recombination between (a) first vectors comprising nucleic acid encoding a population of a fusion of a first polypeptide chain of a specific binding pair member and a component of a secreted replicable genetic display package (rgdp) and (b) second vectors comprising nucleic acid encoding a population of a second polypeptide chain of a specific binding pair member, at least one of said populations being genetically diverse, the recombination resulting in recombinant vectors each of which comprises nucleic acid encoding a said polypeptide fusion and a said second polypeptide chain and capable of being packaged using said rgdp component; and (ii) expressing said polypeptide fusions and said second polypeptide chains, producing rgdps which display at their surface said first and second polypeptide chains and which each comprise nucleic acid encoding a said first polypeptide chain and a said second polypeptide chain.

This may be with or without a preliminary selection or restriction of one of the populations of second polypeptide chains by any other method according to the invention.

An important aspect of the present invention provides a method of producing one or a selected population of multichain polypeptide members of a specific binding pair (sbp members) specific for a counterpart specific binding pair member of interest, which method comprises the following steps:

(i) expressing from a vector in recombinant host organism cells a genetically diverse population of a first polypeptide chain of said multichain protein, fused to a component of a replicable genetic display package (rgdp) which thereby displays said polypeptide chains at the surface of rgdps;

(ii) combining said population with a unique or restricted population of second polypeptide chains of said multichain sbp members, not being expressed from the same vector as said population of first polypeptide chains, said combining forming a library of said multichain sbp members displayed by rgdps, said genetically diverse population being expressed from nucleic acid which is capable of being packaged using said rgdp component, whereby the genetic material of each said rgdp encodes a said first polypeptide chain;

(iii) selecting by affinity with said counterpart sbp member of interest multichain sbp members specific for said counterpart sbp member associated in their respective rgdps with nucleic acid encoding a said first polypeptide chain thereof;

(iv) combining said first polypeptide chains of multichain sbp members selected in step (iii) with a genetically diverse population of second polypeptide chains of multichain sbp members, the said second polypeptide chains being fused to a component of a rgdp which thereby displays them at the surface of rgdps, the said combining in this step (iv) forming a library of multichain sbp members from which one or more multichain sbp members specific for said counterpart sbp member are selectable by affinity with it.

These multichain sbp members may be antibodies, or other members of the immunoglobulin family, or binding fragments thereof, or any other multimeric sbp member. See elsewhere in this text for other examples.

Advantages and benefits of such a method are discussed elsewhere in this application. This technique may be modified for "humanising" antibodies, optionally in combination with CDR grafting and perhaps with the use of chimaeric polypeptide chains. Useful chimaerics may comprise a variable domain derived from a non-human animal antibody specific for the antigen of interest and a human antibody domain, such as one comprising Cy1. A genetically diverse population of chimaeric second polypeptide chains may be used in step (ii) of the method. Each of said population of second polypeptide chains combined in step (iv) may be a human chain which comprises an imposed complementarity determining region (CDR) from a non-human animal antibody specific for said antigen. If said first polypeptide chains are immunoglobulin light chains and said second polypeptide chains are immunoglobulin heavy chains. Then it may be beneficial in a selection of a high specificity humanised antibody for the imposed CDR to be CDR3.

The invention encompasses kits for use in carrying out a method according to any aspect of the invention. A kit may have the following components in additional to ancillary components required for carrying out the method:

(i) a vector having the following features: (a) an origin of replication for single-stranded bacteriophage, (b) a restriction site for insertion of nucleic acid encoding or a polypeptide component of an sbp member, (c) said restriction site being in the 5' end region of the mature coding sequence of a phage capsid protein, and (d) with a secretory leader sequence upstream of said site which directs a fusion of the capsid protein and sbp polypeptide to the periplasmic space of a bacterial host; and (ii) another vector, having some or all of the features (a), (b), (c) and (d) of the vector described in (i).

Another kit for use in carrying out a method according to one aspect of the invention may have the following components in addition to ancillary components required for carrying out the method:

(i) a first vector having the following features:
(a) a restriction site for insertion of nucleic acid encoding or a polypeptide component of an sbp member, (b) said restriction site being in the 5' end region of the mature coding sequence of a phage capsid protein, and (c) with a secretory leader sequence upstream of said site which directs a fusion of the capsid protein and sbp polypeptide to the periplasmic space of a bacterial host; and
(ii) a second vector having a restriction site for insertion of nucleic acid encoding a second said polypeptide chain,
(iii) at least one of the vectors having an origin of replication for single-stranded bacteriophage, and
(iv) the vectors having sequences at which site-specific recombination will occur.

In the above methods, the binding molecule may be an antibody, or a domain that is homologous to an immunoglobulin. The antibody or domain may be either naturally derived or synthetic or a combination of both. The domain may be a Fab, scFv, Fv dAb or Fd molecule. Alternatively, the binding molecule may be an enzyme or receptor or fragment, derivative or analogue of any such enzyme or receptor. Alternatively, the binding molecule may be a member of an immunoglobulin superfamily and which has a structural form based on an immunoglobulin molecule.

The present invention also provides rgdps as defined above and members of specific binding pairs e.g., binding molecules such as antibodies, enzymes, receptors, fragments and derivatives thereof, obtainable by use of any of the above defined methods. The derivatives may comprise members of the specific binding pairs fused to another molecule such as an enzyme or a Fc tail.

The invention also includes kits for carrying out the methods hereof. The kits will include the necessary vectors. One such vector will typically have an origin of replication for single stranded bacteriophage and either contain the sbp member nucleic acid or have a restriction site for its insertion in the 5' end region of the mature coding sequence of a phage capsid protein, and with a secretory leader coding sequence upstream of said site which directs a fusion of the capsid protein exogenous polypeptide to the periplasmic space.

The restriction sites in the vectors are preferably those of enzymes which cut only rarely in protein coding sequences.

The kit preferably includes a phagemid vector which may have the above characteristics, or may contain, or have a site for insertion, of sbp member nucleic acid for expression of the encoded polypeptide in free form.

The kits will also contain ancillary components required for carrying out the method, the nature of such components depending of course on the particular method employed.

Useful ancillary components may comprise helper phage, PCR primers, and buffers and enzymes of various kinds.

PCR primers and associated reagents for use where the sbp members are antibodies may have the following characteristics:
(i) primers having homology to the 5' end of the sense or anti-sense strand of sequences encoding domains of antibodies; and
(ii) primers including tag sequences 5' to these homologous sequences which incorporate restriction sites to allow insertion into vectors; together with sequences to allow assembly of amplified VH and VL regions to enable expression as Fv, scFv or Fab fragments.

Also comprehended by the present invention is the provision of an intermediate product of a dual combinatorial method, comprising a selected or partially selected mixed population of vectors or specific binding pair members, such as antibodies, which can then be used in a further method of combination and selection.

Buffers and enzymes are typically used to enable preparation of nucleotide sequences encoding Fv, scFv or Fab fragments derived from rearranged or unrearranged immunoglobulin genes according to the strategies described herein.

The applicants have chosen the filamentous F-specific bacteriophages as an example of the type of phage which could provide a vehicle for the display of binding molecules e.g. antibodies and antibody fragments and derivatives thereof, on their surface and facilitate subsequent selection and manipulation.

The F-specific phages (e.g. fl, fd and M13) have evolved a method of propagation which does not kill the host cell and they are used commonly as vehicles for recombinant DNA (Kornberg, A., DNA Replication, W. H. Freeman and Co., San Francisco, 1980). The single stranded DNA genome (approximately 6.4 Kb) of fd is extruded through the bacterial membrane where it sequesters capsid sub-units, to produce mature virions. These virions are 6 nm in diameter, 1 μm in length and each contain approximately 2,800 molecules of the major coat protein encoded by viral gene VIII and four molecules of the adsorption molecule gene III protein (g3p) the latter is located at one end of the virion. The structure has been reviewed by Webster et al., 1978 in The Single Stranded DNA Phages, 557–569, Cold Spring Harbor Laboratory Press. The gene III product is involved in the binding of the phage to the bacterial F-pilus.

Although these phages do not kill their host during normal replication, disruption of some of their genes can lead to cell death (Kornberg, A., 1980 supra.) This places some restraint on their use. The applicants have recognized that gene III of phage fd is an attractive possibility for the insertion of biologically active foreign sequences. There are however, other candidate sites including for example gene VIII and gene VI.

The protein itself is only a minor component of the phage coat and disruption of the gene does not lead to cell death (Smith, G. 1988, Virology 167: 156–165). Furthermore, it is possible to insert some foreign sequences (with no biological function) into various positions within this gene (Smith, G. 1985 Science 228: 1315–1317., Parmley, S. F. and Smith, G. P. Gene: 73 (1988) p. 305–318., and de la Cruz, V. F., et al., 1988, J. Biol. Chem., 263: 4318–4322). Smith et al described the display of peptides on the outer surface of phage but they did not describe the display of protein domains. Peptides can adopt a range of structures which can be different when in free solution, than when bound to, for example, an antibody, or when forming part of a protein (Stanfield, R. I. et al., (1990) Science 248, p712–719). Proteins in general have a well defined tertiary structure and perform their biological function only when adopting this structure. For example, the structure of the antibody D1.3 has been solved in the free form and when bound to antigen (Bhat, T. N. et al., (1990) Nature 347, p483–485). The gross structure of the protein is identical in each instance with only minor variations around the binding site for the antigen. Other proteins have more substantial conformation changes on binding of ligand, for instance the enzymes hexokinase and pyruvate dehydrogenase during their catalytic cycle, but they still retain their overall pattern of folding. This structural integrity is not confined to whole proteins, but is exhibited by protein domains. This leads to the concept of a folded unit which is part of a protein, often a domain, which has a well defined primary, secondary and tertiary structure and which retains the same overall folding pattern whether binding to a binding partner or not. The only gene sequence that Smith et al., described that was of sufficient size to encode a domain (a minimum of perhaps 50 amino acids) was a 335 bp fragment of a β-galactosidase corresponding to nucleotides 861–1195 in the β-galactosidase gene sequence (Parmley, S.+Smith, G. P. 1988 supra. This would encode 112 amino acids of a much larger 380 amino acid domain. Therefore, prior to the present application, no substantially complete domain or folded unit had been displayed on phage. In these cases, although the infectivity of the virion was disrupted, the inserted sequences could be detected on the phage surface by use of e.g. antibodies.

The protein encoded by gene III has several domains (Pratt, D., et al., 1969 Virology 39:42–53., Grant, R. A., et al., 1981, J. Biol. Chem. 256: 539–546 and Armstrong, J., et al., FEBS Lett. 135: 167–172 1981.) including: (i) a signal sequence that directs the protein to the cell membrane and which is then cleaved off; (ii) a domain that anchors the mature protein into the bacterial cell membrane (and also the phage coat); and (iii) a domain that specifically binds to the phage receptor, the F-pilus of the host bacterium. Short sequences derived from protein molecules have been inserted into two places within the mature molecule (Smith, G., 1985 supra., and Parmley, S. F. and Smith G.P., 1988 supra.). Namely, into an inter-domain region and also between amino acids 2 and 3 at the N-terminus. The insertion sites at the N-terminus were more successful in maintaining the structural integrity of the gene III protein and displaying the peptides on the surface of the phage. By use of antisera specific for the peptides, the peptides inserted into this position were shown to be on the surface of the phage. These authors were also able to purify the phage, using this property. However, the peptides expressed by the phage, did not possess measurable biological functions of their own.

Retaining the biological function of a molecule when it is expressed in a radically different context to its natural state is difficult. The demands on the structure of the molecule are heavy. In contrast, retaining the ability to be bound by specific antisera is a passive process which imposes far less rigorous demands on the structure of the molecule. For example, it is the rule rather than the exception that polyclonal antisera will recognise totally denatured, and biologically inactive, proteins on Western blots (see for example, Harlow, E. and Lane, D., Antibodies, a Laboratory Manual, Cold Spring Harbor Laboratory Press 1988). Therefore, the insertion of peptides into a region that allows their structure to be probed with antisera teaches only that the region allows the inserted sequences to be exposed and does not teach that the region is suitable for the insertion of large sequences with demanding structural constraints for the display of a molecule with a biological or binding function. In particular, it does not teach that domains or folded units of proteins can be displayed from sequences inserted in this region.

This experience with Western blots is a graphic practical demonstration which shows that retaining the ability to be bound by specific antisera imposes far less rigorous demands on the structure of a polypeptide, than does folding for the retention of a biological function.

Studies have been carried out, in which E. coli have been manipulated to express the protein β-adrenergic receptor as a fusion with the outer membrane protein lamB. The β-adrenergic receptor was expressed in a functional form as determined by the presence of binding activity. However, when an equivalent antibody fusion was made with lamB, the antibody fusion was toxic to the host cell.

The applicants have investigated the possibility of inserting the gene coding sequence for biologically active antibody fragments into the gene III region of fd to express a large fusion protein. As is apparent from the previous discussion, this approach makes onerous demands on the functionality of the fusion protein. The insertion is large, encoding antibody fragments of at least 100–200 amino acids; the antibody derived domain must fold efficiently and correctly to display antigen-binding; and most of the functions of gene III must be retained. The applicants approach to the construction of the fusion molecule was designed to minimise the risk of disrupting these functions. In an embodiment of the invention, the initial vector used was fd-tet (Zacher, A. N., et al., 1980, Gene 9, 127–140) a tetracycline resistant version of fd bacteriophage that can be propagated as a plasmid that confers tetracycline resistance to the infected E. coli host. The applicants chose to insert after the signal sequence of the fd gene III protein for several reasons. In particular, the applicants chose to insert after amino acid 1 of the mature protein to retain the context for the signal peptidase cleavage. To retain the structure and function of gene III itself, the majority of the original amino acids are synthesized after the inserted immunoglobulin sequences. The inserted immunoglobulin sequences were designed to include residues from the switch region that links VH-VL to CH1-CL (Lesk, A., and Chothia, C., Nature 335, 188–190, 1988).

Surprisingly, by manipulating gene III of bacteriophage fd, the present applicants have been able to construct a bacteriophage that displays on its surface large biologically functional antibody, enzyme, and receptor molecules whilst remaining intact and infectious. Furthermore, the phages bearing antibodies of desired specificity, can be selected from a background of phages not showing this specificity.

The sequences coding for a population of antibody molecules and for insertion into the vector to give expression of antibody binding functions on the phage surface can be derived from a variety of sources. For example, immunised or non-immunised rodents or humans, and from organs such as spleen and peripheral blood lymphocytes. The coding sequences are derived from these sources by techniques familiar to those skilled in the art (Orlandi, R., et al., 1989 supra; Larrick, J. W., et al., 1989 supra; Chiang, Y. L., et al., 1989 Bio Techniques 7, p. 360–366; Ward, E. S, et al., 1989 supra; Sastry, L., et al., 1989 supra.)

The disclosure made by the present applicants is important and provides a significant breakthrough in the technology relating to the production of biological binding molecules, their fragments and derivatives by the use of recombinant methods.

In standard recombinant techniques for the production of antibodies, an expression vector containing sequences coding for the antibody polypeptide chains is used to transform e.g. E. coli. The antibody polypeptides are expressed and detected by use of standard screening systems. When the screen detects an antibody polypeptide of the desired specificity, one has to return to the particular transformed E. coli expressing the desired antibody polypeptide. Furthermore, the vector containing the coding sequence for the desired antibody polypeptide then has to be isolated for use from E. coli in further processing steps.

In the present invention however, the desired antibody polypeptide when expressed, is already packaged with its gene coding sequence. This means that when the an antibody polypeptide of desired specificity is selected, there is no need to return to the original culture for isolation of that sequence. Furthermore, in previous methods in standard recombinant techniques, each clone expressing antibody needs to be screened individually. The present application provides for the selection of clones expressing antibodies with desired properties and thus only requires screening of clones from an enriched pool.

Because a rgdp (e.g., a pAb) displays a member of a specific binding pair (e.g., an antibody of monoclonal antigen-binding specificity) at the surface of a relatively simple replicable structure also containing the genetic information encoding the member, rgdps e.g., pAbs, that bind to the complementary member of the specific binding pair (e.g., antigen) can be recovered very efficiently by either eluting off the complementary member using for example diethylamine, high salt etc. and infecting suitable bacteria, or by denaturing the structure, and specifically amplifying the sequences encoding the member using PCR. That is, there is no necessity to refer back to the original bacterial clone that gave rise to the pAb.

For some purposes, for example immunoprecipitation and some diagnostic tests, it is advantageous to use polyclonal antibodies or antibody fragments. The present invention allows this to be achieved by either selection of an enriched pool of pAbs with desired properties or by mixing individually isolated clones with desired properties. The antibodies or antibody fragments may then be expressed in soluble form if desired. Such a selected polyclonal pAb population can be grown from stocks of phage, bacteria containing phagemids or bacteria expressing soluble fragments derived from the selected polyclonal population. Thus a reagent equivalent to a polyclonal antiserum is created which can be replicated and routinely manufactured in culture without use of animals.

SELECTION FORMATS AND AFFINITY MATURATION

Individual rgdps e.g., pAbs expressing the desired specificity e.g., for an antigen, can be isolated from the complex library using the conventional screening techniques (e.g. as described in Harlow, E., and Lane, D., 1988, supra Gherardi, E et al. 1990. J. Immunol. Meth. 126 p61–68).

The applicants have also devised a series of novel selection techniques that are practicable only because of the unique properties of rgdps. The general outline of some screening procedures is illustrated in FIG. 15 using pAbs as an example type of rgdp.

The population/library of pAbs to be screened could be generated from immunised or other animals; or be created in vitro by mutagenising pre-existing phage antibodies (using techniques well-known in the art such as oligonucleotide directed mutagenesis (Sambrook, J., et al., 1989 Molecular Cloning a Laboratory Manual, Cold Spring Harbor Laboratory Press). This population can be screened in one or more of the formats described below with reference to FIG. 15, to derive those individual pAbs whose antigen binding properties are different from sample c.

Binding Elution

FIG. 15(i) shows antigen (ag) bound to a solid surface (s) the solid surface (s) may be provided by a petri dish, chromatography beads, magnetic beads and the like. The population/library of pAbs is then passed over the ag, and those individuals p that bind are retained after washing, and optionally detected with detection system d. A detection system based upon anti-fd antisera is illustrated in more detail in example 4 of WO 92/01047. If samples of bound population p are removed under increasingly stringent conditions, the binding affinity represented in each sample will increase. Conditions of increased stringency can be obtained, for example, by increasing the time of soaking or changing the pH of the soak solution, etc.

Competition

Referring to FIG. 15(ii) antigen ag can be bound to a solid support s and bound to saturation by the original binding molecule c. If a population of mutant pAb (or a set of unrelated pAbs) is offered to the complex, only those that have higher affinity for antigen ag than c will bind. In most examples, only a minority of population c will be displaced by individuals from population p. If c is a traditional antibody molecule, all bound material can be recovered and bound p recovered by infecting suitable bacteria and/or by use of standard techniques such as PCR.

An advantageous application is where ag is used as a receptor and c the corresponding ligand. The recovered bound population p is then related structurally to the receptor binding site/and or ligand. This type of specificity is known to be very useful in the pharmaceutical industry.

Another advantageous application is where ag is an antibody and c its antigen. The recovered bound population p is then an anti-idiotype antibody which have numerous uses in research and the diagnostic and pharmaceutical industries.

At present it is difficult to select directly for anti-idiotype antibodies. pAbs would give the ability to do this directly by binding pAb libraries (e.g., a naive library) to B cells (which express antibodies on their surface) and isolating those phage that bound well.

In some instances it may prove advantageous to pre-select population p. For example, in the anti-idiotype example above, p can be absorbed against a related antibody that does not bind the antigen.

However, if c is a pAb, then either or both c and p can advantageously be marked in some way to both distinguish and select for bound p over bound c. This marking can be physical, for example, by pre-labelling p with biotin; or more advantageously, genetic. For example, c can be marked with an EcoB restriction site, whilst p can be marked with an EcoK restriction site (see Carter, P. et al., 1985, Nucl. Acids Res. 13, 4431–4443). When bound p+c are eluted from the antigen and used to infect suitable bacteria, there is restriction (and thus no growth) of population c (i.e. EcoB restricting bacteria in this example). Any phage that grew, would be greatly enriched for those individuals from p with higher binding affinities. Alternatively, the genetic marking can be achieved by marking p with new sequences, which can be used to specifically amplify p from the mixture using PCR.

Since the bound pAbs can be amplified using for example PCR or bacterial infection, it is also possible to rescue the desired specificity even when insufficient individuals are bound to allow detection via conventional techniques.

The preferred method for selection of a phage displaying a protein molecule with a desired specificity or affinity will often be elution from an affinity matrix with a ligand (eg example 21 of WO 92/01047). Elution with increasing concentrations of ligand should elute phage displaying binding molecules of increasing affinity. However, when e.g., a pAb binds to its antigen with high affinity or avidity (or another protein to its binding partner) it may not be possible to elute the pAb from an affinity matrix with molecule related to the antigen. Alternatively, there may be no suitable specific eluting molecule that can be prepared in sufficiently high concentration. In these cases it is necessary to use an elution method which is not specific to eg the antigen-antibody complex. Some of the non-specific elution methods generally used reduce phage viability for instance, phage viability is reduced with time at pH12 (Rossomando, E. F. and Zinder N. D. J. Mol.Biol. 36 387–399 1968). There may be interactions between e.g., antibodies and affinity matrices which cannot be disrupted without completely removing phage infectivity. In these cases a method is required to elute phage which does not rely on disruption of eg the antibody-antigen interaction. A method was therefore devised which allows elution of bound pAbs under mild conditions (reduction of a dithiol group with dithiothreitol) which do not disrupt phage structure (example 47 of WO 92/01047).

This elution procedure is just one example of an elution procedure under mild conditions. A particularly advantageous method would be to introduce a nucleotide sequence encoding amino acids constituting a recognition site for cleavage by a highly specific protease between the foreign gene inserted, in this instance a gene for an antibody fragment, and the sequence of the remainder of gene III. Examples of such highly specific proteases are Factor X and thrombin. After binding of the phage to an affinity matrix and elution to remove non-specific binding phage and weak binding phage, the strongly bound phage would be removed by washing the column with protease under conditions suitable for digestion at the cleavage site. This would cleave the antibody fragment from the phage particle eluting the phage. These phage would be expected to be infective, since the only protease site should be the one specifically introduced. Strongly binding phage could then be recovered by infecting e.g., E. coli TG1 cells.

An alternative procedure to the above is to take the affinity matrix which has retained the strongly bound pAb and extract the DNA, for example by boiling in SDS solution. Extracted DNA can then be used to directly transform E. coli host cells or alternatively the antibody encoding sequences can be amplified, for example using PCR with suitable primers such as those disclosed herein, and then inserted into a vector for expression as a soluble antibody for further study or a pAb for further rounds of selection.

Another preferred method for selection according to affinity would be by binding to an affinity matrix containing low amounts of ligand.

If one wishes to select from a population of phages displaying a protein molecule with a high affinity for its ligand, a preferred strategy is to bind a population of phage to an affinity matrix which contains a low amount of ligand. There is competition between phage, displaying high affinity and low affinity proteins, for binding to the ligand on the matrix. Phage displaying high affinity protein is preferentially bound and low affinity protein is washed away. The high affinity protein is then recovered by elution with the ligand or by other procedures which elute the phage from the affinity matrix (example 35 of WO 92/01047 demonstrates this procedure).

In summary then, for recovery of the packaged DNA from the affinity step, the package can be simply eluted, it can be eluted in the presence of a homologous sbp member which competes with said package for binding to a complementary sbp member; it could be removed by boiling, it could be removed by proteolytic cleavage of the protein; and other methods will be apparent to those skilled in the art e.g., destroying the link between the substrate and complementary sbp member to release said packaged DNA and sbp member. At any rate, the objective is to obtain the DNA from the package so that it can be used directly or indirectly, to express the sbp member encoded thereby.

The efficiency of this selection procedure for pAbs and the ability to create very large libraries means that the immunisation techniques developed to increase the proportion of screened cells producing antibodies of interest will not be an absolute requirement. The technique allows the rapid isolation of binding specificities e.g., antigen-binding specificities, including those that would be difficult or even unobtainable by conventional techniques, for example, catalytic or anti-idiotypic antibodies. Removal of the animal altogether is now possible, once a complete library of the immune repertoire has been constructed. The structure of the pAb molecule can be used in a number of other applications, some examples of which are:

Signal Amplification

Acting as a molecular entity in itself, rgdps e.g., pAbs combine the ability to bind a specific molecule e.g., antigen with amplification, if the major coat protein is used to attach another moiety. This moiety can be attached via immunological, chemical, or any other means and can be used, for example, to label the complex with detection reagents or cytotoxic molecules for use in vivo or in vitro.

Physical Detection

The size of the rgdps e.g., pAbs can be used as a marker particularly with respect to physical methods of detection such as electron microscopy and/or some biosensors, e.g. surface plasmon resonance.

Diagnostic Assays

The rgdps e.g., pAbs also have advantageous uses in diagnostic assays, particularly where separation can be effected using their physical properties for example centrifugation, filtration etc.

In order that the invention is more fully understood, embodiments will be described in more detail by way of example only and not by way of limitation with reference to the figures described below.

BRIEF DESCRIPTION OF THE FIGURES

FIG. 4 shows various possible combinations of heavy and light chains, gene 3 fusions, and replicons in polycombinantorial libraries.

FIGS. 7(i)–7(ii) show the sequence of the template clone used in example 1. This is Aab NQ10.12.5 (Hoogenboom et al 1991, supra).

FIG. 8 illustrates a strategy for cloning heavy and light chains as separate elements.

FIG. 9 shows the sequence of polylinker used in pUC19 and pUC119 derivatives in example 1.

FIG. 10 shows the results of the infection experiments described in example 1, illustrating interference between phage and phagemid vectors.

FIG. 12 shows ELISA results which show that only when the correct heavy and light chain combination is used is a functional antibody produced, as demonstrated in example 3.

FIGS. 13(i)–13(ii) show an example of a scheme for humanising a mouse monoclonal antibody.

FIGS. 15(i)–15(ii) show schematically selection techniques which utilise the unique properties of pAbs; 15(i) shows a binding/elution system; and 15(ii) shows a competition system (p=pAb; ag=antigen to which binding by pAb is required; c=competitor population e.g. antibody, pAb, ligands; s=substrate (e.g. plastic beads etc); d=detection system.

FIG. 16 shows the sequence around the cloning site in gene III of fd DOG1. Restriction enzyme sites are shown as well as the amino acids encoded by antibody derived sequences. These are flanked at the 5' end by the gene III signal peptide and at the 3' end by 3 alanine residues (encoded by the Not 1 restriction site) and the remainder of the mature gene III protein. The arrow shows the cleavage site for cutting of the signal peptide.

FIG. 19. There ways of displaying antibody fragments on the surface of phage by fusion to gene III protein.

Figure 1:
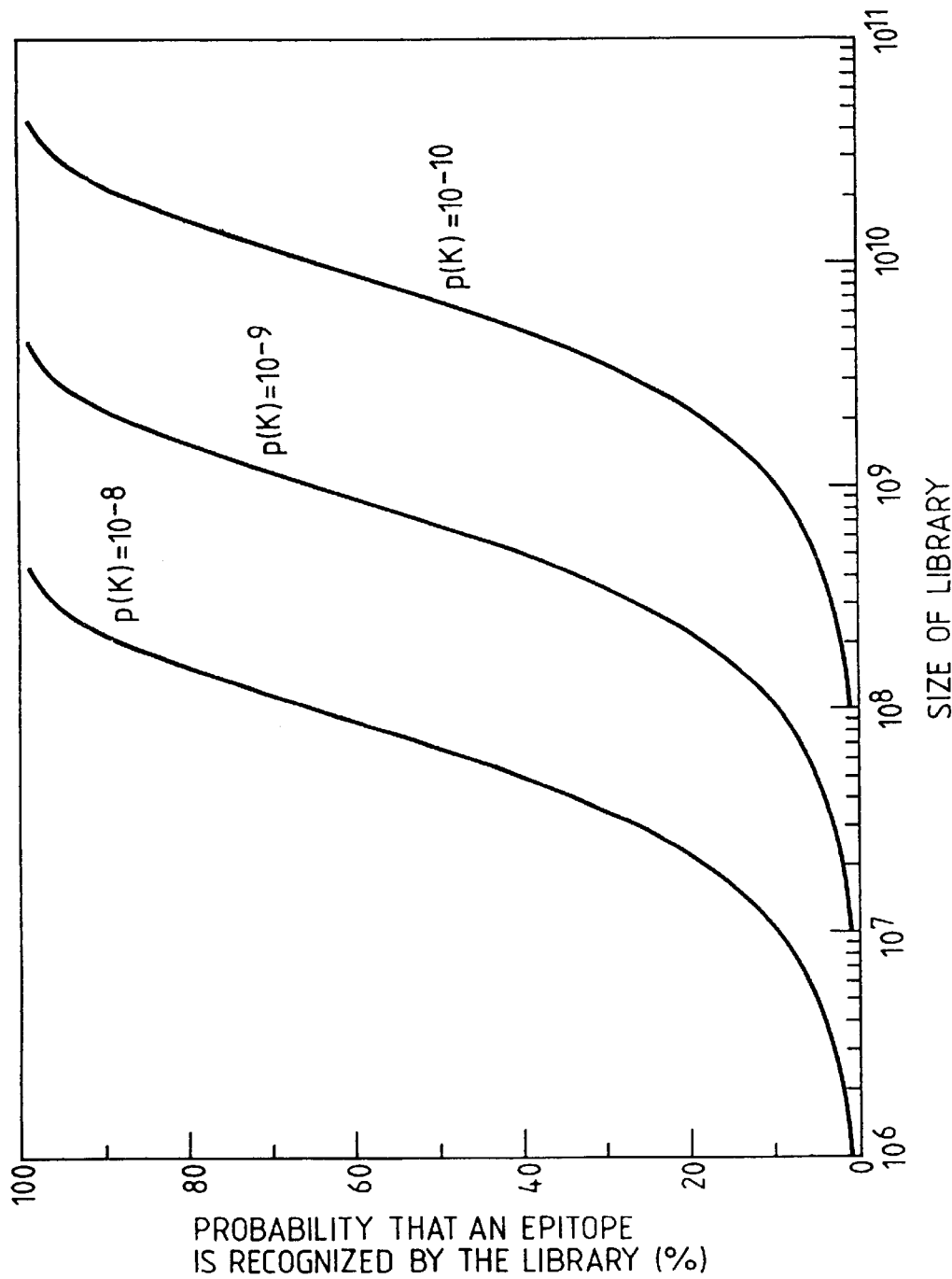
FIG. 1 shows plots of the probability of isolating an antibody with a given p[K] value against the size of a library.

Disclosed here are methods for preparing extremely diverse libraries of antibody heavy and light chains. Heavy and light chains are cloned on separate replicons and functional antibody produced by post-translational assembly of heavy and light chains in vivo or in vitro, such that the final number of combinations created is the number of heavy chains multiplied by the number of light chains. Such a format is also convenient for chain-shuffling, mutagenesis, humanising and CDR 'imprinting'. These methods can also be applied to other proteins in which two or more different subunits assemble to create a functional oligomer.

The first functional antibody molecules to be expressed on the surface of filamentous phage were single-chain Fv's (scFv), so-called because heavy and light chain variable domains, normally on two separate proteins, are covalently joined by a flexible linker peptide. Alternative expression strategies have also been successful. Monomeric Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains assemble post-translationally and the dimer is incorporated into the phage particle via linkage of one of the chains to g3p.

More recent cloning experiments have been performed with 'phagemid' vectors which have ca. 100-fold higher transformation efficiencies than phage DNA. These are plasmids containing the intergenic region from filamentous phages which enables single-stranded copies of the phagemid DNA to be produced, and packaged into infectious filamentous particles when cells harbouring them are infected with 'helper' phages providing the phage components in trans. When phagemids contain gIII fused to an antibody gene (e.g. pHEN-1), the resulting fusion protein is displayed on the phagemid particle (Hoogenboom, H. R., A. D. Griffiths, K. S. Johnson, D. J. Chiswell, P. Hudson and G. Winter. (1991). Multi-subunit proteins on the surface of filamentous phage: methodologies for displaying antibody (Fab) heavy and light chains. *Nucleic Acids Res.* 19 (15), 4133–4137). Considerable progress has been made in developing efficient strategies for cloning antibody genes, a factor which becomes most important when dealing with large numbers of different antibody fragments such as repertoires.

The cloning vector fd-DOG-1 was used in early work with phage antibody repertoires in which scFv fragments were derived from spleen mRNA of mice immunised with the hapten oxazalone (Clackson, T., H. R. Hoogenboom, A. D. Griffiths and G. Winter. (1991). Making antibody fragments using phage display libraries. *Nature* 352, 624–628); VH and VL domains were separately amplified then linked at random via a short DNA fragment encoding the scFv linker peptide to produce a library of approximately $10^5$ different clones. This was panned against the immunising antigen to select combinations of VH and VL which produced functional antibodies. Several binders were isolated, one in particular having an affinity not far below that of the best monoclonal anitbodies produced by conventional hybridoma technology.

In a mouse, at any one time there are approximately $10^7$ possible H chains and $10^5$ possible L chains, making a total of $10^{12}$ possible VH:VL combinations when the two chains are combined at random (these figures are estimates and simply provide a rough guide to repertoire size). By these figures, tha above mouse library sampled only 1 in $10^7$ of the possible VH:VL combinations. It is likely that good affinity antibodies were isolated because the spleen cells derived from an immunised donor, in which B cells capable of recognising the antigen are clonally expanded and producing large quantities of Ig mRNA. The low library complexity in this experiment is partly due to the intrinsically low transformation efficiency of phage DNA compared to plasmid (or phagemid).

Marks et al. (Marks, J. D. Hoogenboom, H. R., Bonnert, T. P., McCafferty, J., Griffiths, A. D. and Winter, G. (1991) By-passing immunization: Human antibodies from V-gene libraries displayed on phage. J.Mol.Biol. 222, 581–597) and PCT/GB91/01134 describe construction of an antibody repertoire from unimmunised humans cloned in the phagemid pHEN-1. This library, consisting of $3.10^7$ clones has so far yielded specific antibodies to ten different antigens. These antibodies have the moderate affinities expected of a primary immune response, demonstrating that usable antibodies to a range of structurally diverse antigens can indeed be isolated from a single resource.

New binders can be created from clones isolated from phage antibody libraries using a procedure calls 'chain-shuffling'. In this process one of the two chains is fixed and the other varied. For example, by fixing the heavy chain from the highest affinity mouse anti-OX phage antibody and recloning the repertoire of light chains alongside it, libraries of $4.10^7$ were constructed. Several new OX-binders were isolated, and the majority of these had light chains that were distinct from those first isolated and considerably more diverse. These observations reflect the fact that a small library is sufficient to tap the available diversity when only one chain is varied, a useful procedure if the original library was not sufficiently large to contain the available diversity.

The size of the library is of critical importance. This is especially true when attempting to isolate antibodies from a naive human repertoire, but is equally relevant to isolation of the highest affinity antibodies from an immunised source.

It is clear that while phage display is an exceptionally powerful tool for cloning and selecting antibody genes, we are tapping only the tiniest fraction of the potential diversity using existing technology. Transformation efficiencies place the greatest limitation on library size with $10^9$ being about the limit using current methods. Rough calculations suggest that this is several orders of magnitude below the target efficiency; more rigourous analysis confirms it.

Perelson and Oster have given theoretical consideration to the relationship between size of the immune repertoire and the likelihood of generating an antibody capable of recognising a given epitope with greater than a certain threshold affinity, K. The relationship is described by the equation:

$$P = e^{-N(p[K])}$$

where P=probability that an epitope is not recognised with an affinity above the threshold value K by any antibody in the repertoire.

N=number of different antibodies in the repertoire.

and p[K]=probability that an individual antibody recognises a random epitope with an affinity above the threshold value K.

In this analysis p[K] is inversely proportional to affinity, although an algorithm describing this relationship precisely has not been deduced. Despite this, it is apparent that the higher the affinity of the antibody, the lower its p[K] and the larger the repertoire needs to be to achieve a reasonable probability of isolating the antibody. The other important feature is that the function is exponential; as shown in FIG. 1, a small change in library size can have either a negligible or a dramatic effect on the probability of isolating an antibody with a given p[K] value, depending upon what point on the curve is given by the library size.

The applicants have realised that the limitations of transformation efficiency (and therefore the upper limit on library size) can be overcome by efficient methods of introducing DNA into cells. In the preferred configuration, heavy and light chain genes are cloned separately on two different replicons, at least one of which is capable of being incorporated into a filamentous particle. Infectious particles carrying one chain are infected into cells harbouring the complementary chain; infection frequencies of >90% can be readily achieved. Heavy and light chains are then able to associate post-translationally in the periplasm and the combination displayed on the surface of the filamentous particle by virtue of one or both chains being connected to g3p. For example, a library of $10^7$ heavy chains is cloned as an unfused population in a phagemid, and $10^7$ light chains are cloned as g3 fusions in fd-DOG-1. Both populations are then expanded by growth such that there are $10^7$ of each heavy chain-containing cell and $10^7$ copies of each light chain phage. By allowing the phage to infect the cells, $10^7 \times 10^7 = 10^{14}$ unique combinations can be created, because there are $10^7$ cells carrying the same heavy chain which can each be infected by $10^7$ phage carrying different light chains. When this is repeated for each different heavy chain clone then one ends up with up to $10^{14}$ different heavy/light combinations in different cells. This strategy is outlined in FIG. 2, which shows the heavy chain cloned as g3 fusions on phage and the light chains expressed as soluble fragments from a phagemid. Clearly, the reverse combination, light chains on phage, heavy chain on phagemid, is also tenable.

Figure 2:
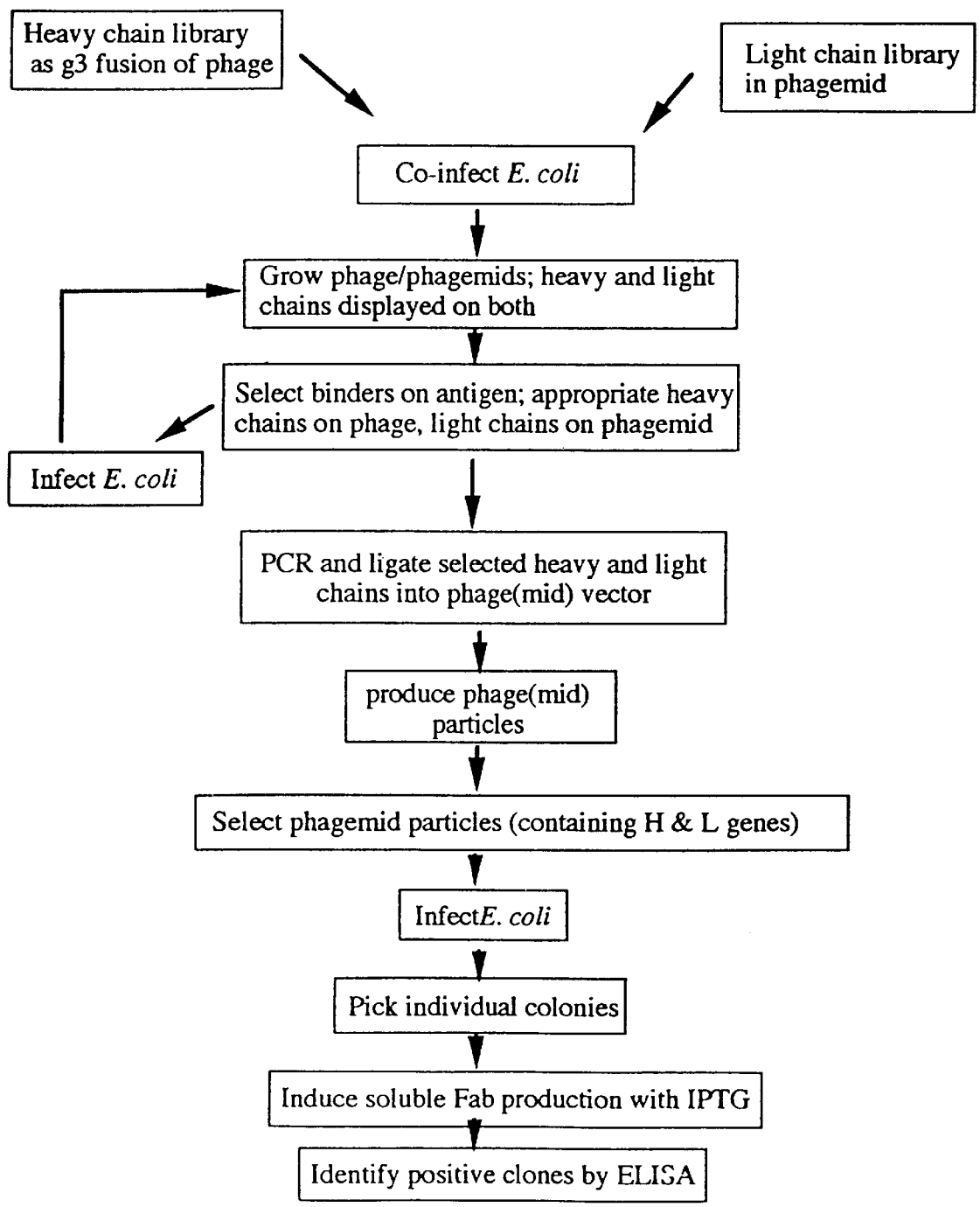
FIG. 2 outlines a strategy to clone heavy chain as g3 fusion on phage, light change being expressed as soluble fragments from a phagemid.

In this configuration shown in FIG. 2, fd-DOG 'rescues' the phagemid so that both phage and phagemid DNA is packed into filamentous particles, and both types will have paired heavy and light chains on their surface, despite having the genetic information for only one of them. For a given antigen or epitope, the vast majority of the heavy and light chain pairings will be non-functional, so that selection on antigen will have the effect of vastly reducing the complexity of the heavy and light chain populations. After the first round of selection the clones are re-assorted, in this example by infecting fresh host cells and selecting for both replicons. After several rounds of antigen selection and recovery of the two replicons, the considerably reduced heavy and light chain populations can be cloned onto the same replicon and analysed by conventional means. One technical problem with this arrangement is so-called 'interference' between filamentous phage origins of replication carried on different replicons as a result of competition for the same replication machinery. This problem can be ameliorated by construction of 'interference-resistant' mutants of either phage and/or phagemid origins (Johnston, S. and Ray, D. S. Interference between M13 and oriM13 plasmids is mediated by a replication enhancer sequence near the viral strand origin. (1984) J.Mol.Biol. 177, 685–700) or through control of copy number e.g. by replacing the origin of double-stranded replication on the phagemid (distinct from filamentous phage intergenic region) with that of, for example, a temperature sensitive runaway replicon. In this way the copy number of the resident phagemid can be kept down to minimise interference so that the phage can establish, then the phagemid copy number allowed to increase for expression of the antibody.

Figure 3:
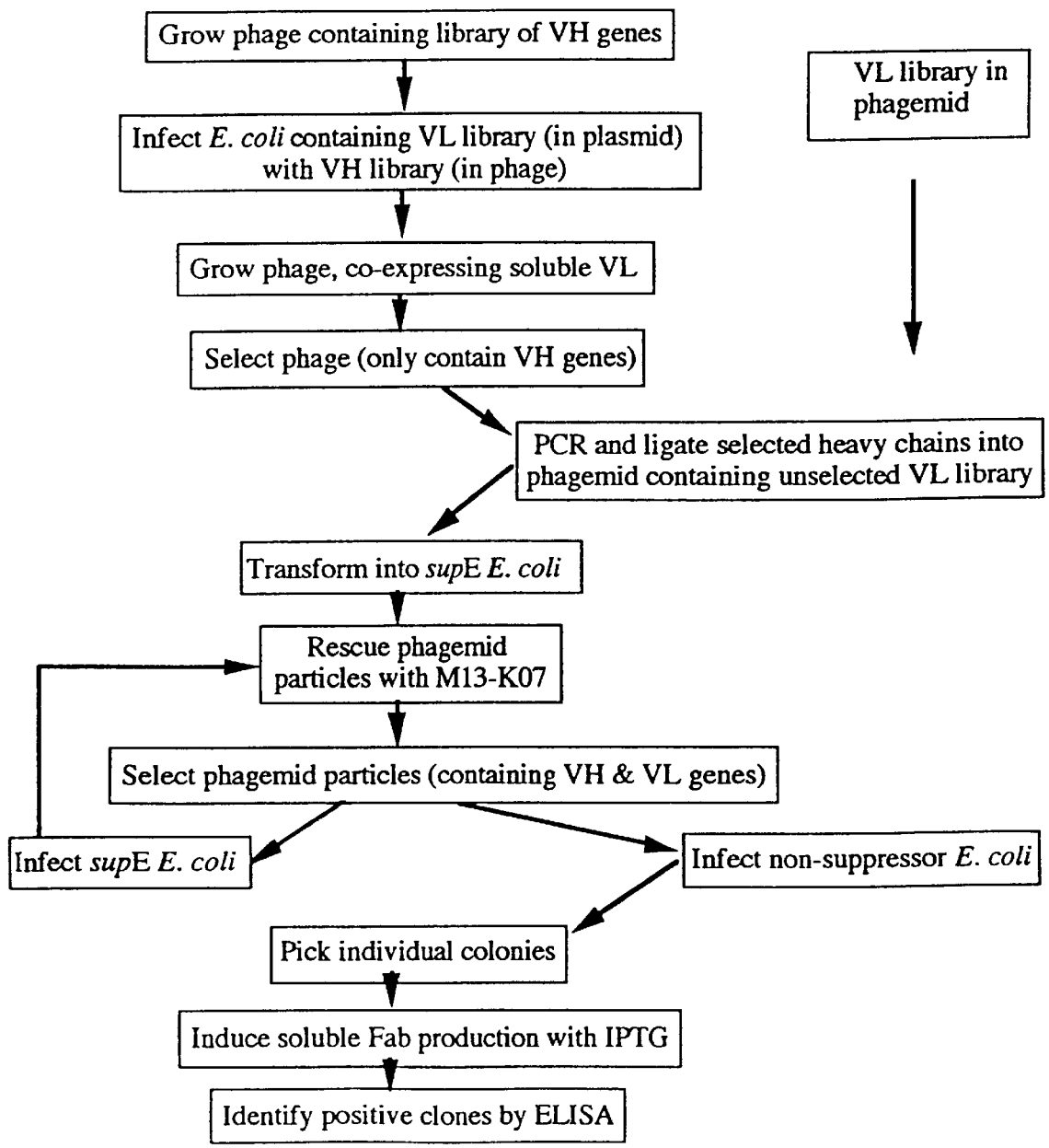
FIG. 3 shows a cloning strategy wherein only one of the two replicons is capable of being packaged into a filamentous particle.

Alternatively, only one of the two replicons need be capable of being packaged into a filamentous particle. Such a strategy is outlined schematically in FIG. 3 and reduced to practice in example 2. A library of light chains is cloned in the plasmid pUC19 and the heavy chains are expressed as g3 fusions in fd-DOG-1. There is no interference in this case since the replication mechanisms are distinct. The main operational difference here is that the process results in selection of, in this case, the best heavy chains; the light chains are not cloned. The appropriate light chains are isolated later when the selected heavy chains are cloned together with the repertoire of light chains on the same replicon, then selected conventionally.

Again, this principle can be translated into an array of alternative formats with different combinations of vectors, chains and g3 fusions as shown in FIG. 4.

Figure 5:
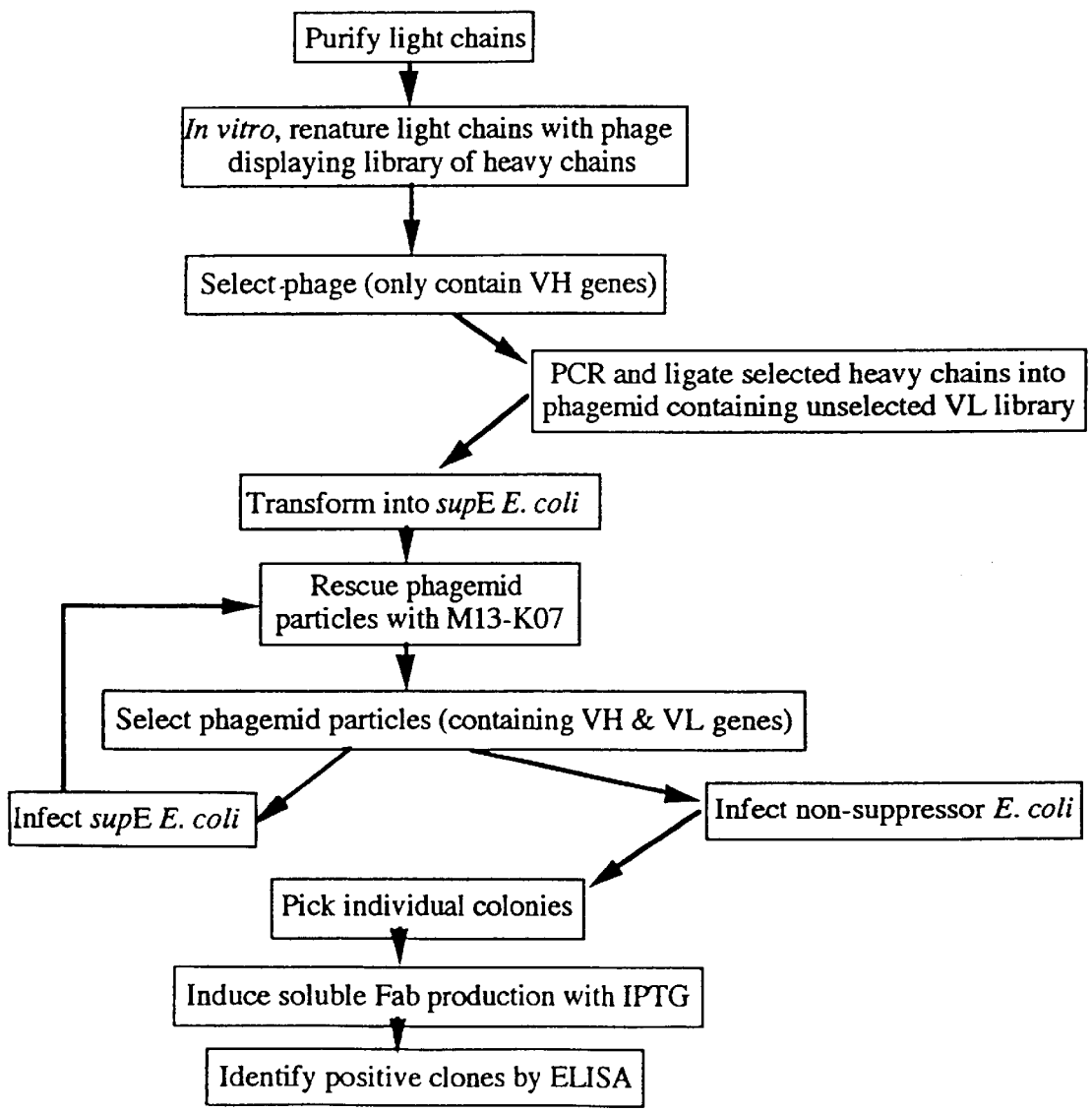
FIG. 5 shows a strategy for cloning heavy chains as g3 fusions on phage with combination with purified light chains in vitro.

Another configuration is to clone the heavy chains as g3 fusions on phage and add purified light chains in vitro, as shown in FIG. 5. These chains are partially denatured by the addition of Guanidine hydrochloride to 5M final concentration, then the denaturant dialysed away so that heavy and light chains assemble to create functional antibody combining sites on the phage surface, which can then be selected on antigen and the appropriate heavy chain phage isolated. If necessary, the selection can be repeated with fresh light chain. Appropriate concentrations of other denaturants such as Urea or Potassium isothiocyanate will also prove effective. Having operated this procedure, one is left with a vastly reduced population of heavy chain genes which can then be cloned together with the light chain repertoire, preferably on the same replicon. The soluble chain can be produced by recombinant DNA technology, one or more monoclonal antibodies or from serum antibody. The reverse configuration, i.e. light chain on phage in conjunction with soluble heavy chain, or fragments of heavy chain, is also tenable. Also contemplated are alternative methods of linking heavy and light chains, which could be linked for example, by chemical modification.

Figure 6I:
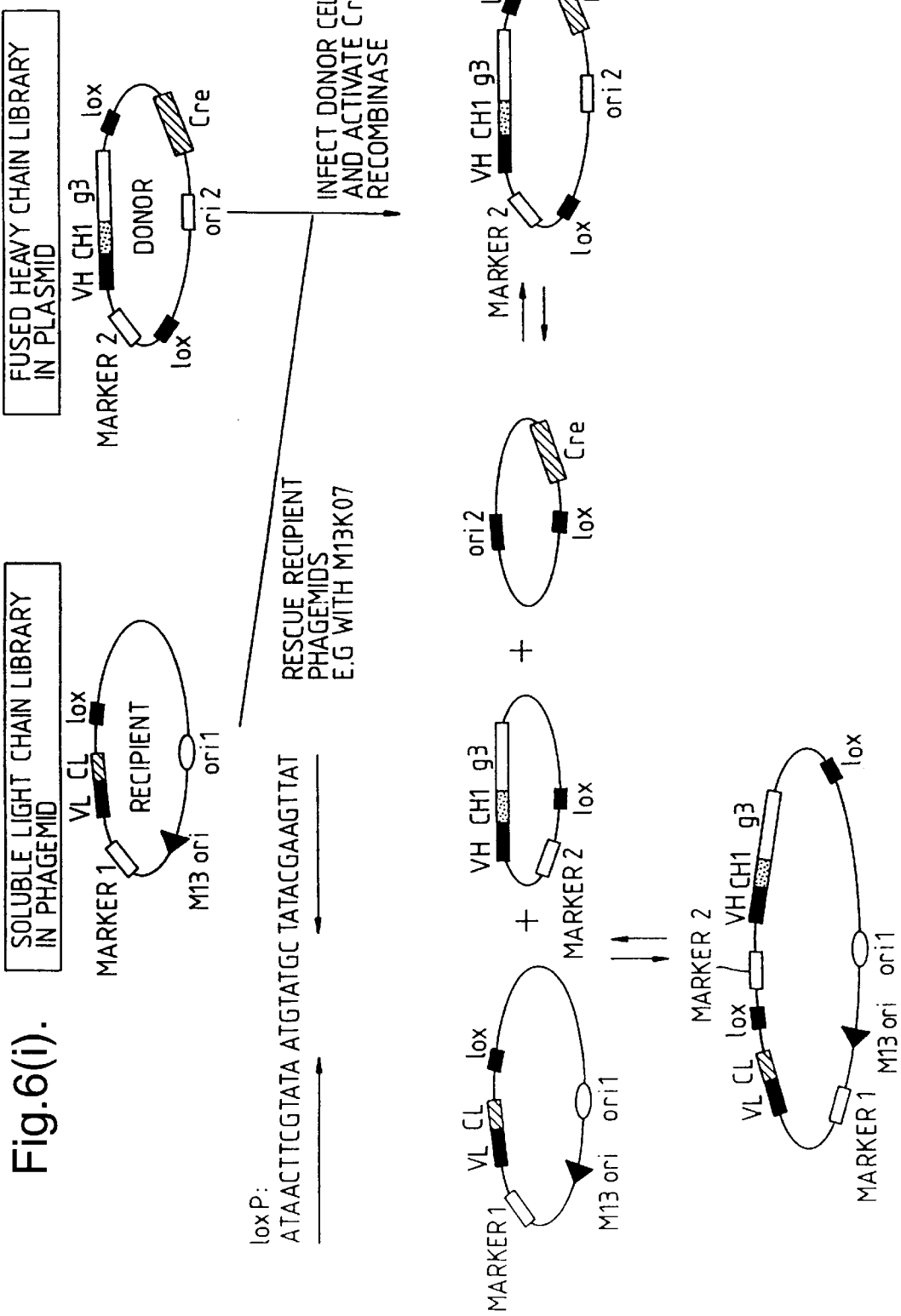
FIGS. 6(i) and 6(ii) illustrate the use of sites specific recombination for construction of polycombinantorial libraries.
Figure 6:
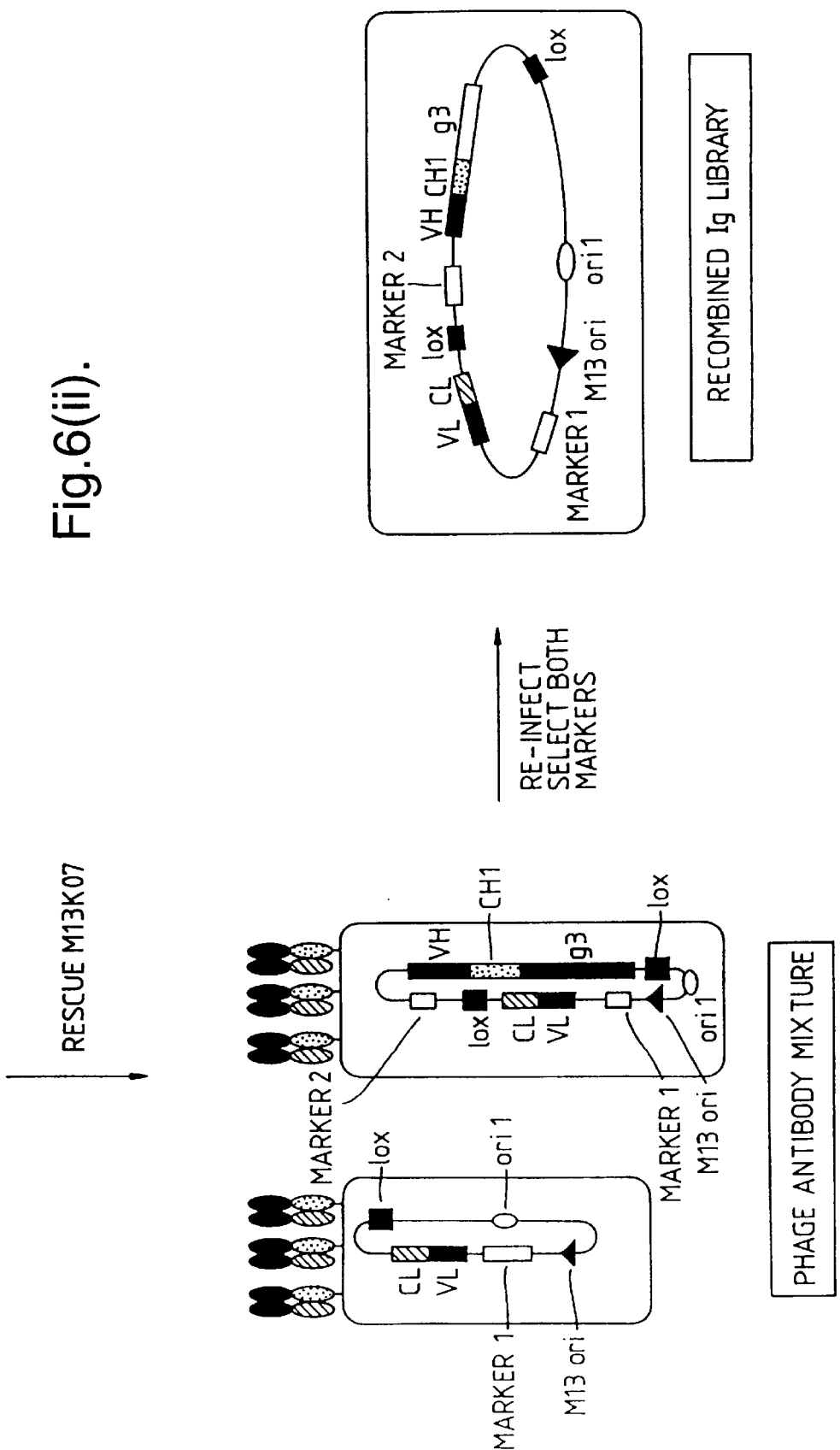

So far, the procedures described work on the principle of first reducing the complexity of the repertoire with possible subsequent recloning one or both chains of the reduced population. Alternative methods enabling both chains to be cloned on the same replicon with high efficiency have also been devised. These again rely on cloning heavy and light chain genes on separate replicons, but this time with the aim of promoting recombination between the two vectors so that both chains are placed on the same replicon. A schematic is shown in FIGS. 6(i)–(ii) in which the recombination system is based on the lox P/Cre recombinase system of coliphage P1 (Hoess, R. H. and Abremski, K. (1990) The Cre-lox recombination system. In 'Nucleic acids and Molecular Biology'. Eckstein, F. and Lilley, D. M. J. eds. Vol 4, pp99–109, Springer-Verlag, Berlin, Heidelberg). Cre-recombinase catalyses a highly specific recombination event at sequences called lox.lox P, the recombination site in phage P1 consists of two 15bp inverted repeats separated by an 8bp non-symmetrical core FIGS. 6(i)–(ii). In the configuration detailed in FIGS. 6(i)–(ii) soluble light chain is cloned onto a phagemid containing a single lox P site. The heavy chains are cloned onto a plasmid as 3g fusions. Alongside the g3 fusion is the gene for a selectable marker, and the heavychain/g3/marker sequence flanked by two lox P sites. This plasmid also contains the Cre recombinase on a regulatable promoter and has an origin of double-stranded replication that is compatible with that on the phagemid in addition to that on the helper phage e.g. p15A, RSF 1010 and col E1 origins will co-exist in the same cell. The phagemids are then infected into cells containing the donor plasmic and the Cre recombinase promoter induced, so that recombination between the lox P sites occurs inside infected cells. Some of these recombination events will lead to the heavychain/g3/marker sequences transferring as a block onto the phagemid at its single lox P site. Phagemids are then rescued with a helper phage such as M13K07 and the resulting phagemid particles either directly selected on antigen or infected into fresh host cells and grown with selection for the presence of both markers; one from the phagemid itself and the other from the heavychain/g3/marker block.

The use of site-specific recombination to bring genes onto the same replicon may be extended to creation of a continuous coding sequence on the same replicon, for example to construct single-chain Fv molecules. There is a single open reading frame in the loxP sequence that could be incorporated into an scFv linker which would then be a substrate for Cre-catalysed site-specific recombination. Placement of such modified scFv linker sequences at one or both ends of the genes to be fused can then result in creation of continuous open reading frames in vivo or in vitro when Cre recombinase is provided.

The strategy can be refined further if the Crecatalysed recombination takes place in a polA strain of bacteria, preferably E. coli or other gram negative bacterium; these cells are deficient in DNA polymerase I and are unable to support replication of plasmids (Johnston, S. and Ray, D. S. 1984, supra). However, they are able to support replication of filamentous phage and plasmids containing filamentous phage intergenic regions. By selecting for the presence of both selectable markers in the same pol A cell, successful recombination events are enriched, since recombination must take place for the second marker gene to be replicated and expressed. The resulting cells are now the complete repertoire and can be propagated as cells and infected with helper phage to produce phagemids containing the genes for both chains and expressing them on their surface.

Other general and/or site-specific recombination mechanisms could also be used to effect the same outcome (In "*Escherichia coli* and *Salmonella typhimurium*. Cellular and Molecular Biology." (1987). pp1034–1043, 1054–1070. Neidhart, F. C. Editor in Chief. American Society for Microbiology).

It will be apparent that the concept of using two or more replicons to generate diversity is not confined to display on the surface of filamentous bacteriophages. For example, bacteria could be used as the replicable genetic display package. For example, Fuchs et al. have shown that functional antibody can be displayed on the surface of *E. coli* by fusion to peptidoglycan-associated lipoprotein (Fuchs, P., Breitling, F., Dubel, S., Seehaus, T and Little, M. (1991) Targetting of recombinant antibodies to the surface of *Escherichia coli*: fusion to a peptidoglycan associated lipoprotein. BioTechnology 9, 1369–1373). Klauser et al. describe transport of a heterologous protein to the surface of *E. coli* by fusion to Neisseria IgA protease (Klauser, T., Pohler, J. and Meyer, T. F. (1990) Extracellular transport of cholera toxin B subunit using *Neisseria* IgA protease B domain: conformation-dependent outer membrane translocation. EMBO 9, 1991–1999). Other surface proteins such as pili, ompA or the surface-exposed lipoprotein Tra T could also be used, and gram positive organisms such as lactobacilli and streptococci employed. Cloning and expression in eukaryotic organisms is also contemplated.

Alternative cloning strategies are possible when cells are used in place of phage. For example, replicons can be introduced into the cells by conjugation, in addition to transformation and infection. Moreover, one or more genes can be incorporated into the chromosome reducing the limitation of having to use compatible replicons.

The polycombinatorial concept is also particularly advantageous for mutagenesis experiments by allowing far greater number of mutant progeny to be produced.

The applicants have realised that the polycombinatorial concept is applicable to multimeric proteins other than antibodies, such as T cell receptors, CD3 and insulin receptor. Libraries of proteins having more than two different and diverse subunits can be created by, for example, more than one cycle of infection. Cells containing one of the subunits are infected with phage containing the second subunit and the resulting population infected a second time with a compatible phage carrying the third subunit.

In some cases, it is advantageous to express two or more component polypeptide domains of a multimer as g3 fusions. This will have the benefit of stabilising weak interactions between separate chains, or stabilising polypeptide domains which interact weakly, or polypeptide domains which only associate in the presence of ligand.

The numbers of combinations possible with the polycombinatorial approach is limited only by the number of clones present in each of the repertoires, and, in the specific instance of using phage supplying one chain to infect cells containing the other, by the numbers of phage and cells that can be produced. The use of more sophisticated methods, for example fermentation technology, will allow even greater numbers of combinations to be accessed.

PCT/WO91/17271 filed by Affymax Inc. describes the expression of antibody heavy and light chains but does not indicate that infection of cells harbouring one replicon with phage harboring another replicon allows libraries of greater size to be constructed. Neither does it describe the selection process for selecting an antibody fragment of interest using the two replicons. They only contemplate double selection to maintain the two chains together in the same phage or bacterium, which, in the format they describe, will limit the size of the library which can be constructed. There is no indication that with heavy and light chain libraries on separate vectors, the heavy and light chains would get reshuffled, or how to identify the desired combination.

A key difference over previous approaches is the use of separate sources of heavy and light chains and the way in which they are combined to produce libraries of greater diversity. The applicants provide methods for the construction of such libraries and teach how heavy and light chain libraries may be combined to produce enormous numbers of functional combinations, and means by which desired combinations may be selected and isolated. The key advantage is that libraries constructed this way can be several orders of magnitude larger than has previously been possible. Where two replicons are used, they can be any pairwise combination of phage, phagemid and plasmid, in all cases with the antibody chains expressed as soluble fragments or associated with the phage capsid. At least one of the vectors is capable of being incorporated into an infectious phage-like particle and at least one of the vectors enables association of the antibody chain with the phage capsid, for example by fusion to g3p. Any of the above configurations can be used in novel humanisation/mutagenesis procedures.

The "chain-shuffling" combinatorial approach is a particularly useful embodiment of the present invention. One may take for instance, a single heavy chain, or a restricted number of heavy chains from an antibody known to have the desired antigen specificity of even from a repertoire of antibodies from human or animal immunised with an antigen of interest, and combine a population of such chains with a, perhaps very large, genetically diverse population of, in this instance, light chains fused to a rgdp component. The light chains would be expressed from nucleic acid capable of being packaged in a rgdp. One would then select for rgdps which each a display light chain with an associated heavy chain forming an antibody specific for an antigen of interest. Such rgdps would each contain nucleic acid encoding a light chain. Light chains of the restricted population so selected would then be combined with a genetically diverse population, perhaps a very large population, of heavy chains fused to a rgdp component and expressed from nucleic acid capable of being packaged in rgdps. A second round of selection for rgdps displaying specific binding pair members specific for the antigen of interest would yield a restricted population of heavy chains capable of associating with the previously selected light chains to form antibodies of the desired specificity.

This technique enables reduction of population diversity to an easily manageable level whilst sampling a very large number of combinations. Nothing in the prior art approaches this. It may be used advantageously in the humanisation of antibodies isolated/purified from a non-human animal source.

The following examples illustrate how these concepts may be put into practice. It will be evident to those skilled in the art that many variations on these themes will produce satisfactory results. The following examplify the concept by way of illustration only and not by way of limitation.

EXAMPLE 1

Rescue of phagemid with phage fd-DOG-1.

In this example, the concept of using a phage to 'rescue' a phagemid (FIG. 2) is tested using model chimaeric antibody.

One chain is expressed in pUC19, pUC119 or PHEN-1 as a soluble periplasmic protein and the corresponding chain cloned on fd-DOG-1 as a g3 fusion. Both chains have come from a model Fab fragment cloned in pUC19, in which the light and heavy V-region domains from the mouse anti-phOx (2-phenyl-5-oxazalone) antibody NQ10.12.5 have been fused to human C and C 1 domains respectively. The C-terminal cysteine residues, which normally form a covalent link between the light and heavy chains, have been deleted from both constant domains in this construct, and this feature is retained in subsequent constructs. The sequence of the template clone is shown in FIGS. 7(i)–(ii).

The strategy for cloning heavy and light chains as separate elements is depicted in FIG. 8; briefly, the chains were separately PCR amplified with primers that incorporate appropriate restriction sites onto the ends of the fragments. These fragments were then cloned into pHEN-1 and fd-DOG-1 in both configurations i.e. heavy chain on phage, light chain on phagemid and vice versa. The heavy chain Sfi I-Not I fragments were also cloned into pUC19 and pUC119 derivatives which have had the polylinker between the Eco RI and Hind III sites replaced with the sequence shown in FIG. 9, which contains compatible Sfi I and Not I sites. These clones are called pUC19/pUC119 Sfi-Not polymyc. The pHEN-1 clones were transformed into E. coli strain HB2151 which is a male, laciq and a non-suppressor, causing the amber codon in pHEN-1 to be read as a stop codon, thereby producing soluble chain exported to the periplasm. The remainder of the constructs were transformed into E. coli TG1.

These cells are then 'rescued' with fd-DOG-1 phage carrying the partner chain as a g3 fusion, and resulting phage/phagemid population assayed for phOx binding in ELISA.

In this example, sections a) to g) describe preparation of plasmid, phagemid and ophage clones; sections i) and j) show the effect of using phage to rescue phagemid or plasmid, and the effect that has on antibody expression.

a) PCR amplification of heavy and light chains

Plasmid pUC19 Fab NQ10.12.5DNA was used as the template for PCR amplification. Four separate PCR reactions were set up, with the following pairwise combinations of primers (TABLE 1):

Heavy chain fd-DOG-1 phage: VHLBACKAPA & FABNOTFOH
Heavy chain pHEN-1 phagemid: VHLBACKSFI & FABNOTFOH
Light chain fd-DOG-1 phage: MVKBAAPA & FABNOTFOK
Light chain pHEN-1 phagemid: MVKBASFI & FABNOTFOK PCR reactions contained 10M Tris-HCl(pH8.3), 50 mM KCl, 1.25 mM each dNTP, 2.5 mM Mg C12, 0.01% gelatin, 0.1 unit/$\mu$l Taq polymerase (Cetus/Perkin Elmer), 1 mM each primer and 1 ng of template DNA. PCR was carried out in a Techne PHC-2 thermal cycler (Techne, Duxford, Cambridge U.K.) using 25 cyles of 1 minute at 90° C., 1 minute at 50° C. and 2 minutes at 72° C.

b) Digestion of PCR fragments

The resultant products were extracted with 1:1 phenol:chloroform then ethanol precipitated as described in Sambrook et al. (Sambrook, J., Fritsch, E. F. and Maniatis, T. (1989)) "Molecular cloning-a laboratory manual". Cold Spring Harbor Laboratory, New York.), and pelleted DNA redissolved in 35 $\mu$l water. Restriction digest were normally carried out in 100–200 $\mu$l volumes with 0.3–0.4 units enzyme/$\mu$l (volume of enzyme added not to exceed ½0th of the total reaction volume) using conditions reccomended by the manufacturer, and in the buffer supplied by the manufacturer. Digestion with 0.4 units/$\mu$l Not I enzyme (New England BioLabs) was carried out in 150 $\mu$l volume according to manufacturers instructions and in the buffer provided by the manufacturer for 3 hrs at 37° C. The products were phenol:chloroform extracted and ethanol precipitated once more and digested either with ApaLI or Sfi I. Apart from the Apa LI digest of the VHCH1 Apa LI-Not Ifragment (see below), digestions were carried out using 0.4 units/$\mu$l enzyme in a total of 150 $\mu$l according to manufacturers instructions (New England BioLabs) and in the buffer provided by the manufacturer. Apa LI digests were carried out for 3 hrs at 37° C., Sfi I for 3 hrs at 50° C.

The Apa LI digest of the VHCH1 Apa LI-Not I fragment had to be a partial due to the presence of an internal Apa LI site. This was achieved by digestion with 0.04 units/$\mu$l Apa LI for 1 hour and the full-length fragments isolated from an agarose gel (see below).

c) Purification of DNA fragments

Reaction products were ethanol precipitated to reduce their volume then run on a preparative 2% Low Melting Point agarose/TAE (Tris-Acetate EDTA) gel, the ca. 700 bp bands excised and the DNA fragments purified using a Geneclean kit in accordance with the manufacturers instructions (Bio 101, La Jolla, Calif., USA). DNA fragments were resuspended in TE (10 mM Tris-HC1 (pH 8.0), 0.1 mM EDTA) and ligated to prepared vector (sections d and e).

d) Preparation of vector DNA

10 μg caesium chloride-purified fd-DOG-1 was digested with Apa LI and Not I as above. 10 μg caesium chloride-purified pUC19 Sfi/Not, pUC119 Sfi/Not and pHEN-1 DNAs were digested with Sfi I and Not I, using the same conditions as those described in b) above. Following digestion and ethanol precipitation, vector DNA was phosphatased with 1 unit Calf Intestinal Alkaline Phosphatase in 50 μl of the buffer recommended and supplied by the manufacturer (Boehringer Manheim UK Ltd., Bell Lane, Lewes, East Sussex, BN7 1LG) as a 10× stock, for 30 minutes at 37° C., then another 1 unit of enzyme added and the incubation repeated. Forty μl of water, 10 μl of 10× STE (10× STE is 100 mM Tris-HC1, pH (8.0), 1M NaCl, 10 mM EDTA) and 5 μl 10% SDS was then added and the mixture incubated at 68° C. for 20 minutes to inactivate the phosphatase. The mixture was then cooled on ice briefly and extracted twice with 1:1 phenol:chloroform then ethanol precipitated as described in Sambrook et al. (1989, supra).

e) Ligations

The following ligations were set up:

pUC19 Sfi I-Not I +VHCH1 Sfi I-Not I pUC119 Sfi I-Not I +VHCH1 Sfi I-Not I pHEN Sfi I-Not I +VHCH1 Sfi I-Not I pHEN Sfi I-Not I +VLCL Sfi I-Not I fd-DOG Apa LI-Not I +VHCH1 Apa LI-Not I (partial Apa LI)

fd-DOG Apa LI-Not I +VLCL Apa LI-Not I

For each, the following ligation reaction was set up:

10× NEB-Ligation Buffer 1 μl water 6 μl

Digested vector (30 ng/μl 2 μl

Digested PCR fragment (20–50 ng/μl 1 μl

2. Spin for a few seconds in the microfuge. Then add:

T4-DNA ligase (400 units/μl, NEB) 1 μl

3. Leave for 2 hrs at 25° C. or overnight at 16° C.

4. Transform into E. coli (see below).

Note: 10× NEB-Ligation Buffer is 0.5M Tris-CH1, pH 7.8, 0.1M MgCl$_2$, 0.2M DTT, 10 mM rATP and 500 μg/ml BSA.

f) Electroporation into TG1 or HB2151

1. Thaw a vial of electroporation-competent bacteria on ice. For soluble expression of antibody fragments from pHEN1, the non-suppressor strain HB2151 is used. For the others, TG1 is used.

2. Transfer 50 μl cells to a prechilled 0.2 cm cuvette (Biorad), add 2 μl ligation mix, shake to the bottom and sit on ice for 1 min.

3. Set up the Gene Pulser (Biorad) to give 25 μF, 2.5 kV with the pulse controller set to 200 ohms.

4. Dry the cuvette with tissue and place in the electroporation chamber.

5. Pulse once (should yield a pulse with a time constant of 4.5 to 5 msec).

6. Immediately add 1 ml of SOC (fresh) to the cuvette and resuspend the cells.

7. Transfer to disposable culture tube, and shake for 1 hr at 37° C.

8. Plate fractions on 2YT agar plates containing 100 μg/ml ampicillin, 1% glucose for PHEN and pUC replicons or 2YT agar plates containing 15 μg/ml tetracycllin for fd-DOG.

Note 1: SOB is 20 g Bacto-tryptone, 5 g Yeast extract and 0.5 g NaCl, in 1 litre. SOC is SOB with 5 ml 20% glucose, 1 ml 1M MgCl$_2$ and 1 ml 1M MgSO$_4$ added per 100 ml. 2YT is 20 g Bacto-tryptone, 10 g Yeast extract and 5 g NaCl, in 1 litre.

Note 2: To increase transformation efficiencies the DNA in the ligation mix can be purified by extracting with phenol, phenol-chloroform and ether, ethanol precipitating and resuspending in water. Alternatively the samples can be cleaned up using Geneclean (Bio 101). Efficiencies will go up 10–100 fold if this purification step is included.

The desired clones were screened by PCR with the primers used to clone the fragments and their identity confirmed by DNA sequence analysis. Infectious particles were then produced from these clones (see below).

g) Preparation of fd-DOG infectious phage particles

1. Inoculate colony of bacteria containing fdDOG into 2YT broth containing 15 μg/ml tetracycline. Grow 37° C., shaking for 20–24hrs. The yield of phage particles should be about $10^{10}$ TU (transducing units-see below) ml$^{-1}$ of supernatant.

2. Spin 8,000 r.p.m. for 10 min (or 4,000 r.p.m. for 20 min).

3. To supernatant add ⅕th volume PEG/NaCl (20% PEG 6000, 2.5M NaCl), leave 1 hr at 4° C. Spin 8,000 r.p.m. for 15 min (or 4,000 r.p.m. for 30 min).

4. Resuspend pellet in a small volume of water and transfer to eppendorf tubes.

5. Spin down any remaining cells (5 min in microfuge).

5. To the supernatant add ⅕th volume of PEG/NaCl.

6. Remove supernatant and respin the pellet briefly.

7. Aspirate off any remaining PEG.

8. Resuspend the pellet in water (1/100th original volume of culture) and respin 2 min in microfuge to remove residual bacteria and agglutinated phage. Filter through 0.45μm sterile filter (Minisart NML; Sartorius).

9. Store the filtrate at 40° C. The concentration of phage should be about $10^{12}$ TU ml$^{-1}$.

h) Infection experiments

Preliminary experiments using fd-DOG phage to infect pHEN-1 suggested that there is interference between the two vectors because both carry a filamentous phage intergenic region, causing competition for the same replication machinery. The experiments below confirm this.

TG1 cells, either untransformed or harbouring pUC19, pUC119, pUC19 NQ10.12.5 chimaeric VHCH1 and pUC119 NQ10.12.5 chimaeric VHCH1 were grown to mid-log phase at 37° C. in 2YT medium, without antiboitic for TG1 or containing 100 μg/ml ampicillin and 1% glucose for the recombinants. Cultures were then diluted to contain ca. $10^8$ cells/ml using the approximation O.D.$_{600}$ $1.0=5.10^8$ colony forming units (cfu)/ml, and fd-DOG phage added to $3.10^9$ tetracycline resistance transducing units (TU, assayed on TG1) per ml. After incubation at 37° C. for 30 minutes, dilutions were plated on 2YT agar containing 15 μg/ml tetracyclin and 1% glucose and incubated at 37° C. overnight to give the number of successful infection events (=number of tet$^r$ colonies). The result is shown graphically in FIG. 10. There is little difference in titre when fd-DOG phage infect TG1 cells or TG1 cells containing pUC19- the titre is equal to the number of input cells (since in this experiment phage were in excess). However, when the host cell contains pUC119 (or any vector based on pUC119) the number of healthy tetr colonies (2–3 mm diameter) is reduced ca. 100-fold, and there are now numerous tiny colonies (0.3–0.5 mm diameter). These small colonies do not grow in liquid culture with tetracycline, and, as the number of small+large colonies=input number of cells it is believed that they are infection events in which the phage has not established.

The presence of an antibody heavy chain in pUC19 or pUC119 has little effect on yield of tetr colonies after infection with fd-DOG and the number of successful infection events assayed by plaque numbers (FIG. 10). The ability to recover functional antibody on the surface of phage was then tested - sections i and j below.

i) Rescue of Fab phage

The following rescues were set up; all chains are NQ10.12.5 chimaeras:

pUC19 Heavy chain X fd-DOG-Light chain
pUC119 Heavy chain X fd-DOG-Light chain
pHEN Heavy chain X fd-DOG-Light chain
pHEN Light chain X fd-DOG-Heavy chain
PHEN Light chain X fd-DOG-Light chain
pHEN Heavy chain X fd-DOG-Heavy chain Host cells (HB2151 for pHEN-1, TG1 for pUC) containing plasmid/phagemid with one of the two Fab chains were grown overnight at 37° C. in 2YT containing 100μg/ml ampicillin and 1% glucose (2YTAG). Glucose is used to repress the lac promoter and thereby reduce expression of the antibody gene. The stationary cultures were diluted 1:100 into 10 mls fresh 2YTAG in a 50 ml polypropylene tube (Falcon) and grown at 37° C. to an $O.D._{600}$ of 0.5 before adding concentrated fd-DOG phage containing either the heavy or light chain genes a s g3 fusions to $1.10^9$ TU/ml final concentration. These cultures were then incubated at 37° C. without shaking for 30 mins the n with rapid shaking for another 30 mins. Cells were then pelleted by centrifugation at 4,000×g for 20 mins at 4° C., the tubes drained and the cells resuspended in 10 mls fresh 2YT containing 100 μg/ml tetracyclin (no glucose→induction) and grown with vigorous shaking overnight at 37° C.

The next day, cells were pelleted by centrifugation at 4,000×g for 20 mins at 4° C., and the supernatant assayed for the presence of functional antibody by ELISA.

j) ELISA

1. Coat plate (Falcon 3912) with 100 μl of phOX-BSA (14:1 substitution) per well at 10 μg/ml, in PBS. Leave overnight at room temp.
2. Rinse wells 3× with PBS, and block with 200 μl per well of 2% Marvel/PBS, for 2 hrs at 37° C.
3. Rinse wells 3× with PBS, then add 25 μl 10% Marvel/PBS to all wells.
4. Add 100 μl culture supernatant to the appropriate wells. Mix, leave 2 hrs room temp.
5. Wash out wells 3 times with PBS, 0.05% Tween 20 and 3 times with PBS. Add 100 μl sheep anti-M13 antiserum diluted 1:1000 in 2% Marvel/PBS into each well. Incubate at room temp. for 1.5 hrs.
6. Wash out wells 3 times with PBS, 0.05% Tween 20 and 3 times with PBS. Pipette 100 μl of 1:5000 dilution of anti-sheep IgG antibody (peroxidase-conjugated, Sigma). Incubate at room temp. for 1.5hrs.
7. Discard 2nd antibody, and wash wells 3 times with PBS, 0.05% Tween 20 and 3 times with PBS.
8. Add one 10 mg ABTS (2,2'-azino bis(3-ethylbenzthiazoline-6-sulphonic acid), diammonium salt) tablet to 20 ml 50 mM citrate buffer, pH4.5. (50 mM citrate buffer, pH4.5 is made by mixing equal volumes 50 mM trisodium citrate and 50 mM citric acid).
9. Add 20 μl 30% hydrogen peroxide to the above solution immediately before dispensing.
10. Add 100 μl of the above solution to each well. Leave room temp. 30 mins.
11. Quench by adding 50 μl 3.2mg/ml sodium fluoride. Read at 405 mm.

Note: 'Marvel' is dried milk powder. PBS is 5.84 g NaCl, 4.72 g $Ha_2HPO_4$ and 2.64 g $NaH_2PO_4.2H_2O$, pH7.2, in 1 litre.

Figure 11:
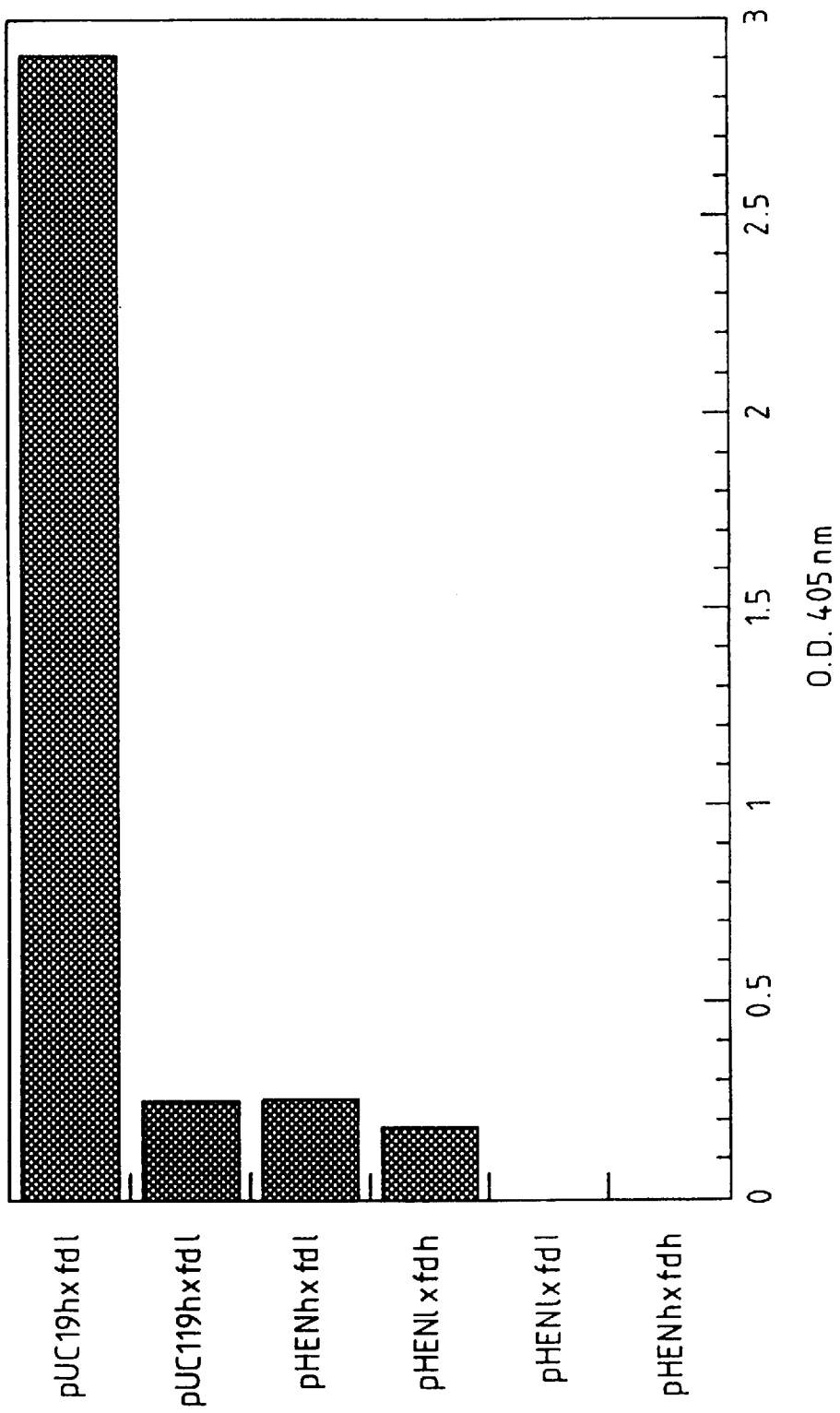
FIG. 11 illustrates the effect on ELISA signal of interference between phage and phagemid vectors, compared with phage and plasmid.

The result is shown in FIG. 11, where it can be seen that whether the resident replicon is a plasmid or a phagemid has a significant effect on the amount of antibody rescued by fd-DOG carrying the complementary chain. The signal generated from cells carrying the heavy chain on pUC19 is ca. 10× that from cells carrying this chain on pUC119 when rescued with fd-DOG carrying the light chain. pHEN gives similar results to pUC119, when the heavy chain is expressed in PHEN and the light chain on fd-DOG, and vice versa. Although weak, the signal is specific since no antibody is produced when the incoming phage carries the same chain as that on pHEN. Clearly, the use of phage carrying one chain to rescue phagemid carrying the complementary chain does work, though the system would benefit from manipulation of phage or phagemid replicons to alleviate interference. An alternative is to use a plasmid vector in conjunction with phage which will result in selection of just one of the two chains. Such a strategy is used in example 2.

EXAMPLE 2

Polycombinatorial Libraries

In this example a human VH repertoire is cloned into fd-DOG carrying the human CH1 domain of IgG1 (C 1 domain). The repertoire of light chains is cloned into pUC19 Sfi/Not/polymyc plasmid as Sfi/Not fragments and separately into pHEN phagemid flanked by an Sfi site at one end and Asc and Not sites at the other.

Fd-DOG heavy chain phage are used to 'rescue' the pUC19 light chains and the resulting phage selected on antigen. The heavy chain population is reduced in this way then PCR-amplified with primers incorporating Asc I and Not I sites and these fragments cloned alongside the unselected light chains in pHEN phagemid. The genes for both chains are now on the same replicon and can be selected simultaneously with antigen after rescue with helper phage.

The VH domains used in this example derive from IgM but are cloned as IgG1 fd (i.e. VHCH1) fragments without the C-terminal cysteine.

Sections a and b below describe construction of an fd-DOG derivative containing a human C 1 domain from which the natural Apa LI site has been deleted. Sections e to g cover preparation of the heavy and light chain repertoires. Section f describes how these repertoires may be used to isolate specific antibody fragments.

a) Construction of ΔApa LI version of CH1

Construction of a ΔApa LI version of CH1 is described here. The construction is somewhat involved since the primary purpose was construction of a new phagemid cloning vector, and removal of the Apa LI site in CH1 only one step in the procedure. The new phagemid containing the ΔApa LI version of CH1 was used as template in the next section.

The naturally-occurring Apa LI site in the human C 1 domain was deleted by 'PCR mutagenesis' using partially complementary oligonucleotides that overlap around the Apa LI site and change this sequence from GTGCAC to GTGGAC. Two PCR reactions were performed and the two fragments in a second PCR-splicing by overlap extension.

Two PCR reactions were set up as in example 1 using RJHXHOBACK in conduction with APAOUTFOR, and APAOUTBACK in conduction with HUGICYSASCNOTFOR (Table 1). Template was pUC19 Fab D1.3—this anti-lysozyme Fab has the same human IgG CH1 domain as pUC19 Fab NQ10.12.5 described in example 1. PCR conditions were as described in Example 1, except that the annealing temperature was 55° C. and extension was at 72° C. for 1 minute. The resulting fragments were purified for assembly as follows:
1. To isolate small fragments for assembly-PCR, the PCR-mixes are collected in one tube and electrophoresed on a 2% LGT (low gelling temperature) agarose gel with TBE buffer.
2. These fragments are purified using SPIN-X columns (Costar).
3. The gel slice is loaded into the cartridge of a SPIN-X column and frozen in dry ice for 10–15 min.
4. Thaw tube and repeat freezing step (optional).
5. Spin in a microfuge (appr. 13,000 r.p.m.) for 15–30 min.
6. Precipitate the filtrate by adding 1/10 vol. 3M sodium acetate, pH5.2, and 2.5 vol. ethanol.
7. Chill on dry ice for 15 min, spin at 13,000 r.p.m. for 10 min at 4° C.
8. Wash the pellet in 1 ml 70% ethanol and dry under vacuum.
9. Dilute purified linker into 5 µl water or TE per original 50 µl PCR, and measure concentration on gel.

These fragments are then joined by PCR. A 50 µl PCR reaction is set up as before, this one containing 5 µl each fragment but no primers. The reaction is held at 95° C. for 5 mins, then cycled at 94° C. 1 min, 68° C. 1 min and 72° C. 1 min, seven times. RJHXHOBACK and HUGICYSAS-CNOTFOR flanking oligonucleotides were then added under the oil and the reaction cycled another 10 times using the same conditions to amplify those molecules that have correctly assembled. The reaction product was phenol extracted and ethanol precipitated then digested with Xho I and Asc I and gel-purified, all under standard conditions.

A second fragment containing the entire gIII leader plus polylinker of fd-DOG was also amplified. Fd-DOG DNA was amplified with primers G3LASCGTGBACK and fdseq, cut with Asc I and Not I and gel-purified, all as described in example 1.

A 3-way ligation was set up with equimolar quantities of Xho I-Not I -cut pHEN DNA, Xho I-Asc I -cut C 1 fragment and Asc I-Not I -cut gIII leader+polylinker fragment. The resulting mixture was transformed into TG1 as described in example 1 and clones with the structure: pHEN-pelB leader/ Sfi I/Nco I/Xho I-C 1-Asc I/gIII Leader-Apa LI-Not I/gIII identified by alkaline lysis miniprep and restriction enzyme analysis (Sambrook et al. (1989) supra.). The integrity was verified by DNA sequencing (Sambrook et al. (1989) supra.) and a representative clone called PJIM C 1gIIIL, which carries the C 1 domain from which the internal Apa LI site has been removed.

b) Insertion of CH1 domain into fdDOG

The ΔApa LI version of CH1 was now used as a template for construction of an fd-DOG derivative containing the CH1 domain lacking the Apa LI site. In this construct the C-terminal cysteine residue normally forming a disulphide bond with the light chain was converted to serine by PCR with the FABNOTFOH primer. This vector is now suitable for cloning of the repertoire of VH domains as Apa LI-Sal I fragments.

50 ng of pJIM Cγ1gIIIL template DNA was PCR amplified in a 50 µl reaction using the conditions described in Example 1, with the primers FDGAM1BAAPA and FABNOTFOH, which bring in Apa LI and Not I sites; the FABNOTFOH primer also removes the C-terminal cysteine. The ca. 300 bp PCR fragment was then processed and digested with Apa LI and Not I using conditions described in example 1. The Apa LI-Not I fragment was then cloned into the preparation of Apa LI and Not I -cut fd-DOG DNA prepared for the experiments described in example 1, and ligated and transformed into TG1 using the same procedures.

The sequence of the vector was verified by DNA sequencing (Sambrook J. et al, 1989, supra) of single-stranded DNA isolated from filamentous particles (Sambrook J. et al, 1989, supra) prepared in the usual way (example 1) using the primer fdseq (Table 1). The vector was then CsC1-purified (Sambrook J. et al, 1989, supra) and cut with Apa LI and Sal I. Both enzymes were from New England BioLabs, and sequential digestions using 0.4 units enzyme/µl performed at 37° C. in the buffers provided by the manufacturer (see example 1).

c) Preparation of CDNA template 500 ml of blood, containing approximately $10^8$ B-lymphocytes, was obtained from 2 healthy volunteers. The white cells were separated on Ficoll and RNA was prepared using a modified method (Cathala, G., J. Savouret, B. Mendez, B. L. West, M. Karin, J. A. Martial and J. D. Baxter (1983). A method for isolation of intact, transcriptionally active ribonucleic acid. DNA 2, 329). Three first strand cDNA syntheses were made as described by Marks et al (1991, supra) from RNA corresponding to $2.5 \times 10^7$ B-cells, using an IgM constant region primer for the heavy chains, and a κ or λ constant region primer for light chains (Table 1).

d) PCR of Heavy Chains

Two preparations of PCR-amplified VH genes were made. Both preparations used an equimolar mixture of the HUJH-FOR primers (Table 1); in one of the preparations, 6 separate PCR amplifications were performed with each of the HUVHBACK primers individually (Table 1), and in the other, a single PCR reaction was performed with an equimolar mix of all 6 HUVHBACK primers. For all seven PCRs, 50 µl reaction mixtures were prepared containing 5 µl of the supernatant from the cDNA synthesis using the HUIGM-FOR primer, 20 pmol total concentration of the BACK primers, 20 pmol total concentration of the FORWARD primers, 250 µM dNTPs, 10 mM KC1, 10 mM $(NH_4)_2SO_4$, 20 mM Tris.HC1 (pH 8.8), 2.0 mM MgC12, 100 mg/ml BSA and 1 µl (1 units) Vent DNA polymerase (New England Biolabs). The reaction mixture was overlaid with mineral (paraffin) oil and subjected to 30 cycles of amplification using a Techne PHC-2 thermal cycler. The cycle was 94° C. for 1 minute (denaturation), 57° C. for 1 minute (annealing) and 72° C. for 1 minute (extension). The products were purified on a 1.5% agarose gel, isolated from the gel by Geneclean (Bio-101) and resuspended in 25 µl of $H_2O$. The seven products were then pooled and 'pullthrough' PCR reactions performed to attach Apa LI and Sal I restriction sites.

Pullthrough reactions were set up with the primers HUVHBAAPA (equimolar mix of all 6 primers) and HUJH-FORSAL (equimolar mix of all 4 primers). 50 ml reactions of containing 5 µl of the pooled PCR products from the previous step were amplified using the same conditions as for the primary PCR except that 25 cycles of amplification were used. The resulting fragments were digested with Apa LI and Sal I, gel-purified, and the fragments ligated to Apa LI and Sal I-cut fd-DOG CH1 as previously described. The ligation mixes were phenol-chloroform extracted prior to electroporation into TG1 cells (example 1). Aliquots of the transformed cells were plated on 2YT agar supplemented with 15 mg/ml tetracyclin and grown overnight at 37° C.

e) PCR of Light Chains

κ and λ-chain genes were amplified separately using an equilmolar mixture of the appropriate family based BACK and FORWARD primers (Table 1). κ-chain genes were amplified from the cDNA synthesis using HUCKFOR primer, using an equimolar mixture of the 6 HUVKBACK 1a–6a primers in conjunction with the HUCKFORSER primer. λ-chain genes were amplified from the cDNA synthesis using the HUCLFOR primer, and amplified using an equimolar mixture of the 7 HULBACK 1–6 primers in conjunction with the HUCLFORSER primer. In each case 50 µl reaction mixtures were prepared containing 5 µl of the supernatant from the appropriate cDNA synthesis, 20 pmol total concentration of the BACK primers, 20 pmol total concentration of the FORWARD primers, 250 µM dNTPs, 10 mM KCl, 10 mM $(NH_4)_2SO_4$, 20 mM Tris.HCl (pH 8.8), 2.0 mM MgCl2, 100 mg/ml BSA and 1 µl (1 unit) Vent DNA polymerase (New England Biolabs). The reaction mixture was overlaid with mineral (paraffin) oil and subjected to 30 cycles of amplification using a Techne thermal cycler. The cycle was 94° C. for 1 minute (denaturation), 57° C. for 1 minute (annealing) and 72° C. for 2.5 minutes (extension). The products were purified on a 2% agarose gel, isolated from the gel by Geneclean (Bio-101) and resuspended in 25 µl of $H_2O$.

Two different pullthrough reactions were now performed on each of the two light chain preparations. κ-chain genes were amplified in two reactions, using an equimolar mixture of the 6 HUVKHASFI primers in conjunction with either HUCKFORSERASCNOT or HUCKFORSERNOT. λ-chain genes were also amplified in two reactions, using an equimolar mixture of the 7 HUVLBASFI primers in conjunction with either HUCLFORSERASCNOT or HUCLFORSERNOT. Pullthrough conditions were performed as for the primary light chain PCRs abov except that 25 cycles of amplification were used. All 4 PCR products were digested with Nco I and Not I using the same conditions as used previously (example 1 and above). Those κ and λ-chain genes amplified with the SERASCNOT foreward primers were inserted into Nco I-Not I-cut pHEN-1 vector (prepared using the standard format); those amplified using the SERNOT foreward primers were inserted into Nco I-Not I-cut pUC19 Sfi/Nco/Not/polymyc. Both repertoires were electroporated into TG1 by the same methods as described in example 1: the ligation mixes were purified by phenol extraction and ethanol precipitated. The ligated DNA was resuspended in 10 µl of water, and 2.5 µl samples were electroporated into 50 µl *E. coli* TG1. Cells were grown in 1 ml SOC for 1 hr and then plated on 2YT agar with 100 µg/ml ampicillin and 1% glucose (2YTAG) in 243×243 mm dishes (Nunc). Colonies were scraped off the plates into 10 ml 2YTAG and 15% glycerol for storage at −70° C. as library stocks.

f) Selection of Antibody Fragments

The end result of sections a) to e) is the construction of two light chain libraries and one heavy chain library. The light chain libraries (VLCL) were cloned as Nco I-Not I fragments in both pHEN-1 and in pUC19 Sfi-Not polymyc. The VH genes were cloned as Apa LI-Sal I fragments in fd-DOG containing a human CH1 (Cγ1) domain from which the natural Apa LI site has been delted (fd-DOG G1CH1).

Figure 13I:
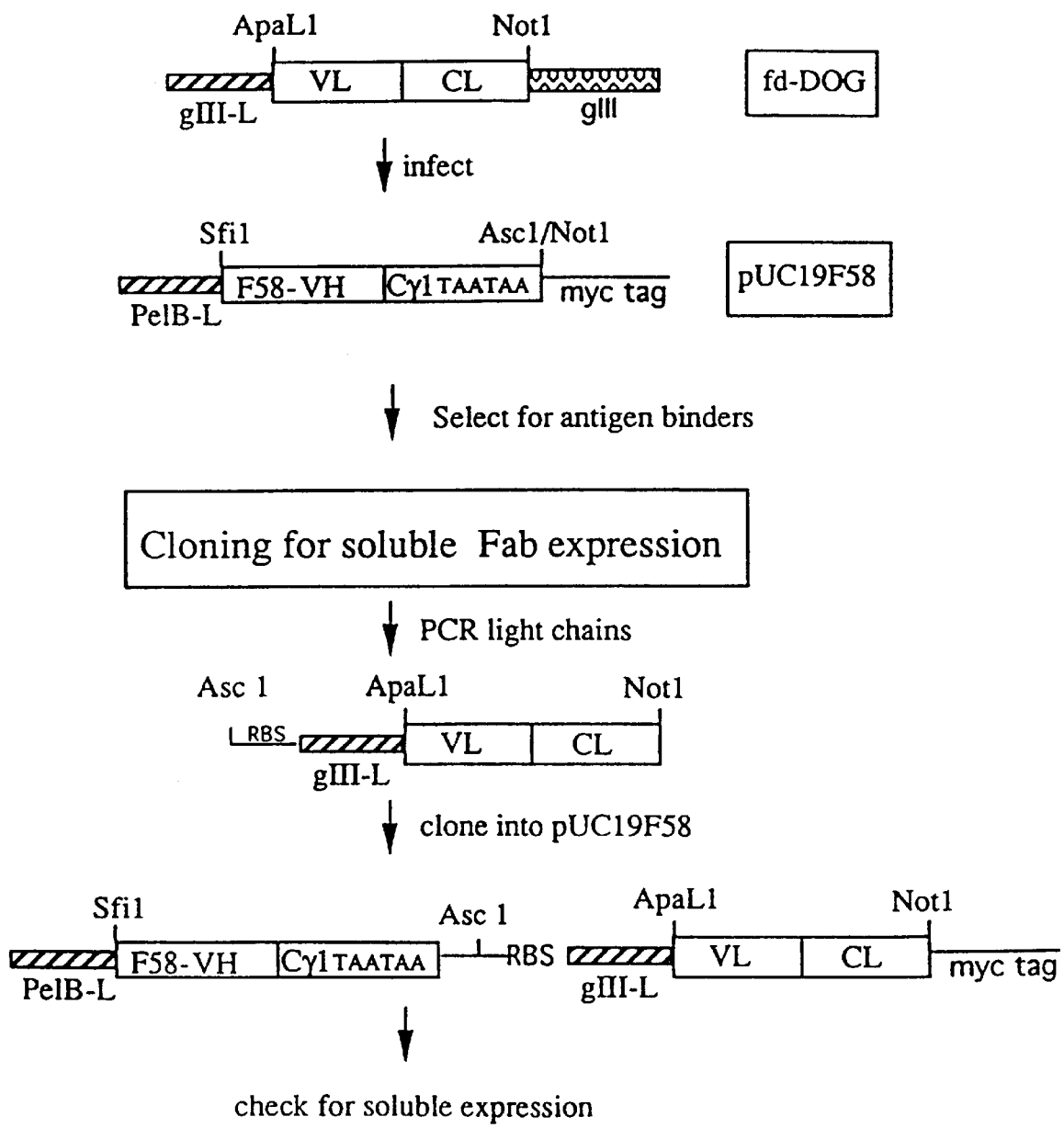
Figure 14:
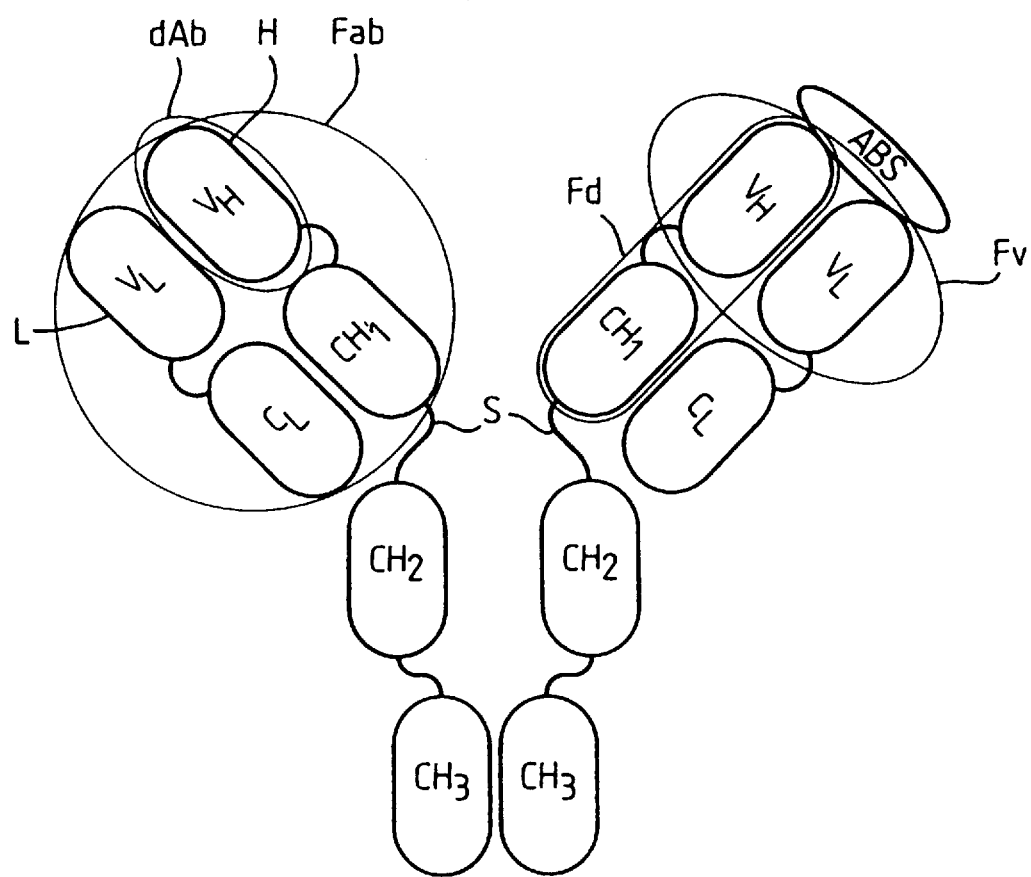
FIG. 14 shows the basic structure of the simplest antibody molecule IgG.

The process is now illustrated schematically in FIG. 13(*i*)–(*ii*). The pUC19 heavy chain library is infected with the heavy chain fd-DOG library and fd phage bearing heavy and light chain combinations on their surface produced. These phage are selected on antigen (with rounds of reinfection of the light chain library and reselection an option) and the selected heavy chain genes amplified from the phage genome using PCR with primer G3LASCGTGBACK and fdseq.

The G3LASCGTGBACK primer anneals to fd DNA upstream of the start of the natural g3 signal sequence and brings in an unique Asc I site and a ribosome binding site (RBS). Fdseq anneals at the 5' end of the structural part of g3 (i.e. downstream of the signal sequence cleavage site) which is downstream of the Not I site flanking the Cγ1 domain. The PCR fragments therefore contain: Asc I-RBS-g3 leader-VHCH1-Not I. When these fragments are cloned into the pHEN-1 light chain library as Asc I-Not I fragments, the heavy chain is fused to g3 of pHEN-1 and the Not I site is flanked by the myc tag and an amber codon.

Phagemid particles produced from these recombinants in a sup E strain not only bear heavy and light chains on their surface, they also contain the genes encoding both heavy and light chain. Selection on antigen one or more times will then result in isolation of functional heavy and light chain combinations. These clones can then be screened for antigen binding as soluble fragments when the phagemids are transferred into a non-suppressor strain such as HB2151. An efficient selection process would be particularly advantageous in this example.

EXAMPLE 3

Soluble Combinatorial Libraries

In this example either the light chain or the fd fragment of the heavy chain (i.e. VHCH1) is expressed on phage particles and the complementary chain provided as a soluble fragment. The mixture is partially denatured such that the chains separate but the domains don't unfold. The denaturant is then slowly removed by dialysis, allowing light and heavy chains to pack together so that they can be selected on antigen. The effect of this procedure is that the population of one of the two chains (whichever is attached to the phage) is greatly reduced and can then be cloned together with the repertoire of partner chains by conventional techniques.

This approach is theoretically tenable: $1 \times 10^{11}$ TU of phage provide ca. $10^{12}$ heavy chains if one assumes 2–3 molecules of heavy chain per phage and then assays for TU produce a 10-fold underestimate of the absolute number of phage. One µg of a 25 Kd light chains is $2 \times 4.10^{13}$ molecules-a 10-fold molar excess.

Clearly, many variations on this theme are possible once the principle behind it is shown to be correct. For example the positions of heavy and light chains could be reversed and the chains themselves could derive from several different sources. For example human fd heavy chains on phage could be mixed with light chains from a soluble light chain repertoire expressed in *E. coli*. Alternatively, the light chains could be purified from human serum.

The following example demonstrates not only that the principle is valid, but also that the process is surprisingly efficient.

a) Preparation of Heavy Chain Phage

VHCH1 NQ10.12.5 in fd-DOG was that constructed in example 1. VHCH1 anti-TNF in fd-DOG was used as a negative control. This clone was constructed from a murine anti-Tumour Necrosis Factor monoclonal antibody. The VH gene of this antibody was PCR amplified and linked in frame, by PCR, to the human CH1 (Cγl) domain from which the natural Apa LI site has been deleted (see example 2) and cloned as Apa LI-Not I fragments in fd-DOG. These phage were grown and concentrated as described in example 1.

b) Preparation of soluble heavy and light chain NQ10.12.5

These were prepared from the parental mouse monoclonal antibody NQ10.12.5. Culture supernatant was purified on protein A sepharose and concentrated to 20 mg/ml by Amicon ultrafiltration. This was then diluted with an equal volume of 1M Tris pH8.0 and 1/10th volume of 1M 2-mercaptoethanol added; this amount of mercaptoethanol is sufficient to reduce the interchain but not the intra-chain disulphide bonds. After 1 hour at room temperature the free thiol groups were alkaylated by addition of 1/10th volume 1.5M iodoacetamide and incubated on ice for 1 hour.

The separated chains were purified by gel-filtration on a Zorbax Biosieves GF250 TSK column (DuPont) connected to an HPLC (Gilson). Two hundred and fifty μl aliquots of the reduced mixture were run in 5M Guanidine HC1/20 mM Sodium phosphate, pH8.0 under the following conditions: Flow rate=0.5 mls/min; Fraction volume=0.25 mls; chart speed=10 mm/min; detector range=2.0 (280 nm); pressure=up to 1000 psi; run time=30 minutes.

Peak fractions were analysed by SDS-PAGE and those fractions with pure heavy and light chain used in mixing experiments.

c) Recombination of Chains

The following mixes were set up:

NQ10.12.5 Heavy chain phage+Soluble NQ10.12.5 Heavy chain

NQ10.12.5 Heavy chain phage+Soluble NQ10.12.5 Light chain

NQ10.12.5 Heavy chain phage only anti-TNF Heavy chain phage+Soluble NQ10.12.5 Heavy chain anti-TNF Heavy chain phage+Soluble NQ10.12.5 Light chain anti-TNF Heavy chain phage only In each case, $1\times10^{11}$ T.U. of phage were mixed with 25 μg, 10 g, 5 μg or 1 μg of purified soluble light chain and made to 5M Guanidine HC1/20 mM Sodium phosphate, pH 8.0 in 900 μl final volume. These samples were then placed in a Pierce Microdialyzer System 500 sealed with Visking tubing (No.2, Medicell Ltd., London N1 1LX, England). Samples were dialysed against 3 changes of 100 mM Tris-HCl, pH7.4 at 4° C. for 48 hours and used in ELISA.

The above treatment (particularly the 5M Guanidine HCl step) appears to have little or no effect on the structure of the phage particle, at least with regard to infectivity, since there is no drop in T.U. of the sample over the course of the experiment.

d) ELISA showing functionally of refolded antibodies

The efficiency of refolding was assayed by ELISA against phOX-BSA, which detects correctly refolded antibody. This ELISA was performed in the same was as described in example 1. The key observation is that functional antibody is indeed recovered when heavy chain NQ10.12.5 phage are mixed with purified NQ10.12.5 light chain. In fact, there is little difference in signal obtained over the range of light chain concentrations down to 1 μg results are shown in FIG. 12. It is evident from this that the stimulation is absolutely specific: stimulation is only seen when heavy chain anti-OX phage are mixed with anti-OX light chain—no stimulation is seen when heavy chain anti-OX phage alone or with heavy chain anti-OX phage mixed with soluble anti-OX heavy chain. Neither is any stimulation seen when anti-TNF heavy chain phage are used alone or have been mixed with anti-OX heavy or light chain. Only when the correct heavy and light combination is used is a functional antibody produced.

This experiment demonstrates that the process works surprisingly well. The light chains could derive from other sources such as from a library constructed in *E. coli* or from serum antibody. The process will also work if heavy and light chains are reversed with respect to the above, i.e. light chain on phage and soluble heavy chain.

EXAMPLE 4

Humanising rodent antibodies using polycombinatorial libraries and CDR imprinting CDR3 of the heavy chain is generally found to be the most variable of all CDRs in terms of both length and sequence, and can make important contacts with antigen (Winter, G. and Milstein C. Man-made Antibodies. (1991) Nature 349, 293–299). This is an important consideration when humanising, which can be by CDR-grafting or chain-shuffling (PCT/GB91/01134). The applicants have realised that it may be advantageous to apply the polycombinatorial approach to humanising by a chain-shuffling process in which the VHCDR3 sequence of the rodent antibody is imprinted upon the human VH segments.

In this example a mouse anti-HIV gp120 monoclonal antibody was humanised. The VH domain of this mouse antibody was fused to the human Cγ1 domain and cloned into pUC19Sfi/Not/polymyc.

A repertoire of naive human light chains cloned as g3 fusions in fd-DOG was then infected into the cells carrying the chimaeric heavy chain, and phage selected on antigen. These phage have both heavy and light chains on their surface, though the phage genome encodes just the light chain; this is not a problem since the only heavy chain is the one provided.

Light chains selected this way were then paired with a library of naive human VH domains, PCR-amplified in such a way that CDR3 of the human antibodies were replaced with that of the original mouse heavy chain.

Section a) deals with construction of a chimaeric Fab fragment in which the mouse F58 VH and VL domains are fused to human CH1 and CK sequences. This clone was used in early characterisation of the antibody and served as a template for subsequent PCR amplification of the heavy chain, which was then cloned into pUC19 Sfi-Not polymyc as a PstI-Not I fragment (section b). Section c) describes construction of a human light chain repertoire in fd-DOG, which was then infected into cells containing the chimaeric heavy chain on pUC19 (section d). The resulting phage were panned against the peptide (section e) and the selected light chains PCR-amplified and cloned as Asc I-Not I fragments alongside the chimaeric heavy chain (section f) and assayed for their ability to bind antigen by ELISA (section g). Selected light chains were recloned in pUC (section h) and naive human VH domains amplified with a mutagenic primer imposing the F58 CDR3 sequence on the domains, and the resulting fragments cloned in phage (section i). This repertoire of imprinted heavy chain phage was then used to infect cells carrying the selected light chains on pUC and the resulting phage panned on antigen. Finally, the selected heavy and light chains are cloned together on the same replicon and assayed for binding to antigen (section j).

a) Cloning of F58 Chimaeric Heavy Chain i) cDNA synthesis and primary PCR

Five ml of cultured hybridoma cells (approximately 2×106 cells) were washed in PBS, pelleted, resuspended in 200 μl 0.1% diethylpyrocarbonate in water and immediately boiled for 5 minutes. After centrifugation, 68 μl of the 'boilate' supernatant was added to a 28 μl reaction mixture resulting in a 96 μl reaction mixture containing 140 mM KCl, 50 mM Tris.HCl (pH8.1 @ 42° C.), 8 mM DTT, 500 μM deoxythymidine triphosphate, 500 μM deoxycytidine triphosphate, 500 μM deoxyadenine triphosphate and 500 μM deoxyguanine triphosphate nucleotide triphosphate (500 μM dNTPs), 160 units of human placental RNAse inhibitor and 10 pmol of forward primer. Four μl (100 units) of avian myeloblastosis virus (AMV) reverse transcriptase was added, the reaction incubated at 42° C. for 1 hour, heated to 100° C. for 3 minutes, quenched on ice and centrifugated for 5 minutes. The supernatant was then used immediately for PCR.

Separate PCR amplifications were performed for the heavy and light chains. Fifty μl reaction mixtures were prepared containing 5 μl of the supernatant from the cDNA synthesis, 250 μM dNTPs, 50 mM KCl, 100 mM Tris. HCl (pH8.3), 1.5 mM MgCl2, 175 μg/ml BSA, 20 pmol each of the appropriate mixtures of forward and back primers (Clackson, T et al. (1991) supra) and 1 μl (5 units) Thermus aquaticus (Taq) DNA polymerase (Cetus, Emeryville, Calif.). The reaction mixture was overlaid with paraffin oil and subjected to 30 cycles of amplification using a Techne PHC-2 thermal cycler. The cycle was 94° C. for 1 minute (denaturation), 55° C. for 1 minute (annealing) and 72° C. for 1 minute (extension). The product was analyzed by running 5 μl on a 2% agarose gel. The remainder was extracted twice with ether, once with phenol/chloroform, ethanol precipitated and resuspended in 50 μl of $H_2O$.

ii) Cloning and sequencing of amplified VH and Vk DNA

The amplified VH DNA was digested with PstI and BstEII, purified on a 2% low melting point agarose gel and ligated into M13VHPCR1 digested with PstI and BstEII (Orlandi, R., D. H. Gussow, P. T. Jones and G. Winter (1989). Cloning immunoglobulin variable domains for expression by the polymerase chain reaction. *Proc.Natl. Acad. Sci. USA* 86 (10), 3833–7). The amplified VK DNA was digested with PvuII and Bgl II and ligated into M13VKPCR1 digested with Pvu II and Bcl I. The ligation mixtures were used to transform competent TG1 cells. Two clones from separate amplifications were sequenced for each VH and Vk chain using the dideoxynucleotide chain termination method.

iii) Generation of an Fab construct for expression in *E. coli*

A chimaeric Fab containing the F58 variable domains and the human IgG1 CH1 and Ck domains was constructed by ligating the F58 V-domains into a vector containing the constant domains. M13VHPCR1 containing the F58 VH was digested with PstI and BstEII. The resulting F58VH fragment was then purified on a 1.5% agarose gel, isolated from the gel with Geneclean and ligated into pJM-1FabD1.3 digested with PstI and BstEII (This clone has the same constant domains and restriction sites as FabNQ10.12.5 described in example 1—in fact FabNQ10.12.5 was constructed using the constant domains pJM-1 FabD1.3. The ligation mixture was used to transform competent *E. coli* N4830-1 cells (Gottesman, M. E. Adhya, S. and Das, A. (1980) J.Mol.Biol. 140, 57–75) and clones containing the F58 VH identified by restriction analysis of RF DNA. The F58 Vk was amplified by PCR with the primers Vk2BACK and Vk3FOR2 (Clackson, T. et al (1991) supra) using M13VkPCR containing the F58 Vk as template. The PCR product was digested with SacI and XhoI, purified on a 1.5% agarose gel, isolated from the gel with Geneclean and ligated into pJM-1 Fab vector containing the F58 VH digested with SacI and XhoI. The ligation mixture was used to transform competent *E. coli* N4830-1 cells and clones containing the F58 Vk identified by restriction analysis of RF DNA.

b) PCR and Cloning of F58 Chimaeric Heavy.Chain

The F58 chimaeric heavy chain was PCR amplified from F58 Fab clone DNA, using the procedure described in example 1 and using the primers VH1BACKSFI15 and HUCH1FORASCNOT (Table 1). The resulting ca. 700 bp fragment was digested with Pst I and Not I and cloned into Pst I and Not I-cut pUC19Sfi/Not/polymyc plasmid using standard procedures (Sambrook, J. et al 1989, supra. and example 1).

c) Construction of Light Chain Repertoire

The light chain repertoire was constructed using the same materials and conditions as described in example 2, with the exception that the pullthrough was performed using the following primers:

λ chains: HUVLBAAPA (equimolar mix of 1–6) & HUCLFORSERNOT

κ chains: HUVKBAAPA (equimolar mix of 1–6) & HUCK-FORSERNOT

PCR products were digested with Apa LI and Not I using the standard format and cloned into Apa LI and Not I-cut fd-DOG as described in examples 1&2. Phage were prepared from the library clones as described in examples 1&2 and used to infect cells containing the heavy chain (see below).

d) Production of Shuffled Fab Phage

Cells containing the F58 chimaeric heavy chain were grown overnight at 38° C. in 2YTAG and 500 μl added to 50 mls fresh 2YTAmp medium, prewarmed to 37° C., in a conical flask. The cells were grown with shaking to $O.D._{600}$ of ca. 0.5 before adding a total of $10^{11}$ phage from the light chain repertoire. The culture was left at 37° C. for 45 minutes without shaking then shaken vigorously for another 45 minutes at 37° C. before adding tetracyline to 15μg/ml and shaking overnight.

Phage were harvested by PEG precipitation of the culture supernatant as previously described (examples 1&2) and used for selection experiments.

e) Panning of Shuffled Fab Phage

This was performed on maxisorb plates as previously described (Marks J. et al., 1991, supra), with the exception that the tubes were coated with env gp120 V3 loop peptide of HIV-1 isolated IIIB dissolved to 10 μg/ml in water. This peptide was obtained from the AIDS-directed program (repository ref: ADP737) and has the sequence:

C T R P N N N T R R S I R I Q R G - PGRAFVTIGKIGNMRQAHCN

The phage eluted from the tubes were used to re-infect fresh cells containing the F58 chimaeric heavy chain and the panning/re-infection procedure repeated another three times.

f) Recloning of Selected Light Chains

Selected light chains were PCR-amplified from fd-DOG light chain DNA using the procedures described in example 1 and primers G3LASCGTGBACK and HUCLFORSERNOT or HUCKFORSERNOT. The G3LASCGTGBACK primer anneals upstream of the translational start of the gIII signal in fd, and brings in an Asc I site and a ribosome binding site (RBS). These fragments were digested with Asc I and Not I and cloned into Asc I and Not I-cleaved pUC19F58 plasmid (as shown in FIGS. 13(*i*)–(*ii*)) so as to create a cistron, enabling soluble Fab to be produced. This was analysed for peptide binding in ELISA and bound antibody detected by virtue of the myc tag peptide on the end of the light chain.

g) ELISA This was performed as described below.

1. Inoculate 100 μl 2×TY, 100 μg/ml ampicillin, 1% glucose in 96-well plates ('cell wells', Nuclon) and grow with shaking (300 rpm) overnight at 37° C.
2. Use a 96-well transfer device to transfer small inocula from this plate to a second 96-well plate containing 200 μl fresh 2×TY, 100 μg/ml ampicillin, 0.1% glucose per well. Grow at 37° C., shaking until O.D.$_{600}$ is approximately 0.9 (about 3 hrs). To the wells of the original plate, add 25 μl 60% glycerol per well and store at −70° C.
3. Add 25 μl 2×TY, 100 μg/ml ampicillin, 9 mM IPTG (final concentration 1 mM IPTG). Continue shaking at 30° C. for a further 16 to 24 hrs.
4. Spin 4,000 rpm for 10 min and use 100 μl supernatant in ELISA.
5. Coat plate (Falcon 3912) with 50 μ per well of peptide at 10 μg/ml in water. Leave overnight at room temperature.
6. Rinse wells 3× with PBS, and block with 200 μl per well of 1% BSA/PBS, for 1 hr at 37° C.
7. Rinse wells 3× with PBS, then add 25 μl 6% BSA/PBS to all wells.
8. Add 100 μl culture supernatant containing soluble Fab to the appropriate wells. Mix, leave 1.5 hrs room temperature.
9. Discard test solution, and wash out wells 3 times with PBS, 0.05% Tween 20 and 3 times with PBS. Pipette 100 μl of 4 μg/ml purified 9E10 antibody, in 2% Marvel/PBS, into each well. Incubate at room temperature for 1.5 hrs.
10. Discard 9E10 antibody, and wash out wells 3 times with PBS, 0.05% Tween 20 and 3 times with PBS. Pipette 100 μl of 1:500 dilution of anti-mouse antibody (peroxidase-conjugated anti-mouse immunoglobulins, Dakopats/ICN, or peroxidase conjugated anti-mouse IgG, Fc-specific, Sigma A-2554). Incubate at room temperature for 1.5 hrs.
11. Discard 2nd antibody, and wash wells 3 times with PBS, 0.05% Tween 20 and 3 times with PBS.
12. Add one 10 mg ABTS (2.2'-azino bis(3-ethylbenzthiazoline-6-sulphonic acid), diammonium salt) tablet to 20 ml 50 mM citrate buffer, pH4.5. (50 mM citrate buffer, pH4.5 is made by mixing equal volumes 50 mM trisodium citrate and 50 mM citric acid).
13. Add 2 μl 30% hydrogen peroxide to the above solution immediately before dispensing.
14. Add 100 μl of the above solution to each well. Leave at room temperature 20–30 mins.
15. Quench by adding 50 μl 3.2 mg/ml sodium fluoride. Read at 405 nm.

Note 1: Alternatively, inoculate clones from transformation plate into 100 μl 2×TY, 100 μg/ml ampicillin, 0.1% glucose in 96-well plates ('cell wells', Nuclon) and grow with shaking (300 rpm) 37° C., shaking until O.D.$_{600\ nm}$ is approximately 0.9 (about 6 hrs). Continue with step 3.

Note 2: This method is based on that of DeBellis D. and Schwartz I., 1990 *Nucl. Acids Res.* 18: 1311 and relies on the low levels of glucose present in the starting medium being metabolised by the time the inducer (IPTG) is added.

Note 3: 'Marvel' is dried milk powder. PBS is 5.84 g NaCl, 4.72 g Na$_2$HPO$_4$ and 2.64 g NaH$_2$PO$_4$.2H$_2$O, pH7.2, in 1 litre. BSA is Bovine Serum Albumin.

h) Subcloning Selected Light Chains

Light chains were PCR-amplified from DNA of selected clones using an equimolar mix of the 7 HUVLBASFI primers in conjunction with HUCLFORSERASCNOT or an equimolar mix of the 6 HUVKBASFI primers in conjunction with HUCKFORSERASCNOT as described in example 2. PCR fragments were cut with Sfi I and Not I and cloned into Sfi I and Not I-cut pUC19Sfi/Not/polymyc then transformed into TG1.

The panning/infection process described above is essentially repeated again, this time with the positions of the heavy and light chains reversed.

i) CDR-imprinting VH

VH domains were amplified from the pooled primary PCR material described in example 2. Six separate pullthrough reactions were performed with the mutagenic F58GRAFTJH4SAL primer and each of the HUVH-BAAPA1–6 primers individually. Conditions for the pullthrough were the same as in example 2(d) except that the annealing temperature was lowered to 45° C.

The resulting VH fragments were pooled and cut with Apa LI and Sal I using standard conditions and cloned into Apa LI and Xho I-cut fd-DOG-G1CH1 using standard protocols (Sal 1 and Xho I produce compatible CTAG overhangs). Phage were prepared from this library as described above, this time using the heavy chain phage to infect cells carrying the selected light chains expressed in pUC19Sfi/Not/polymyc.

j) Screening of Final Heavy-Light Combinations

The end result of this process is a pool of selected heavy chains and a pool of selected light chains. These are now combined at random. Heavy chain clones are now PCR-amplified using an equimolar mix of all 6 HUVHBACKSFI primers in conjunction HUCHLFORASCNOT using the procedure described in example 1. These fragments are cut with Sfi I and Asc I and gel-purified using standard procedures (Example 1), then ligated to equimolar quantities of Asc I-Not I-cut light chains produced in step f) above and Sfi I and Not I-cut pUC19Sfi/Not/polymyc vector, also produced earlier. Alternatively, these Sfi I-Asc I fragments replaced the F58 heavy chain in the constructs shown at the end of FIG. 13 (*i*). These constructs were then transformed into TG1 and analysed for peptide binding activity by ELISA as described above.

The end-products are completely human Fab fragments with the same or similar antigen-specificity as the parent rodent antibody.

EXAMPLE 5

Display of Single Chain Fv and Fab Fragments Derived from the Anti-Oxazolone Antibody NO10.12.5 on Bacteriophage fd using pHEN1 and fdCAT2

Figure 18:
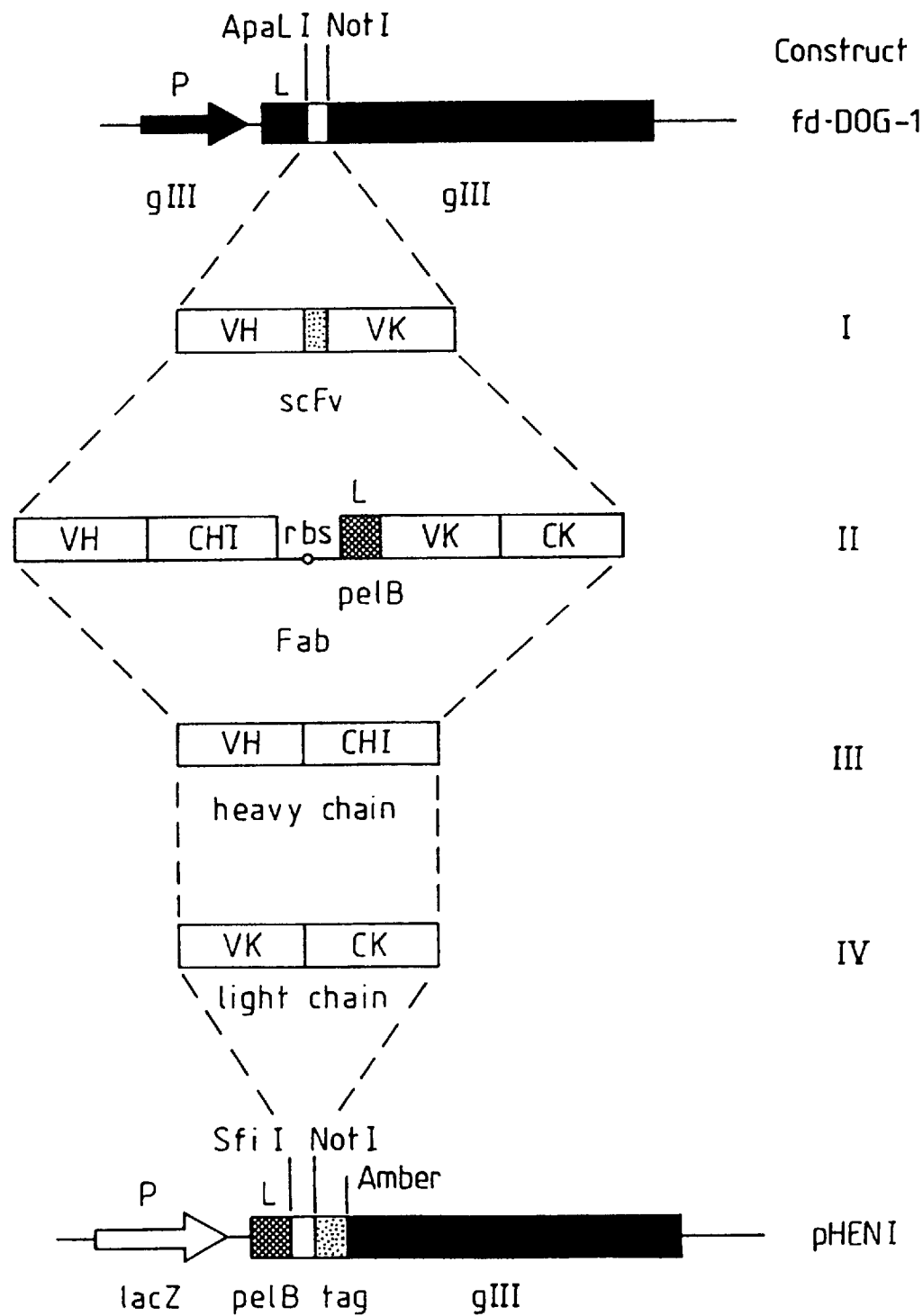
FIG. 18. The antibody constructs cloned into fd-DOG1 and pHEN1 for display on the surface of phage. Constructs I, II, III and IV were cloned into both fd-DOG1 (as ApaLI-NotI fragments) and pHEN1 (as SfiI-NotI fragments) and pHEN1 (as SfiI-NotI fragments). All the constructs contained the heavy chain (VH) and light chain (VK) variable regions of the mouse anti-phOx antibody NQ10.12.5. The constant domains were human CK and CH1 ($\gamma$1 isotype).

A range of constructs (see FIG. 18) were made from a clone (essentially construct II in pUC19) designed for expression in bacteria of a soluble Fab fragment (Better et al. 1988 see above) from the mouse anti-phOx (2-phenyl-5-oxazolone) antibody NQ10.12.5 (Griffiths, G. M. et al. Nature 312, 271–275, 1984). In construct II, the V-regions are derived from NQ10.12.5 and attached to human Ck and CH1 (1 isotype) constant domains. The C-terminal cysteine residues, which normally form a covalent link between light and heavy antibody chains, have been deleted from both the constant domains. To clone heavy and light chain genes together as Fab fragments (construct II) or as separate chains (constructs III and IV) for phage display, DNA was amplified from construct II by PCR to introduce a NotI restriction site at the 3' end, and at the 5' end either an ApaLI site (for cloning into fd-CAT2) or SfiI sie (for cloning into pHEN1). The primers FABNOTFOK with VHLBACKAPA (or VH1BACKSFI15) were used for PCR amplification of genes encoding Fab fragments (construct II), the primers FAB-NOTFOH with VH1BACKAPA (or VH1BACKSFI15) for heavy chains (construct III), and the primers FABNOTFOK and MVKBAAPA (or MVKBASFI) for light chains (construct IV).

The single-chain Fv version of NQ10.12.5 (construct I) has the heavy (VH) and light chain (Vk) variable domains joined by a flexible linker (Gly$_4$Ser)$_3$ (Huston, J. S. et al. Proc. Natl. Acad. Sci. USA 85 5879–5883, 1988) and was constructed from construct II by 'splicing by overlap extension' as in example 14 of WO 92/01047. The assembled genes were reamplified with primers VK3F2NOT and VH1BACKAPA (or VH1BACKSFI15) to append restriction sites for cloning into fd-CAT2 (ApaLI-NotI) or pHEN1 (SfiI-NotI).

VH1BACKAPA,5'-CAT GAC CAC A<u>GT GCA C</u>AG GT(C/G) (A/C)A(A/G) CTG CAG (C/G)AG TC(A/T) GG;

VH1BACKSFI15,5'-CAT GCC ATG ACT CGC <u>GGC CCA GCC GGCC</u>AT GGC C(C/G)A GGT (C/G) (A/C)A (A/G)CT GCA G(C/G)A GTC (A/T)GG;

FABNOTFOH,5'-CCA CGA TTC <u>TGC GGC CGC</u> TGA AGA TTT GGG CTC AAC TTT CTT GTC GAC;

FABNOTFOK,5'-CCA CGA TTC <u>TGC GGC CGC</u> TGA CTC TCC GCG GTT GAA GCT CTT TGT GAC;

MVKBAAPA,5'-CAC <u>AGT GCA C</u>TC GAC ATT GAG CTC ACC CAG TCT CCA;

MVKBASFI,5'-CAT GAC CAC GC <u>G GCC CAG CCG GCC</u> ATG GCC GAC ATT GAG CTC ACC CAG TCT CCA;

VK3F2NOT,5'-TTC <u>TGC GGC CGC</u> CCG TTT CAG CTC GAG CTT GGT CCC.

Restriction sites are underlined.

Rescue of Phage and Phagemid particles

Constructs I–IV (FIG. 15) were introduced into both fd-CAT2 and pHEN1. Phage fd-CAT2 (and fd-CAT2-I,II,III or IV) was taken from the supernatant of infected *E. coli* TG1 after shaking at 37° C. overnight in 2×TY medium with 12.5 μg/ml tetracycline, and used directly in ELISA. Phagemid pHEN1 (and pHEN1-I and II) in *E. coli* TG1 (supE) were grown overnight in 2 ml 2×TY medium, 100 μg/ml ampicillin, and 1% glucose (without glucose, expression of g3p prevents later superinfection by helper phage). 10 μl of the overnight culture was used to innoculate 2 ml of 2×TY medium, 100 μg/ml ampicillin, 1% glucose, and shaken at 37° C. for 1 hour. The cells were washed and resuspended in 2×TY, 100 μg/ml ampicillin, and a phagemid particles rescued by adding 2 μl (10$^8$pfu) VCSM13 helper phage (Stratagene). After growth for one hour, 4 μl kanamycin (25 mg/ml) was added, and the culture grown overnight. The phagemid particles were concentrated 10-fold for ELISA by precipitation with polyethylene glycol.

ELISA

Detection of phage binding to 2-phenyl-5-oxazolone (phOx) was performed as in example 9. 96-well plates were coated with 10 μg/ml phOx-BSA or 10 μg/ml BSA in PBS overnight at room temperature, and blocked with PBSS containing 2% skimmed milk powder. Phage (mid) supernatant (50 μl) mixed with 50 μl PBS containing 4% skimmed milk powder was added to the wells and assayed. To detect binding of soluble scfv or Fab fragments secreted from pHEN1, the c-myc peptide tag described by Munro and Pelham 1986 supra, was detected using the anti-myc monoclonal 9E10 (Evan, G. I. et al. Mol Cell Biol 5 3610–3616, 1985) followed by detection with peroxidase-conjugated goat anti-mouse immonoglobulin. Other details are as in example 9.

The constructs in fdDOG1 and pHEN1 display antibody fragments of the surface of filamentous phage. The phage vector, fd-DOG1 (FIG. 16) is based on the vector fd-tet (Zacher, A. N. et al. Gene 9 127–140, 1980) and has restriction sites (ApaLI and NotI) for cloning antibody genes (or other protein) genes for expression as fusions to the N-terminus of the phage coat protein g3p. Transcription of the antibody-g3p fusions in fd-DOG1 is driven from the gene III promoter and the fusion protein targetted to the periplasm by means of the g3p leader. Fab and scFv fragments of NQ10.12.5 cloned into fd-DOG1 for display were shown to bind to phOx-BSA (but not BSA) by ELISA (table 2). Phage were considered to be binding if A$_{405}$ of the sample was at least 10-fold greater that the background in ELISA.

Figures 17A, 17B:
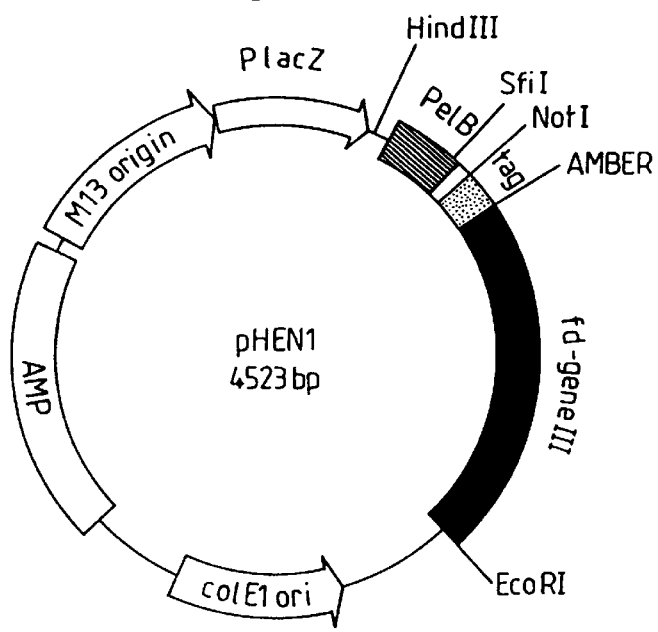
FIGS. 17(a)–17(b) show the phagemid pHEN1 a derivative of pUC119 described in example 24; and b) the cloning sites in the phagemid PHEN.

The phagemid vector, pHEN1 (FIG. 17(a)), is based upon pUC119 and contains restriction sites (SfiI and NotI) for cloning the fusion proteins. Here the transcription of antibody-g3p fusions is driven from the inducible lacZ promoter and the fusion protein targetted to the periplasm by means of the pelB leader. Phagemid was rescued with VCSM13 helper phage in 2×TY medium containing no glucose or IPTG: under these conditions there is sufficient expression of antibody-g3p. Fab and scFv fragments of NQ10.12.5 cloned into pHEN1 for display were shown to bind to phOx-BSA (but not BSA) by ELISA (Table 2) using the same criterion as above.

An alternative methodology for preparing libraries of Fab fragments expressed on the surface of phage would be to:
1. Prepare a library of phage expressing heavy chain (VHCH) genes from inserts in the phage genome.
2. Prepare a library of light chain genes in a plasmid expression vector in *E. coli*, preferably a phagemid, and isolate the soluble protein light chins expressed from this library.
3. Bind the soluble protein light chains from the library to the heavy chain library displayed on phage.
4. Select phage with the desired properties of affinity and specificity.

These will encode the heavy chain (VHCH) genes.
5. Isolate the light chain genes encoding light chains which form suitable antigen binding sites in combination with the selected heavy chains, preferably by using superinfection of bacteria, containing phagemid expressing the light chain, with phage expressing the selected heavy chain and then assaying for antigen binding.

EXAMPLE 6

Rescue of Phagemid Encoding a Gene III Protein Fusion with Antibody Heavy or Light Chains by Phage Encoding the Complementary Antibody Chain Displayed on Phage and the Use of this Technique to Make Dual Combinatorial Libraries With random combinatorial libraries there is a limitation on the potential diversity of displayed Fab fragments due to the transformation efficiency of bacterial cells. Described here is a strategy (dual combinatorial libraries) to overcome this problem, potentially increasing the number of phage surveyed by a factor of 10$^7$.

For assembly of heavy and light chains expresses from different vectors, phagemid (pHEN1-III or IV) was grown in *E. coli* HB2151 (a non-supressor strain) to allow production of soluble chains, and rescued as above except that helper phage were used expressing partner chains as fusions to g3p (10$^9$ TU fd-DOG1-IV or III respectively) and 2 μl tetracycline (12.5 mg/ml) in place of kanamycin.

Separate Vectors to Encode Fab Heavy and Light Chains

The heavy and light chains of Fab fragments can be encoded together in the same vector or in different vectors. To demonstrate this the heavy chain (construct III) was cloned into pHEN1 (to provide soluble fragments) and the light chain (construct IV) into fd-DOG1 (to make the fusion with g3p). The phagemid pHEN1-III, grown in *E. coli* H2151 (non-supressor) was rescued with fd-DOG1-IV phage, and phage(mid) shown to bind to phOx:BSA, but not to BSA (Table 2). This demonstrates that soluble light chain is correctly associating with the heavy chain anchored to the g3p, since neither heavy chain nor light chain alone bind antigen (Table 2).

Similar results were obtained in the reverse experiment (with phagemid pHEN-1-IV and fd-CAT2-III phage) in which the heavy chain was produced as a soluble molecule and the light chain anchored to g3p (Table 2). Hence a Fab fragment is assembled on the surface of phage by fusion of either heavy or light chain to g3p, provided the other chain is secreted using the same or another vector (FIG. 19).

The resulting phage population is a mixture of phage abd rescued phagemid. The ratio of the two types of particle was assessed by infecting log phase *E. coli* TG1 and plating on TYE plates with either 15 μg/ml tetracycline (to select for fd-DOG1) or 100 μg/ml ampicillin (to select for pHEN1). The titre of fd-DOG1 phage was $5 \times 10^{11}$ TU/ml and the titre of pHEN1 $2 \times 10^{10}$ TU/ml, indicating a packaging ratio of 25 phage per phagemid.

Demonstrated here is an alternative strategy involving display of the heterodimeric antibody Fab fragments on the surface of phage. One of the chains is fused to g3p and the other is secreted in soluble form into the periplasmic space of the *E. coli* where it associates non-covalently with the g3p fusion, and binds specifically to antigen. Either the light or heavy chain can be fused to the g3p: they are displayed on the phage as Fab fragments and bind antigen (FIG. 19). Described are both phage and phagemid vectors for surface display. Phagemids are probably superior to phage vectors for creation of large phage display libraries. Particularly in view of their higher transfection efficiencies (two to three orders of magnitude higher), allowing larger libraries to be constructed. The phagemid vector, pHEN1 also allows the expression of soluble Fab fragments in non-suppressor *E. coli*.

Also demonstrated here is that heavy and light chains encoded on the same vector (construct II), or on different vectors (constructs III and IV) can be displayed as Fab fragments. This offers two distinct ways of making random combinatorial libraries for display. Libraries of heavy and light chain genes, amplified by PCR, could be randomly linked by a 'PCR assembly' process (example 14 of WO 92/01047) based on 'splicing by overlap extension', cloned into phage(mid) display vectors and expressed from the same promoter as part of the same transcript (construct II) as above, or indeed from different promoters as separate transcripts. Here the phage(mid) vector encodes and displays both chains. For a combinatorial library of $10^7$ heavy chains and $10^7$ light chains, the potential diversity of displayed Fab fragments ($10^{14}$) is limited by the transfection efficiency of bacterial cells by the vector (about $10^9$ clones per μg cut and ligated plasmid at best) (W. J. Dower et al Nucl. Acids. Res. 16 6127–6145, 1988). Libraries thus prepared are analogous to the random combinatorial library method described by Huse, W. D. et al Science 246 1275–1281 (1989), but have the important additional feature that display on the surface of phage gives a powerful method of selecting antibody specificities from the large number of clones generated.

Alternatively, libraries of heavy and light chains could be cloned into different vectors for expression in the same cell, with a phage vector encoding the g3p fusion and a phagemid encoding the soluble chain. The phage acts as a helper, and the infected bacteria produced both packaged phage and phagemid. Each phage or phagemid displays both chains but encodes only one chain and thus only the genetic information for half of the antigen-binding site. However, the genes for both antibody chains can be recovered separately by plating on the selective medium, suggesting a means by which mutually complementary pairs of antigen binding heavy and light chain combinations could be selected from random combinatorial libraries. For example, a light chain repertoire on fd phage could be used to infect cells harbouring a library of soluble heavy chains on the phagemid. The affinity purified phagemid library could then be used to infect *E. coli*, rescued with the affinity purified phage library, and the new combinatorial library subjected to a further round of selection. Thus, antibody heavy and light chain genes are reshuffled after each round of purification. Finally, after several rounds, infected bacteria could be plated and screened individually for antigen-binding phage. Such 'dual' combinatorial libraries are potentially more diverse than those encoded on a single vector. By combining separate libraries of $10^7$ light chain phage(mid)s, the diversity of displayed Fab fragments (potentially $10^{14}$) is limited only by the number of bacteria ($10^{12}$ per litre). More simply, the use of two vectors should also facilitate the construction of 'hierarchical' libraries, in which a fixed heavy or light chain is paired with a library or partners, offering a means of 'fine-tuning' antibody affinity and specificity.

TABLE 1

Oligonucleotide primers used for PCR of human immunoglobulin genes
ALL PRIMERS WRITTEN 5'→3'

A) General Fab primers

| | |
|---|---|
| VH1BACKAPA, | 5'-CAT GAC CAC <u>AGT GCA C</u>AG GT(C/G) (A/C)A(A/G) CTG CAG (C/G)AG TC(A/T) GG; |
| VH1BACKSFI15, | 5'-CAT GCC ATG ACT CGC <u>GGC CCA GCC GGC</u> CAT GGC C(C/G)A GGT (C/G) (A/C)A (A/G)CT GCA G(C/G)A GTC (A/T)GG |
| FABNOTFOH, | 5'-CCA CGA TTC T<u>GC GGC CGC</u> TGA AGA TTT GGG CTC AAC TTT CTT GTC GAC; |
| FABNOTFOK, | 5'-CCA CGA TTC T<u>GC GGC CGC</u> TGA CTC TCC GCG GTT GAA GCT CTT TGT GAC; |
| MVKBAAPA | 5'-CAC <u>AGT GCA C</u>TC GAC ATT GAG CTC ACC CAG TCT CCA; |
| MVKBASFI, | 5'-CAT GAC CAC GC<u>G GCC CAG CCG GCC</u> ATG GCC GAC ATT GAG CTC ACC CAG TCT CCA; |

Restriction sites are underlined.

B) Primers for manipulating human CH1 domain

| | |
|---|---|
| APAOUTBACK | GAC CAG CGG CGT CCA CAC CTT CCC GGC T |
| APAOUTFOR | AGC CGG GAA GGT GTG GAC GCC GCT GGT C |
| RJHXHOBACK | CAC CAC GGT CAC CGT CTC GAG TGC CTC CAC CAA GGG CCC ATC |

TABLE 1-continued

Oligonucleotide primers used for PCR of human immunoglobulin genes
ALL PRIMERS WRITTEN 5'→3'

| | |
|---|---|
| FDGAM1BAAPA | CAT GAC CAC AGT GCA CAG GTG CAG CTG CAG GTC GAC |
| FDSEQ | GAA TTT TCT GTA TGA GG |
| HUG1CYSASCNOTFOR | GAG TCA TTC TCG ACT TGC GGC CGC CTG CTA TTA TCG GGC GCG CCT TTA TTA ACA AGA TTT GGG CTC AAC TTT C |

C) Primers for first strand cDNA synthesis

Human IgM Constant Region Primer
    HuIgMFOR   5'-TGG AAG AGG CAC GTT CTT TTC TTT-3'
Human κ Constant Region Primer
    HuCκFOR   5'-AGA CTC TCC CCT GTT GAA GCT CTT-3'
Human λ Constant Region Primer
    HuCλFOR   5'-TGA AGA TTC TGT AGG GGC CAC TGT CTT-3'

C) Heavy chain PCL primers

Human VH Back Primers

HuVH1aBACK  5'-CAG GTG CAG CTG GTG CAG TCT GG-3'
    HuVH2aBACK  5'-CAG GTC AAC TTA AGG GAG TCT GG-3'
    HuVH3aBACK  5'-GAG GTG CAG CTG GTG GAG TCT GG-3'
    HuVH4aBACK  5'-CAG GTG CAG CTG CAG GAG TCG GG-3'
    HuVH5aBACK  5'-GAG GTG CAG CTG TTG CAG TCT GC-3'
    HuVH6aBACK  5'-CAG GTA CAG CTG CAG CAG TCA GG-3'

Human JH Forward Primers

HuJH1–2FOR   5'-TGA GGA GAC GGT GAC CAG GGT GCC-3'
    HuJH3FOR     5'-TGA AGA GAC GGT GAC CAT TGT CCC-3'
    HUJH4–5FOR  5'-TGA GGA GAC GGT GAC CAG GGT TCC-3'
    HuJH6FOR     5'-TGA GGA GAC GGT GAC CGT GGT CCC-3'

VH BACK PRIMERS WITH APA LI SITES.

| | |
|---|---|
| HUVH1BAAPA | CAT GAC CAC AGT GCA CAG GTG CAG CTG GTG CAG TCT GG |
| HUVH2BAAPA | CAT GAC CAC AGT GCA CAG GTC AAC TTA AGG GAG TCT GG |
| HUVH3BAAPA | CAT GAC CAC AGT GCA CAG GTG CAG CTG GTG GAG TCT GG |
| HUVH4BAAPA | CAT GAC CAC AGT GCA CAG GTG CAG CTG CAG GAG TCG GG |
| HUVH5BAAPA | CAT GAC CAC AGT GCA CAG GTG CAG CTG TTG CAG TCT GC |
| HUVH6BAAPA | CAT GAC CAC AGT GCA CAG GTA CAG CTG CAG CAG TCA GG |

JHSAL primers

| | |
|---|---|
| HUJH1–2FORSAL | GAG TCA TTC TCG TGT CGA CAC GGT GAC CAG GGT GCC |
| HUJH3FORSAL | GAG TCA TTC TCG TGT CGA CAC GGT GAC CAT TGT CCC |
| HUJH4–5FORSAL | GAG TCA TTC TCG TGT CGA CAC GGT GAC CAG GGT TCC |
| HUJH6FORSAL | GAG TCA TTC TCG TGT CGA CAC GGT GAC CGT GGT CCC |

D) Light chain PCL primers

LAMBDA BACK PRIMERS WITH SFI SITES

| | |
|---|---|
| HUVL1BASFI: | GTC CTC GCA ACT GCG GCC CAG CCG GCC ATG GCC CAG TCT GTG TTG ACG CAG CCC CC |
| HUVL2BASFI: | GTC CTC GCA ACT GCG GCC CAG CCG GCC ATG GCC CAG TCT GCC CTG ACT CAG CCT GC |
| HUVL3aBASFI: | GTC CTC GCA ACT GCG GCC CAG CCG GCC ATG GCC TCC TAT GTG CTG ACT CAG CCA CC |
| HUVL3bBASFI: | GTC CTC GCA ACT CGC GCC CAG CCG GCC ATG GCC TCT TCT GAG CTG ACT CAG GAC CC |
| HUVL4BASFI: | GTC CTC GCA ACT GCG GCC CAG CCG GCC ATG GCC CAG GTT ATA CTG ACT CAA CCG CC |
| HUVL5BASFI: | GTC CTC GCA ACT GCG GCC CAG CCG GCC ATG GCC CAG GCT GTG CTC ACT CAG CCG TC |
| HUVL6BASFI: | GTC CTC GCA ACT GCG GCC CAG CCG GCC ATG GCC AAT TTT ATG CTG ACT CAG CCC CA |

KAPPA BACK PRIMERS WITH SFI SITES

| | |
|---|---|
| HUVK1BASFI: | GTC CTC GCA ACT GCG GCC CAG CCG GCC ATG GCC GAC ATC CAG ATG ACC CAG TCT CC |
| HUVK2BASFI: | GTC CTC GCA ACT GCG GCC CAG CCG GCC ATG GCC GAT GTT GTG ATG ACT CAG TCT CC |
| HUVK3BASFI: | GTC CTC GCA ACT GCG GCC CAG CCG GCC ATG GCC GAA ATT GTG TTG ACG CAG TCT CC |
| HUVK4BASFI: | GTC CTC GCA ACT GCG GCC CAG CCG GCC ATG GCC GAC ATC GTG ATG ACC CAG TCT CC |
| HUVK5BASFI: | GTC CTC GCA ACT GCG GCC CAG CCG GCC ATG GCC GAA ACG ACA CTC ACG CAG TCT CC |
| HUVK6BASFI: | GTC CTC GCA ACT GCG GCC CAG CCG GCC ATG GCC GAA ATT GTG CTG ACT CAG TCT CC |

FOREWARD PRIMERS

| | |
|---|---|
| HUCLFORSERASCNOT | GAG TCA TTC TCG ACT TGC GGC CGC CTG CTA TTA TCG GGC GCG CCT TTA TTA TGA AGA TTC TGT AGG GGC CAC TGT CTT |
| HUCKFORSERASCNOT | GAG TCA TTC TCG ACT TGC GGC CGC CTG CTA TTA TCG GGC GCG CCT TTA TTA AGA CTC TCC CCT GTT GAA GCT CTT |
| HUCKFORSER | AGA CTC TCC CCT TTT GAA GCT CTT |
| HUCLFORSER | TGA AGA TTC TGT AGG GGC CAC TGT CTT |
| HUCKFORSERNOT | GAG TCA TTC TCG ACT TGC GGC CGC AGA CTC TCC CCT GTT GAA GCT CTT |
| HUCLFORSERNOT | GAG TCA TTC TCG ACT TGC GGC CGC TGA AGA TTC TGT AGG GGC CAC TGT CTT |

TABLE 1-continued

Oligonucleotide primers used for PCR of human immunoglobulin genes
ALL PRIMERS WRITTEN 5'→3'

Human Vk Back Primers

| | | |
|---|---|---|
| HuVk1aBACK | 5'-GAC ATC CAG ATG ACC CAG TCT CC-3' | |
| HuVk2aBACK | 5'-GAT GTT GTG ATG ACT CAG TCT CC-3' | |
| HuVk3aBACK | 5'-GAA ATT GTG TTG ACG CAG TCT CC-3' | |
| HuVk4aBACK | 5'-GAC ATC GTG ATG ACC CAG TCT CC-3' | |
| HuVk5aBACK | 5'-GAA ACG ACA CTC ACG CAG TCT CC-3' | |
| HuVk6aBACK | 5'-GAA ATT GTG CTG ACT CAG TCT CC-3' | |

Human λ Back primers

| | | |
|---|---|---|
| Huλ1BACK | 5'-CAG TCT GTG TTG ACG CAG CCG CC-3' | |
| Huλ2BACK | 5'-CAG TCT GCC CTG ACT CAG CCT GC-3' | |
| Huλ3aBACK | 5'-TCC TAT GTG CTG ACT CAG CCA CC-3' | |
| Huλ3bBACK | 5'-TCT TCT GAG CTG ACT CAG GAC CC-3' | |
| Huλ4BACK | 5'-CAC GTT ATA CTG ACT CAA CCG CC-3' | |
| Huλ5BACK | 5'-CAG GCT GTG CTC ACT CAG CCG TC-3' | |
| Huλ6BACK | 5'-AAT TTT ATG CTG ACT CAG CCC CA-3' | |

E) PCL/CDR-grafting primers

| | |
|---|---|
| G3LASCGTGBACK | GTC CTC GCA ACT CCG GCG CCA CAA TTT CAC AGT AAG GAG GTT TAA CTT GTG AAA AAA TTA TTA TTC GCA ATT |
| HUCH1FORASCNOT TTT | GAG TCA TTC TCG ACT TGC GGC CGC CTG CTA TTA TCG GGC GCG CCT TTA TTA AGA AGA GGG CTC AAC TTT C |
| F58GRAFTJH4SAL GTC | GGA TGC ACT TGT CGA CAC GGT GAC CAG GGT ACC TTG GCC CCA GTA GTC AAA GTA GTA CTC TTC GTA ATC ATA GTA GAT CAG GTC ACA GTA ATA CAC GGC CGT GTC |

LAMBDA BACK PRIMERS WITH APA LI SITES

| | |
|---|---|
| HUVL1BAAPA: | TGA GCA CAC AGT GCA CTC CAG TCT GTG TTG ACG CAG CCG CC |
| HULV2BAAPA: | TGA GCA CAC AGT GCA CTC CAG TCT GCC CTG ACT CAG CCT GC |
| HUVL3aBAAPA: | TGA GCA CAC AGT GCA CTC TCC TAT GTG CTG ACT CAG CCA CC |
| HUVL3bBAAPA: | TGA GCA CAC AGT GCA CTC TCT TCT GAG CTG ACT CAG GAC CC |
| HUVL4BAAPA: | TGA GCA CAC AGT GCA CTC GAC GTT ATA CTG ACT CAA CCG CC |
| HUVL5BAAPA: | TGA GCA CAC AGT GCA CTC CAG GCT GTG CTC ACT CAG CCG TC |
| HUVL6BAAPA: | TGA GCA CAC AGT GCA CTC AAT TTT ATG CTG ACT CAG CCC CA |

KAPPA BACK PRIMERS WITH APA LI SITES

| | |
|---|---|
| HUVK1BAAPA: | TGA GCA CAC AGT GCA CTC GAC ATC CAG ATG ACC CAG TCT CC |
| HUVK2BAAPA: | TGA GCA CAC AGT GCA CTC GAT GTT GTG ATG ACT CAG TCT CC |
| HUVK3BAAPA: | TGA GCA CAC AGT GCA CTC GAA ATT GTG TTG ACG CAG TCT CC |
| HUVK4BAAPA: | TGA GCA CAC AGT GCA CTC GAC ATC GTG ATG ACC CAG TCT CC |
| HUVK5BAAPA: | TGA GCA CAC AGT GCA CTC GAA ACG ACA CTC ACG CAG TCT CC |
| HUVK6BAAPA: | TGA GCA CAC AGT GCA CTC GAA ATT GTG CTG ACT CAG TCT CC |

Human VH Back Primers

| | |
|---|---|
| HuVH1aBACKSfi | 5'-GTC CTC GCA ACT GCG GCC CAG CCG GCC ATG GCC CAG GTG CAG CTG GTG CAG TCT GG- |
| HuVH2aBACKSfi | 5'-GTC CTC GCA ACT GCG GCC CAG CCG GCC ATG GCC CAG GTC AAC TTA AGG GAG TCT GG- |
| HuVH3aBACKSfi | 5'-GTC CTC GCA ACT GCG GCC CAG CCG GCC ATG GCC GAG GTG CAG CTG GTG GAG TCT GG- |
| HuVH4aBACKSfi | 5'-GTC CTC GCA ACT GCG GCC CAG CCG GCC ATG GCC CAG GTG CAG CTG CAG GAG TCG GG- |
| HuVH5aBACKSfi | 5'-GTC CTC GCA ACT GCG GCC CAG CCG GCC ATG GCC GAG GTG CAG CTG TTG CAG TCT GC- |
| HuVH6aBACKSfi | 5'-GTC CTC GCA ACT GCG GCC CAG CCG GCC ATG GCC CAG GTA CAG CTG CAG CAG TCA GG- |

TABLE 2

| | Phase/Phagemid† | Helper phage | Binding to phOx* | Chain(s) displayed# | Chain as gene III fusion# | Soluble chain(s)# |
|---|---|---|---|---|---|---|
| A | fd-CAT2 | | non binding | none | | |
| | fd-CAT2-I | | binding | scFv | scFv | |
| | fd-CAT2-II | | binding | Fab | light chain | heavy chain |
| | pHENI | VCSM13 | non binding | none | | |
| | pHENI-I | VCSM13 | binding | scFv | scFv | |
| | pHENI-II | VCSM13 | binding | Fab | light chain | heavy chain |
| B | pHENI-I (HB2151) | | binding | | | scFv§ |
| | pHENI-II (HB2151) | | binding | | | Fab§ |
| C | fd-CAT2-III | | non binding | heavy chain | heavy chain | |
| | fd-CAT2-IV | | non binding | light chain | light chain | |
| | pHENI-III (HB2151) | VCSM13 | non binding | none | | heavy chain |
| | pHENI-III (HB2151) | fd-tet-DOGI-IV | binding | Fab | light chain | heavy chain |

TABLE 2-continued

| Phase/Phagemid† | Helper phage | Binding to phOx* | Chain(s) displayed# | Chain as gene III fusion# | Soluble chain(s)# |
|---|---|---|---|---|---|
| pHENI-IV (HB2151) | VCSM13 | non binding | none | | light chain |
| pHENI-IV (HB2151) | fd-tet-DOGI-III | binding | Fab | heavy chain | light chain |

Overview of phOx-BSA ELISA results of phage and phagemid constructions.
*Phage were considered to be 'binding' if $OD_{405}$ of sample was at least 10-fold greater than background in ELISA;
†E. coli TG1 was used for the growth of the phage unless the use of E. coli HB2151 is specifically indicated;
Information deduced from genetic structure and in accordance with binding data;
§Result confirmed experimentally by Western bolt

We claim:

1. A method of producing specific binding pair (sbp) members comprising:
   (a) a first polypeptide chain comprising an antibody heavy chain variable domain and a second polypeptide chain comprising an antibody light chain variable domain, or
   (b) a first polypeptide chain comprising an antibody light chain variable domain and a second polypeptide chain comprising an antibody heavy chain variable domain;
   which method comprises introducing into host cells
   (i) first vectors comprising nucleic acid encoding a genetically diverse population of said first polypeptide chain fused to a component of a secreted replicable genetic display package (rgdp) for display of said first polypeptide chains at the surface of rgdps, and
   (ii) second vectors comprising nucleic acid encoding a genetically diverse population of said second polypeptide chain;
   said first vectors being packaged in infectious rdgps and said introducing of said first vectors into host cells being by infection into host cells harboring said second vectors, or
   said second vectors being packaged in infectious rgdps and said introducing of said second vectors into host cells being by infection into host cells harboring said first vectors; and
   expressing said first and second polypeptide chains within the host cells to form a library of said sbp members displayed by rgdps, at least one of said population being expressed from nucleic acid that is packaged using rgdp component, whereby each said rgdp contains genetic material which encodes a polypeptide chain of the sbp member displayed at its surface.

2. A method according to claim 1 wherein at least one of said populations is expressed from a phage vector.

3. A method according to claim 1 wherein at least one of said populations is expressed from a phagemid vector, the method including using a helper phage or a plasmid expressing complementing phage genes, to help package said phagemid genome, and said component of the rgdp is a capsid protein therefore.

4. A kit for use in carrying out a method according to claim 1, said kit having the following components in addition to components required for carrying out the method:
   (i) a vector having the following features: (a) an origin of replication for single-stranded bacteriophage, (b) a restriction site for insertion of nucleic acid encoding or a polypeptide component of an sbp member, (c) said restriction site being in the 5' end region of the mature coding sequence of a phage capsid protein, and (d) with a secretory leader sequence upstream of said site which directs a fusion of the capsid protein and sbp polypeptide to the periplasmic space of a bacterial host; and (ii) another vector, having some or all of the features (a), (b), (c) and (d) of the vector described in (i).

5. A method according to claim 1 wherein each said first and second polypeptide chain is expressed from nucleic acid which is packaged as a rgdp using said component fusion product, whereby encoding nucleic acid for both said first and second polypeptide chains is packaged in respective rgdps.

6. A method according to claim 1 which comprises introducing vectors encoding a population of said first polypeptide chains into host organisms which express a population of said second polypeptide chains in free form, or introducing vectors encoding a population of said second polypeptide chains in free form into host organisms which express a population of said first polypeptide chains.

7. A method according to claim 1 wherein said second polypeptide chains are each expressed as a fusion with a component of a rgdp which thereby displays said second polypeptide chains at the surface of rgdps.

8. A method according to claim 1 wherein either or both of the populations of said first and second chains polypeptide chains is derived from a repertoire selected from the group consisting of:
   (i) the repertoire of rearranged immunoglobulin genes of an animal immunized with a complementary sbp member;
   (ii) the repertoire of rearranged immunoglobulin genes of an animal not immunized with a complementary sbp member;
   (iii) the repertoire of artificially rearranged immunoglobulin gene or genes;
   (iv) a repertoire of an immunoglobulin homolog gene or genes;
   (v) a repertoire of sequences derived from a germ-line immunoglobulin gene or genes;
   (vi) a repertoire of an immunoglobulin gene or genes artificially mutated by the introduction of one or more point mutations; and
   (vii) a mixture of any of (i), (ii), (iii), (iv), (v) and (vi).

9. A method according to claim 1 wherein said sbp members displayed by rgdps are scFv molecules.

10. A method according to claim 1 wherein the rgdp is a bacteriophage, the host is a bacterium, and said component of the rgdp is a capsid protein for the bacteriophage.

11. A method according to claim 10 wherein the phage is a filamentous phage.

12. The method according to claim 11 wherein the phage is selected from the group consisting of the class 1 phages, Fd, M13, f1, If1, Ike ZJ/Z, Ff and the class II phages xf, Pf1 and Pf3.

13. A method according to claim 11 or claim 12 wherein the first polypeptide chains are expressed as fusions with the gene III capsid protein of phage fd or its counterpart in another filamentous phage.

14. A method according to claim 13 wherein the first polypeptide chains are each inserted in the N-terminal region of the mature capsid protein downstream of a secretory leader peptide.

15. A method according to claim 10 wherein the host is *E. coli*.

16. A method according to claim 1 wherein rgdps formed by said expression are selected or screened to provide an individual sbp member or a mixed population of said sbp members associated in their respective rgdps with nucleic acid encoding a polypeptide chain thereof.

17. A method of preparing an individual specific binding pair member, a mixed population of specific binding pair member, or polypeptide chain components thereof comprising the steps of:
  (i) obtaining nucleic acid from one or more rgdps produced by a method according to claim 16; and
  (ii) producing by expression from the nucleic acid obtained in step (i) an individual specific binding pair member, a mixed population of specific binding pair members, or polypeptide chain components thereof.

18. A method of preparing nucleic acid encoding an individual specific binding pair member, a mixed population of specific binding pair members, or polypeptide chain components thereof comprising the steps of:
  (i) obtaining nucleic acid from one or more rgdps produced by a method according to claim 16; and
  (ii) producing from the nucleic acid obtained in step (i) nucleic acid which encodes an individual specific binding pair member, a mixed population of specific binding pair members, or polypeptide chain components thereof.

19. A method according to claim 16 wherein the rgdps are selected by affinity with a member complementary to said sbp member.

20. A method according to claim 19 which comprises recovering any rgdps bound to said complementary sbp member by washing with an eluant.

21. A method according to claim 19 wherein the rgdp is applied to said complementary sbp member in the presence of a molecule which competes with said package for binding to said complementary sbp member.

22. A method according to claim 20 wherein the eluant contains a molecule which compete with said rgdp for binding to the complementary sbp member.

23. A method according to any one of claims 16 or 19–22 wherein nucleic acid derived from a selected or screened rgdp is used to express said sbp member or a fragment or derivative thereof in a recombinant host organism.

24. A method of producing one or a selected population of multichain polypeptide members of a specific binding pair (sbp members) comprising:
  (a) a first polypeptide chain comprising an antibody heavy chain variable domain and a second polypeptide chain comprising an antibody light chain variable domain, or
  (b) a first polypeptide chain comprising an antibody light chain variable domain and a second polypeptide chain comprising an antibody heavy chain variable domain,
and specific for a counterpart specific binding pair member of interest, which method comprises:
  (i) introducing into host cells
    (A) first vectors comprising nucleic acid encoding a genetically diverse population of said first polypeptide chain fused to a component of a secreted replicable genetic display package (rgdp) for display of said first polypeptide chains at the surface of rgdps, and
    (B) second vectors comprising nucleic acid encoding a unique or restricted population of said second polypeptide chain;
  said first vectors being packaged in infectious rgdps and said introducting of said first vectors into host cells being by infection into host cells harboring said second vectors, or
  said second vectors being packaged in infectious rgdps and said introducing of said second vectors into host cells being by infection into host cells harboring said first vectors;
  (ii) expressing said first and second polypeptide chains within the host cells to form a library of said multichain sbp members displayed by rgdps,
  said genetically diverse population of first polypeptide chains being expressed from nucleic acid that is packaged using said rgdp component, whereby each said rgdp contains genetic material which encodes a first polypeptide chain of the sbp member displayed at its surface;
  (iii) selecting by affinity with said counterpart sbp member of interest multichain sbp members specific for said counterpart sbp member associated in their respective rgdps with nucleic acid encoding a said first polypeptide chain of said multichain sbp members;
  (iv) combining said first polypeptide chains of multichain sbp members selected in step (iii) with a genetically diverse population of second polypeptide chains of multichain sbp members, the said second polypeptide chains being fused to a component of a rgdp which thereby displays them at the surface of rgdps, the said combining forming a library of multichain sbp members from which one or more multichain sbp members for said counterpart sbp member of interest are selectable by affinity with said counterpart sbp member of interest.

25. A method according to claim 24 wherein said selectable sbp members are scFv molecules.

26. A method according to claim 25 wherein nucleic acid encoding a said first or second polypeptide chain is linked downstream to a viral capsid protein through a suppressible translational stop codon.

27. A method according to claim 24 wherein said multichain sbp members are antibodies, or other members of the immunoglobulin family, or binding fragments thereof.

28. A method according to claim 27 comprising an additional step 5 wherein humanized antibodies for said antigen are selected by affinity with said antigen.

29. A method according to claim 27 wherein each of said second polypeptide chains of steps (i) and (ii) comprises a variable domain derived from a non-human animal antibody specific for the antigen of interest.

30. A method according to claim 29 wherein said second polypeptide chains of (i) and (ii) are chimaeric, comprising a human antibody domain.

31. A method according to claim 30 wherein said human antibody domain comprises Cγ1.

* * * * *